(12) United States Patent
Dennis et al.

(10) Patent No.: US 7,892,550 B2
(45) Date of Patent: *Feb. 22, 2011

(54) ANTI-CMET ANTIBODIES

(75) Inventors: Mark S. Dennis, San Carlos, CA (US);
Karen Billeci, San Bruno, CA (US);
Judy Young, San Carlos, CA (US);
Zhong Zheng, Foster City, CA (US)

(73) Assignee: Genentech, Inc., South San Francisco, CA (US)

( * ) Notice: Subject to any disclaimer, the term of this patent is extended or adjusted under 35 U.S.C. 154(b) by 879 days.

This patent is subject to a terminal disclaimer.

(21) Appl. No.: 11/537,760

(22) Filed: Oct. 2, 2006

(65) Prior Publication Data

US 2007/0092520 A1    Apr. 26, 2007

Related U.S. Application Data

(63) Continuation of application No. 11/196,917, filed on Aug. 4, 2005, now Pat. No. 7,476,724.

(60) Provisional application No. 60/598,991, filed on Aug. 5, 2004.

(51) Int. Cl.
*A61K 39/395* (2006.01)

(52) U.S. Cl. .............. 424/143.1; 424/155.1; 424/156.1; 536/23.53; 435/326

(58) Field of Classification Search ....................... None
See application file for complete search history.

(56) References Cited

U.S. PATENT DOCUMENTS

| | | | |
|---|---|---|---|
| 5,686,292 A | 11/1997 | Schwall et al. | |
| 5,731,168 A * | 3/1998 | Carter et al. | 435/69.1 |
| 5,859,205 A * | 1/1999 | Adair et al. | 530/387.3 |
| 6,165,745 A * | 12/2000 | Ward et al. | 435/69.1 |
| 6,468,529 B1 * | 10/2002 | Schwall et al. | 424/130.1 |
| 7,476,724 B2 * | 1/2009 | Dennis et al. | 530/388.8 |
| 2005/0054019 A1 * | 3/2005 | Michaud et al. | 435/7.23 |

FOREIGN PATENT DOCUMENTS

| | | |
|---|---|---|
| WO | WO 96/38557 | 12/1996 |
| WO | WO 2004/016769 | 2/2004 |
| WO | WO 2004/072117 | 8/2004 |
| WO | WO 2005/016382 | 2/2005 |
| WO | WO 2005/063816 A2 | 7/2005 |

OTHER PUBLICATIONS

Portolano et al., J Immunol. Feb. 1, 1993;150(3):880-7.*
Vajdos et al., J Mol Biol. Jul. 5, 2002;320(2):415-28.*
Baca et al., J Biol Chem. Apr. 18, 1997 ;272(16):10678-84.*
Tramontano et al., J Mol Biol. Sep. 5, 1990;215(1):175-82.*
Antibodies, A laboratory manual, Harlow and Lane , Cold Spring Harbor Laboratory, 1988, p. 28.*
Eduardo Padlan, Mol Immunol. Feb. 1994;31(3):169-217.*
Demignot et al., Cancer Res. 1990, 50: 2936-2942.*
Atwell et al., J Mol Biol. Jul. 4, 1997;270(1):26-35.*
Parham, J. Immunol., 1983, 131:2895-2902.*
Prat et al., J Cell Sci. Jan. 1998;111 ( Pt 2):237-47.*
Angeloni et al., "The Soluble Sema Domain of the RON Receptor Inhibits Macrophage-stimulating Protein-induced Receptor Activation" *Journal of Biological Chemistry* 279(5):3726-3732 (Jan. 2004).
Antipenko et al., "Structure of the Semaphorin-3A Receptor Binding Module" *Neuron* 39:589-598 (Aug. 14, 2003).
Bardelli et al., "Gab1 Coupling to the HGF/Met Receptor Multifunctional Docking Site Requires Binding of Grb2 and Correlates with the Transforming Potential" *Oncogene* 15:3103-3111 (1997).
Bertotti et al., "Tyrosine Kinase Signal Specificity: Lessons from the HGF Receptor" *Trends Biochem. Sci.* 28(10):527-533 (Oct. 2003).
Bladt et al., "Essential Role for the C-met Receptor in the Migration of Myogenic Precursor Cells into the Limb Bud" *Nature* 376:768-770 (Aug. 31, 1995).
Blechman et al., "The Fourth Immunoglobulin Domain of the Stem Cell Factor Receptor Couples Ligand Binding to Signal Transduction" *Cell* 80:103-113 (Jan. 13, 1995).
Boix et al., "C-Met mRNA Overexpression in Human Hepatocellular Carcinoma" *Hepatology* 19(1):88-91 (Jan. 1994).
Bottaro et al., "Identification of the Hepatocyte Growth Factor Receptor as the c-met Proto-Oncogene Product" *Science* 251:802-804 (Feb. 15, 1991).
Bussolino et al., "Hepatocyte Growth Factor is a Potent Angiogenic Factor Which Stimulates Endothelial Cell Motility and Growth" *Journal of Cell Biology* 119(3):629-641 (Nov. 1992).
Carter et al., "Humanization of an Anti-p185$^{HER2}$ Antibody For Human Cancer Therapy" *Proc. Natl. Acad. Sci. USA* 89(10):4285-4289 (May 1992).
Coltella at al., "Role of the MET/HGF Receptor in Proliferation and Invasive Behavior of Osteosarcoma" *Faseb Journal* 17:1162-1164 (Jun. 2003).
Cooper et al., "Molecular cloning of a new transforming gene from a chemically transformed human cell line" *Nature* 311:29-33 (Sep. 6, 1984).
Danilkovitch-Miagkova & Zbar, "Dysregulation of Met receptor tyrosine kinase activity in invasive tumors" *The Journal of Clinical Investigation* 109(7):863-867 (Apr. 2002).
Di Renzo et al., "Overexpression and Amplification of the Met/HGF Receptor Gene During the Progression of Colorectal Cancer" *Clinical Cancer Research* 1:147-154 (Feb. 1995).
Ferguson et al., "EGF Activates its Receptor by Removing Interactions that Autoinhibit Ectodomain Dimerization" *Molecular Cell* 11:507-517 (Feb. 2003).
Furge et al., "Met Receptor Tyrosine Kinase: Enhanced Signaling Through Adapter Proteins" *Oncogene* 19:5582-5589 (2000).

(Continued)

*Primary Examiner*—Zachary Skelding
(74) *Attorney, Agent, or Firm*—Cara Coburn

(57) ABSTRACT

The invention provides therapeutic anti-c-met antibodies, and compositions comprising and methods of using these antibodies.

67 Claims, 14 Drawing Sheets

OTHER PUBLICATIONS

Gallop et al., "Applications of Combinatorial Technologies to Drug Discovery Background and peptide combinatorial libraries" *Journal of Medicinal Chemistry* 37(9):1233-1251 (Apr. 29, 1994).

Garrett et al., "Crystal Structure of a Truncated Epidermal Growth Factor Receptor Extracellular Domain Bound to Transforming Growth Factor Alpha" *Cell* 110:763-773 (Sep. 20, 2002).

Gherardi et al., "Functional map and domain structure of MET, the product of the c-met protooncogene and receptor for hepatocyte growth factor/scatter factor" *Proc. Natl. Acad. Sci. USA* 100(21):12039-12044 (Oct. 14, 2003).

Giancotti et al., "Integrin Signaling" *Science* 285:1028-1032 (Aug. 13, 1999).

Giordano et al., "Biosynthesis of the Protein Encoded by the C-MET Proto-Oncogene" *Oncogene* 4:1383-1388 (1989).

Giordano et al., "Different Point Mutations in the MET Oncogene Elicit Distinct Biological Properties" *The Faseb Journal* 14:399-406 (Feb. 2000).

Giordano et al., "The Semaphorin 4D Receptor Controls Invasive Growth by Coupling with MET" *Nature Cell Biology* 4:720-724 (Sep. 2002).

Hakimi et al., "Reduced immunogenicity and improved pharmacokinetics of humanized anti-Tac in cynomolgus monkeys" *J Immunol.* 147(4):1352-1359 (Aug. 15, 1991).

Hamanoue et al., "Neurotrophic Effect of Hepatocyte Growth Factor on Central Nervous System in Vitro" *Journal of Neuroscience Research* 43:554-564 (1996).

Hartmann et al., "The Motility Signal of Scatter Factor/Hepatocyte Growth Factor Mediated Through the Journal Receptor Tyrosine Kinase Met Requires Intracellular Action of Ras" *Journal of Biological Chemistry* 269(35):21936-21939 (Sep. 2, 1994).

Jaffers et al., "Monoclonal Antibody Therapy, Anti-Idiotypic and Non-Anti-Idiotypic Antibodies to OKT3 Arising Despite Intense Immunosuppression" *Transplantation* 41(5):572-578 (May 1986).

Jeffers et al., "Activating Mutations for the Met Tyrosine Kinase Receptor in Human Cancer" *Proc. Natl. Acad. Sci. USA* 94:11445-11450 (Oct. 1997).

Jeffers et al., "Enhanced Tumorigenicity and Invasion-Metastasis by Hepatocyte Growth Factor/Scatter Factor-met Signaling in Human Cells Concomittant with Induction fo the Urokinase Proteolysis Network" *Molecular & Cellular Biology* 16(3):1115-1125 (Mar. 1996).

Jin et al., "Expression of Scatter Factor and C-Met Receptor in Benign and Malignant Breast Tissue" *Cancer* 79(4):749-760 (Feb. 15, 1997).

Junghans et al., "Anti-Tac-H, a Humanized Antibody to the Interleukin 2 Receptor with New Features for Immunotherapy in Malignant and Immune Disorders" *Cancer Research* 50(5):1495-1502 (Mar. 1, 1990).

Khazaeli et al., "Phase I trial of multiple large doses of murine monoclonal antibody C017-1A. II. Pharmacokinetics and immune response" *J Natl Cancer Inst.* 80(12):937-942 (Aug. 17, 1988).

Kuniyasu et al., "Aberrant Expression of C-met mRNA in Human Gastric Carcinomas" *Int. J. Cancer* 55:72-75 (1993).

Lee et al., "High-affinity human antibodies from phage-displayed synthetic Fab libraries with a single framework scaffold" *J Mol Biol.* 340(5):1073-1093 (Jul. 23, 2004).

Lev et al., "A Recombinant Ectodomain of the Receptor for the Stem Cell Factor (SCF) Retains Ligand-induced Receptor Dimerization and Antagonizes SCF-Stimulated Cellular Responses" *Journal of Biological Chemistry* 267(15):10866-10873 (May 25, 1992).

Liu et al., "Overexpression of C-met Proto-Oncogene But Not Epidermal Growth Factor Receptor or C-erbB-2 in Primary Human Colorectal Carcinomas" *Oncogene* 7:181-185 (1992).

Lokker et al., "Structure-Function Analysis of Hepatocyte Growth Factor: Identification of Variants that Lack Mitogenic Activity Yet Retain High Affinity Receptor Binding" *EMBO Journal* 11(7):2503-2510 (1992).

Lorenzato et al., "Novel Somatic Mutations of the MET Oncogene in Human Carcinoma Metastases Activating Cell Motility and Invasion" *Cancer Research* 62:7025-7030 (Dec. 1, 2002).

Love et al., "The Ligand-binding Face of the Semaphorins Revealed by the High-Resolution Crystal Structure of SEMA4D" *Nature Structural Biology* 10(10):843-848 (Oct. 2003).

Maina et al., "Uncoupling of Grb2 from the Met Receptor in Vivo Reveals Complex Roles in Muscle Development" *Cell* 87:531-542 (Nov. 1, 1996).

Matsumoto et al., "Roles of HGF as a pleiotropic factor in organ regeneration" *Exs* 65:225-249 (1993).

Maulik et al., "Role of the hepatocyte growth factor receptor, c-Met, in oncogenesis and potential for therapeutic inhibition" *Cytokine & Growth Factor Reviews* 13:41-59 (2002).

Meiners et al., "Role of Morphogenetic Factors in Metastasis of Mammary Carcinoma Cells" *Oncogene* 16:9-20 (1998).

Michieli P et al., "Targeting the tumor and its microenvironment by a dual-function decoy Met receptor" *Cancer Cell* 6(1):61-73 (Jul. 2004).

Miller, R. et al., "Monoclonal antibody therapeutic trials in seven patients with T-cell lymphoma" *Blood* 62:988-995 (1983).

Morello et al., "MET Receptor is Overexpressed but not Mutated in Oral Squamous Cell Carcinomas" *Journal of Cellular Physiology* 189:285-290 (2001).

Morton, P.A., et al., "In vitro and in vivo activity of fully-human monoclonal antibodies to c-Met protein tyrosine kinase" *Proceedings of the Annual Meeting of the American Association for Cancer Research* 44:1116 (Jul. 2003).

Naka et al., "Activation of Hepatocyte Growth Factor by Proteolytic Conversion of a Single Chain Form to a Heterodimer" *The Journal of Biological Chemistry* 267(28):20114-20119 (Oct. 5, 1992).

Naldini et al., "Scatter Factor and Hepatocyte Growth Factor are Indistinguishable Ligands for the MET Receptor" *EMBO Journal* 10(10):2867-2878 (1991).

Natali et al., "Overexpression of the Met/HGF Receptor in Renal Cell Carcinomas" *Int. J. Cancer* 69:212-217 (1996).

Nguyen et al., "Association of the Multisubstrate Docking Protein Gab1 with the Hepatocyte Growth Factor Receptor Requires a Functional Grb2 Binding Site Involving Tyrosine 1356" *Journal of Biological Chemistry* 272(33):20811-20819 (Aug. 15, 1997).

Nusrat et al., "Hepatocyte Growth Factor/Scatter Factor Effects on Epithelia. Regulation of Intercellular Junctions in Transformed and Natural Intestinal Epithelia . . . " *J. Clin. Invest.* 93:2056-2065 (May 1994).

Ogiso et al., "Crystal Structure of the Complex of Human Epidermal Growth Factor and Receptor Extracellular Domains" *Cell* 110:775-787 (Sep. 20, 2002).

Olivero et al., "Novel Mutation in the ATP-Binding Site of the MET Oncogen Tyrosine Kinase in a HPRCC Family" *Int. J. Cancer* 82:640-643 (1999).

Olivero et al., "Overexpression and Activation of Hepatocyte Growth Factor/Scatter Factor in Human Non-Small-Cell Lung Carcinomas" *Br. J. Cancer* 74:1862-1868 (1996).

Orian-Rousseau et al., "CD44 is Required for two Consecutive Steps in HGF/c-MET Signaling" *Genes & Development* 16:3074-3086 (2002).

Park et al., "Mechanism of Met Oncogene Activation" *Cell* 45:895-904 (Jun. 20, 1986).

Peek et al., "Unusual Proteolytic Activation of Pro-hepatocyte Growth Factor by Plasma Kallikrein and Coagulation Factor XIa" *Journal of Biological Chemistry* 277(49):47804-47809 (Dec. 6, 2002).

Pelicci et al., "The Motogenic and Mitogenic Responses to HGF are Amplified by the Shc Adaptor Protein" *Oncogene* 10:1631-1638 (1995).

Plotnikov et al., "Structural Basis for FGF Receptor Dimerization and Activation" *Cell* 98:641-650 (Sep. 3, 1999).

Ponzetto et al., "A Multifunctional Docking Site Mediates Signaling and Transformation by the Hepatocyte Growth Factor/Scatter Factor Receptor Family" *Cell* 77:261-271 (Apr. 22, 1994).

Ponzetto et al., "Specific Uncoupling of GRB2 from the Met Receptor. Differential Effects on Transformation and Motility" *Journal of Biological Chemistry* 271(24):14119-14123 (Jun. 14, 1996).

Reichmann, L. et al., "Reshaping human antibodies for therapy" *Nature* 332:323-337 (1988).

Robertson et al., "RTK Mutations and Human Syndromes when Good Receptors Turn Bad" *Trends Genet.* 16(8):265-271 (Aug. 16, 2000).

Royal et al., "Hepatocyte Growth Factor-Induced Scatter of Madin-Darby Canine Kidney Cells Requires Phosphatidylinositol 3-Kinase" *Journal of Biological Chemistry* 270(46):27780-27787 (Nov. 17, 1995).

Schmidt et al., "Germline and Somatic Mutations in the Tyrosine Kinase Domain of the MET Proto-oncogene in Papillary Renal Carcinomas" *Nature Genetics* 16:68-73 (May 1997).

Schmidt et al., "Novel Mutations of the MET Proto-oncogene in Papillary Renal Carcinomas" *Oncogene* 18:2343-2350 (1999).

Schmidt et al., "Scatter factor/hepatocyte growth factor is essential for liver development" *Nature* 373:699-702 (Feb. 23, 1995).

Sears et al., "Effects of monoclonal antibody immunotherapy on patients with gastrointestinal adenocarcinoma" *J Biol Response Mod.* 3(2):138-150 (1984).

Shawler et al., "Human immune response to multiple injections of murine monoclonal IgG" *J Immunol.* 135(2):1530-1535 (1985).

Suzuki et al., "Expression of the C-Met Protooncogene in Human Hepatocellular Carcinoma" *Hepatology* 20:1231-1236 (Nov. 1994).

Tamagnone et al., "Plexins are a Large Family of Receptors for Transmembrane, Secreted, and GPI-Anchored Semaphorins in Vertebrates" *Cell* 99:71-80 (Oct. 1, 1999).

Tempest et al., "Structure of the Met Protein and Variation of Met Protein Kinase Activity Among Human Tumour Cell Lines" *Br. J. Cancer* 58(1):3-7 (Jul. 1988).

Trusolino & Comoglio, "Scatter-Factor and Semaphorin Receptors: Cell Signalling for Invasive Growth" *Nature Rev. Cancer* 2:289-300 (Apr. 2002).

Trusolino et al., "A Signaling Adapter Function for Alpha6beta4 Integrin in the Control of HGF-Dependent Invasive Growth" *Cell* 107:643-654 (Nov. 30, 2001).

Uehara et al., "Placental defect and embryonic lethality in mice lacking hepatocyte growth factor/ scatter factor" *Nature* 373:702-705 (Feb. 23, 1995).

Van Vactor et al., "Neural Developmlent: The Semantics of Axon Guidance" *Current Biology* 9(6):R201-204 (1999).

Weidner et al., "Interaction Between Gab1 and the C-Met Receptor Tyrosine Kinase is Responsible for Epithelial Morphogenesis" *Nature* 384:173-176 (Nov. 14, 1996).

Wiesmann et al., "Crystal Structure at 1.7 A Resolution of VEGF in Complex with Domain 2 of the Flt-1 Receptor." *Cell* 91:695-704 (Nov. 28, 1997).

Wiesmann et al., "Crystal Structure of Nerve Growth Factor in Complex with the Ligand-Binding Domain of the TrkA Receptor" *Nature* 401:184-188 (Sep. 9, 1999).

Dufner et al., "Harnessing phage and ribosome display for antibody optimisation" *Trends in Biotechnology* 24(11):523-529 (2006).

* cited by examiner

FIG. 1A

Variable Heavy Chain

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| huIII | E | V | Q | L | V | E | S | G | G | G | L | V | Q | P | G | G | S | L | R | L | S | C | A | A | S | G | F | T | F | S | S | Y | A | M | S | W | V | R | Q | A | P | G |
| mu5D5 | Q | V | Q | L | Q | Q | S | G | P | E | L | V | R | P | G | A | S | V | K | M | S | C | R | A | S | G | Y | T | F | T | T | Y | W | L | H | W | V | K | Q | R | P | G |
| 5D5 Graft | E | V | Q | L | V | E | S | G | G | G | L | V | Q | P | G | G | S | L | R | L | S | C | A | A | S | G | Y | T | F | T | S | Y | W | L | H | W | V | R | Q | A | P | G |

CDR-H1: positions 26–35

| Kabat# | 43 | 44 | 45 | 46 | 47 | 48 | 49 | 50 | 51 | 52 | a | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | a |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| huIII | K | G | L | E | W | V | S | V | I | S | G | D | G | G | S | T | Y | Y | A | D | S | V | K | G | R | F | T | I | S | R | D | N | S | K | N | T | L | Y | L | Q | M | N |
| mu5D5 | Q | G | L | E | W | I | G | M | I | D | P | S | N | S | D | T | R | F | N | P | N | F | K | D | K | A | T | L | N | V | D | R | S | S | N | T | A | Y | M | L | L | S |
| 5D5 Graft | K | G | L | E | W | V | G | M | I | D | P | S | N | S | D | T | R | F | N | P | N | F | K | D | R | F | T | I | S | A | D | T | S | K | N | T | A | Y | L | Q | M | N |

CDR-H2: positions 50–65

| Kabat# | b | c | 83 | 84 | 85 | 86 | 87 | 88 | 89 | 90 | 91 | 92 | 93 | 94 | 95 | 96 | 97 | 98 | 99 | 100 | a | k | 101 | 102 | 103 | 104 | 105 | 106 | 107 | 108 | 109 | 110 | 111 | 112 | 113 |
|---|---|---|---|---|---|---|---|---|---|---|---|---|---|---|---|---|---|---|---|---|---|---|---|---|---|---|---|---|---|---|---|---|---|---|---|
| huIII | | | S | L | R | A | E | D | T | A | V | Y | Y | C | A | R | | | | | | | | | | | G | | | | F | D | Y | W | G | Q | G | T | L | V | T | V | S | S |
| mu5D5 | S | L | T | S | A | D | S | A | V | Y | Y | C | A | T | Y | G | S | Y | V | S | P | L | D | Y | W | G | Q | G | T | S | V | T | V | S | S |
| 5D5 Graft | S | L | R | A | E | D | T | A | V | Y | Y | C | A | R | Y | G | S | Y | V | S | P | L | D | Y | W | G | Q | G | T | L | V | T | V | S | S |

CDR-H3: positions 95–102

SEQ ID NO: 13
SEQ ID NO: 10
SEQ ID NO: 14

HVR-L2

| W | A | S | T | R | E | S | SEQ ID NO: 139 |
|---|---|---|---|---|---|---|---|
| W | A | S | T | P | A | S | SEQ ID NO: 56 |
| W | A | S | I | R | D | R | SEQ ID NO: 57 |
| M | P | N | T | R | D | S | SEQ ID NO: 58 |
| W | A | S | T | R | D | I | SEQ ID NO: 59 |
| W | A | G | T | R | E | M | SEQ ID NO: 60 |
| L | A | S | N | R | E | G | SEQ ID NO: 61 |
| W | T | G | N | R | E | M | SEQ ID NO: 62 |
| W | A | R | T | R | E | S | SEQ ID NO: 63 |
| W | A | S | T | R | E | S | SEQ ID NO: 64 |
| W | A | S | T | P | E | S | SEQ ID NO: 65 |
| W | A | S | X | N | I | T | SEQ ID NO: 66 |
| W | A | S | T | R | E | S | SEQ ID NO: 67 |
| W | A | N | F | R | V | S | SEQ ID NO: 68 |
| W | T | S | N | R | V | S | SEQ ID NO: 69 |
| L | G | T | R | T | L | V | SEQ ID NO: 70 |
| L | A | T | T | T | R | V | SEQ ID NO: 71 |
| W | A | S | T | L | V | S | SEQ ID NO: 72 |
| W | A | S | T | G | V | S | SEQ ID NO: 73 |
| W | A | S | T | R | V | S | SEQ ID NO: 74 |
| W | S | S | T | R | V | S | SEQ ID NO: 75 |

HVR-H1 (position 32)

| G | Y | T | F | T | S | Y | W | L | H | SEQ ID NO: 140 |
|---|---|---|---|---|---|---|---|---|---|---|
| G | Y | N | F | T | G | F | W | M | H | SEQ ID NO: 76 |
| G | Y | T | F | I | D | F | W | L | H | SEQ ID NO: 77 |
| G | Y | T | F | T | S | F | W | L | H | SEQ ID NO: 78 |
| G | Y | T | F | T | S | H | W | L | H | SEQ ID NO: 79 |
| G | Y | P | F | T | T | R | W | L | H | SEQ ID NO: 80 |
| G | Y | L | F | T | S | S | W | L | H | SEQ ID NO: 81 |
| G | Y | N | F | S | S | S | W | L | H | SEQ ID NO: 82 |
| G | Y | P | F | T | T | K | S | W | L | H | SEQ ID NO: 83 |
| G | Y | S | F | T | T | S | W | V | H | SEQ ID NO: 84 |
| G | Y | T | F | T | D | S | W | L | H | SEQ ID NO: 85 |
| T | Y | T | F | F | S | S | W | L | H | SEQ ID NO: 86 |
| G | Y | T | F | T | S | S | W | L | H | SEQ ID NO: 87 |
| G | Y | A | F | T | S | T | W | L | H | SEQ ID NO: 88 |
| G | Y | I | F | T | S | S | W | L | H | SEQ ID NO: 89 |
| G | Y | N | F | S | F | T | S | W | L | H | SEQ ID NO: 90 |
| G | Y | S | F | T | S | V | W | L | H | SEQ ID NO: 91 |
| G | Y | T | F | T | T | R | V | W | L | H | SEQ ID NO: 92 |
| G | Y | T | F | A | T | S | Y | W | L | H | SEQ ID NO: 93 |
| G | Y | I | F | T | T | Y | W | L | H | SEQ ID NO: 94 |
| G | Y | T | F | T | S | Y | W | L | H | SEQ ID NO: 95 |
| G | Y | T | F | Y | S | Y | W | L | H | SEQ ID NO: 96 |

HVR-H2

| G | M | I | D | P | S | N | S | D | T | R | F | N | P | N | F | K | D | SEQ ID NO |
|---|---|---|---|---|---|---|---|---|---|---|---|---|---|---|---|---|---|---|
| G | M | I | H | P | S | N | S | D | T | R | F | N | P | N | F | K | D | SEQ ID NO: 141 |
| G | M | I | D | P | S | N | S | D | T | R | F | N | P | D | F | F | E | SEQ ID NO: 97 |
| G | M | I | D | P | S | N | S | D | T | R | F | N | P | T | K | F | E | SEQ ID NO: 98 |
| G | M | I | D | P | S | N | S | D | T | R | F | N | P | K | K | F | H | SEQ ID NO: 99 |
| G | M | I | D | P | S | Y | S | S | T | R | F | N | P | K | Y | F | K | SEQ ID NO: 100 |
| G | M | I | D | P | S | N | S | D | T | R | F | N | P | K | Y | F | N | SEQ ID NO: 101 |
| G | M | I | D | P | S | N | S | D | T | R | F | N | P | K | F | F | N | SEQ ID NO: 102 |
| G | M | I | D | P | S | N | S | D | T | R | F | N | P | N | F | F | D | SEQ ID NO: 103 |
| G | M | I | D | P | S | N | S | D | T | R | F | N | P | N | F | F | E | SEQ ID NO: 104 |
| G | M | I | D | P | S | N | S | D | T | R | F | N | P | O | N | F | D | SEQ ID NO: 105 |
| G | M | I | D | P | S | N | S | D | T | R | F | N | P | N | F | F | E | SEQ ID NO: 106 |
| G | M | I | D | P | S | N | S | D | T | R | F | N | P | N | F | F | H | SEQ ID NO: 107 |
| G | M | I | D | P | S | N | S | D | T | R | F | N | P | N | L | F | E | SEQ ID NO: 108 |
| G | M | I | D | P | S | N | S | D | T | R | F | N | P | S | L | F | O | SEQ ID NO: 109 |
| G | M | I | D | P | S | N | S | D | T | R | F | N | P | T | F | F | E | SEQ ID NO: 110 |
| G | M | I | D | P | S | N | S | D | T | R | F | N | P | V | L | F | L | SEQ ID NO: 111 |
| G | M | I | D | P | S | N | S | D | T | R | F | N | P | V | L | K | K | SEQ ID NO: 112 |

HVR-H3

| S | Y | G | S | Y | V | S | P | L | D | Y | SEQ ID NO |
|---|---|---|---|---|---|---|---|---|---|---|---|
| S | Y | G | S | Y | V | S | P | L | D | Y | SEQ ID NO: 142 |
| S | Y | G | S | Y | V | L | P | L | D | Y | SEQ ID NO: 113 |
| S | Y | G | S | Y | V | S | P | L | D | Y | SEQ ID NO: 114 |
| S | Y | R | S | Y | R | I | P | L | D | Y | SEQ ID NO: 115 |
| S | Y | R | S | Y | V | L | P | L | D | Y | SEQ ID NO: 116 |
| S | Y | R | S | Y | V | L | P | L | D | Q | SEQ ID NO: 117 |
| S | Y | S | S | Y | F | T | P | L | D | Y | SEQ ID NO: 118 |
| S | Y | S | S | Y | M | R | P | L | D | Y | SEQ ID NO: 119 |
| S | Y | S | S | Y | T | R | P | L | D | Y | SEQ ID NO: 120 |
| S | Y | S | S | Y | V | T | S | L | D | Y | SEQ ID NO: 121 |
| T | Y | G | S | Y | E | K | P | L | D | Y | SEQ ID NO: 122 |
| T | Y | G | S | Y | V | K | P | L | D | Y | SEQ ID NO: 123 |
| T | Y | G | S | Y | V | V | P | L | D | Y | SEQ ID NO: 124 |
| T | Y | H | S | Y | V | T | P | L | D | Y | SEQ ID NO: 125 |
| T | Y | R | S | Y | V | S | P | L | D | Y | SEQ ID NO: 126 |
| T | Y | R | G | Y | F | T | P | L | D | Y | SEQ ID NO: 127 |
| T | Y | R | S | Y | F | V | P | L | D | Y | SEQ ID NO: 128 |
| T | Y | R | S | Y | V | K | P | L | D | Y | SEQ ID NO: 129 |
| T | Y | R | S | Y | V | R | P | L | D | Y | SEQ ID NO: 130 |
| T | Y | S | S | Y | V | S | P | L | D | Y | SEQ ID NO: 131 |
| T | Y | S | S | Y | V | K | S | P | L | Y | SEQ ID NO: 132 |
| T | Y | S | S | Y | V | K | P | L | D | Y | SEQ ID NO: 133 |
| T | Y | S | S | Y | V | R | P | L | D | Y | SEQ ID NO: 134 |
| T | Y | S | S | Y | M | R | P | L | D | Y | SEQ ID NO: 135 |
| T | Y | S | S | Y | V | T | S | L | D | Y | SEQ ID NO: 136 |
| T | Y | S | S | Y | V | T | A | L | D | Y | SEQ ID NO: 137 |
| T | Y | T | S | Y | R | L | P | L | D | Y | SEQ ID NO: 138 |

HVR-H3

| | 94 | | 96 | | | 100 | | | | | | | |
|---|---|---|---|---|---|---|---|---|---|---|---|---|---|
| | S | Y | G | S | Y | V | S | P | L | D | Y | | |
| SEQ ID NO: 143 | S | Y | G | S | Y | V | S | P | L | D | Y | | |
| SEQ ID NO: 144 | S | Y | R | S | Y | R | T | P | L | D | Y | | |
| SEQ ID NO: 145 | S | Y | R | S | Y | V | T | P | L | D | Y | | |
| SEQ ID NO: 146 | S | Y | R | S | Y | V | V | P | L | D | Y | | |
| SEQ ID NO: 147 | S | Y | R | S | Y | V | V | P | L | D | S | | |
| SEQ ID NO: 148 | S | Y | S | S | Y | A | V | K | P | L | D | Y | |
| SEQ ID NO: 149 | S | Y | S | S | Y | A | V | L | P | L | D | Y | |
| SEQ ID NO: 150 | T | Y | A | S | Y | Y | A | T | P | L | D | Y | |
| SEQ ID NO: 151 | T | Y | A | S | Y | V | V | T | P | L | D | Y | |
| SEQ ID NO: 152 | T | Y | G | S | Y | V | T | A | L | D | H | | |
| SEQ ID NO: 153 | T | Y | G | S | Y | M | L | A | P | L | N | Y | |
| SEQ ID NO: 154 | T | Y | H | S | Y | V | V | P | L | D | Y | | |
| SEQ ID NO: 155 | T | Y | K | S | Y | V | L | V | P | L | D | Y | |
| SEQ ID NO: 156 | T | Y | R | S | Y | V | R | S | P | L | D | Y | |
| SEQ ID NO: 157 | T | Y | R | S | Y | V | R | S | P | L | D | Y | |
| SEQ ID NO: 158 | T | Y | R | S | Y | V | T | I | P | L | D | F | |
| SEQ ID NO: 159 | T | Y | S | S | Y | W | I | P | L | D | Y | | |
| SEQ ID NO: 160 | T | Y | S | S | Y | V | R | P | L | D | Y | | |
| SEQ ID NO: 161 | T | Y | S | S | Y | V | V | S | P | L | D | Y | |
| SEQ ID NO: 162 | T | Y | S | S | Y | V | V | T | S | L | D | Y | |
| SEQ ID NO: 163 | T | Y | S | S | Y | V | V | A | L | D | Y | | |

| | | | | | | | | | | | | | | | | | | | | | | SEQ ID | 5D5 Variants | ka (1/Ms) | kd (1/s) | KD (nM) |
|---|---|---|---|---|---|---|---|---|---|---|---|---|---|---|---|---|---|---|---|---|---|---|---|---|---|---|
| L2 | I | Y | W | A | S | T | R | E | S | G | V | | | | | | | | | | | SEQ ID NO: 164 | | | | |
| | I | Y | W | A | S | T | R | V | S | G | V | | | | | | | | | | | SEQ ID NO: 165 | #34 | 4.87E+04 | 3.52E-04 | 7.22 |
| H1 | A | S | G | Y | T | F | T | S | Y | W | L | H | W | V | | | | | | | | SEQ ID NO: 166 | | | | |
| | A | S | G | Y | T | F | T | S | S | W | L | H | W | V | | | | | | | | SEQ ID NO: 167 | #94 | 1.18E+04 | 4.50E-04 | 38.1 |
| H2 | W | V | G | M | I | D | P | S | N | S | N | T | R | F | N | P | N | F | K | D | R | F | | | | |
| | | | | M | I | D | P | S | N | S | D | T | R | F | N | T | K | F | E | D | R | F | SEQ ID NO: 168 | #4 | 6.30E+04 | 4.92E-04 | 7.81 |
| | | | | M | I | D | P | S | N | S | D | T | R | F | N | F | P | N | F | E | D | R | F | SEQ ID NO: 169 | #12 | 5.98E+04 | 5.06E-04 | 8.46 |
| | | | | M | I | D | P | S | N | S | D | T | R | F | N | P | N | F | K | D | R | F | SEQ ID NO: 170 | graft | no detectable binding at 500 nM | | |
| H3 | C | A | R | Y | G | S | S | Y | V | S | P | L | D | Y | W | G | | | | | | | | R94S | 5.16E+04 | 5.07E-04 | 9.83 |
| | C | A | (S) | Y | G | S | S | Y | V | S | P | L | D | Y | W | G | | | | | | | SEQ ID NO: 171 | OA-5D5 | 8.98E+04 | 7.43E-04 | 8.27 |
| | C | A | T | Y | G | S | S | Y | V | S | P | L | D | Y | W | G | | | | | | | SEQ ID NO: 172 | | | | |
| | | | | | | | | | | | | | | | | | | | | | | | SEQ ID NO: 173 | | | | |
| | C | A | T | Y | R | S | Y | V | S | P | L | D | Y | W | G | | | | | | | | SEQ ID NO: 174 | #49 | 2.86E+03 | 2.24E-04 | 78.3 |
| | C | A | S | Y | R | S | Y | V | T | P | L | D | Y | W | G | | | | | | | | SEQ ID NO: 175 | #92 | 1.99E+05 | 2.09E-04 | 1.05 |
| | C | A | T | Y | R | S | Y | V | T | P | L | D | Y | W | G | | | | | | | | SEQ ID NO: 176 | #78 | 2.36E+05 | 1.47E-04 | 0.625 |
| | C | A | T | Y | S | S | Y | V | T | S | L | D | Y | W | G | | | | | | | | SEQ ID NO: 177 | #75 | 8.31E+04 | 1.58E-04 | 1.9 |
| | C | A | T | Y | S | S | Y | V | T | A | L | D | Y | W | G | | | | | | | | SEQ ID NO: 178 | #95 | 9.05E+04 | 2.29E-04 | 2.53 |

```
I
A  QVQLVQSGAEVKKPGASVKVSCKASGYTFT -H1- WVRQAPGQGLEWMG -H2-
B  QVQLVQSGAEVKKPGASVKVSCKAS      -H1- WVRQAPGQGLEWM  -H2-
C  QVQLVQSGAEVKKPGASVKVSCKAS      -H1- WVRQAPGQGLEWM  -H2-
D  QVQLVQSGAEVKKPGASVKVSCKAS      -H1- WVRQAPGQGLEWM  -H2-

II
A  QVQLQESGPGLVKPSQTLSLTCTVSGGSVS -H1- WIRQPPGKGLEWIG -H2-
B  QVQLQESGPGLVKPSQTLSLTCTVS      -H1- WIRQPPGKGLEWI  -H2-
C  QVQLQESGPGLVKPSQTLSLTCTVS      -H1- WIRQPPGKGLEWI  -H2-
D  QVQLQESGPGLVKPSQTLSLTCTVS      -H1- WIRQPPGKGLEWI  -H2-

III
A  EVQLVESGGGLVQPGGSLRLSCAASGFTFS -H1- WVRQAPGKGLEWVS -H2-
B  EVQLVESGGGLVQPGGSLRLSCAAS      -H1- WVRQAPGKGLEWV  -H2-
C  EVQLVESGGGLVQPGGSLRLSCAAS      -H1- WVRQAPGKGLEWV  -H2-
D  EVQLVESGGGLVQPGGSLRLSCAAS      -H1- WVRQAPGKGLEWV  -H2-

Acceptor
A  EVQLVESGGGLVQPGGSLRLSCAASGFNIK -H1- WVRQAPGKGLEWVS -H2-
B  EVQLVESGGGLVQPGGSLRLSCAAS      -H1- WVRQAPGKGLEWV  -H2-
C  EVQLVESGGGLVQPGGSLRLSCAAS      -H1- WVRQAPGKGLEWV  -H2-

Second Acceptor
A  EVQLVESGGGLVQPGGSLRLSCAASGFNIK -H1- WVRQAPGKGLEWVS -H2-
B  EVQLVESGGGLVQPGGSLRLSCAAS      -H1- WVRQAPGKGLEWV  -H2-
C  EVQLVESGGGLVQPGGSLRLSCAAS      -H1- WVRQAPGKGLEWV  -H2-
D  EVQLVESGGGLVQPGGSLRLSCAAS      -H1- WVRQAPGKGLEWV  -H2-
```

I
A  RVTITADTSTSTAYMELSSLRSEDTAVYYCAR  -H3-  WGQGTLVTVSS  SEQ ID NO.:19
B  RVTITADTSTSTAYMELSSLRSEDTAVYYCAR  -H3-  WGQGTLVTVSS  SEQ ID NO.:20
C  RVTITADTSTSTAYMELSSLRSEDTAVYYCA   -H3-  WGQGTLVTVSS  SEQ ID NO.:21
D  RVTITADTSTSTAYMELSSLRSEDTAVYYC    -H3-  WGQGTLVTVSS  SEQ ID NO.:22

II
A  RVTISVDTSKNQFSLKLSSVTAADTAVYYCAR  -H3-  WGQGTLVTVSS  SEQ ID NO.:23
B  RVTISVDTSKNQFSLKLSSVTAADTAVYYCAR  -H3-  WGQGTLVTVSS  SEQ ID NO.:24
C  RVTISVDTSKNQFSLKLSSVTAADTAVYYCA   -H3-  WGQGTLVTVSS  SEQ ID NO.:25
D  RVTISVDTSKNQFSLKLSSVTAADTAVYYC    -H3-  WGQGTLVTVSS  SEQ ID NO.:26

III
A  RFTISRDNSKNTLYLQMNSLRAEDTAVYYCAR  -H3-  WGQGTLVTVSS  SEQ ID NO.:27
B  RFTISRDNSKNTLYLQMNSLRAEDTAVYYCAR  -H3-  WGQGTLVTVSS  SEQ ID NO.:28
C  RFTISRDNSKNTLYLQMNSLRAEDTAVYYCA   -H3-  WGQGTLVTVSS  SEQ ID NO.:29
D  RFTISRDNSKNTLYLQMNSLRAEDTAVYYC    -H3-  WGQGTLVTVSS  SEQ ID NO.:30

Acceptor
A  RFTISADTSKNTAYLQMNSLRAEDTAVYYCSR  -H3-  WGQGTLVTVSS  SEQ ID NO.:31
B  RFTISADTSKNTAYLQMNSLRAEDTAVYYCSR  -H3-  WGQGTLVTVSS  SEQ ID NO.:32
C  RFTISADTSKNTAYLQMNSLRAEDTAVYYCS   -H3-  WGQGTLVTVSS  SEQ ID NO.:33

Second Acceptor
A  RFTISADTSKNTAYLQMNSLRAEDTAVYYCAR  -H3-  WGQGTLVTVSS  SEQ ID NO.:34
B  RFTISADTSKNTAYLQMNSLRAEDTAVYYCAR  -H3-  WGQGTLVTVSS  SEQ ID NO.:35
C  RFTISADTSKNTAYLQMNSLRAEDTAVYYCA   -H3-  WGQGTLVTVSS  SEQ ID NO.:36
D  RFTISADTSKNTAYLQMNSLRAEDTAVYYC    -H3-  WGQGTLVTVSS  SEQ ID NO.:37

*FIG. 5B* kv1  DIQMTQSPSSLSASVGDRVTITC -L1- WYQQKPGKAPKLLIY -L2- GVPSRFSGSGSGTDFTLTISSLQP
kv2  DIVMTQSPLSLPVTPGEPASISC -L1- WYLQKPGQSPQLLIY -L2- GVPDRFSGSGSGTDFTLKISRVEA
kv3  EIVLTQSPGTLSLSPGERATLSC -L1- WYQQKPGQAPRLLIY -L2- GIPDRFSGSGSGTDFTLTISRLEP
kv4  DIVMTQSPDSLAVSLGERATINC -L1- WYQQKPGQPPKLLIY -L2- GVPDRFSGSGSGTDFTLTISSLQA

FIG. 6A kv1  EDFATYYC -L3- FGQGTKVEIK  SEQ ID NO.:38
kv2  EDVGVYYC -L3- FGQGTKVEIK  SEQ ID NO.:39
kv3  EDFAVYYC -L3- FGQGTKVEIK  SEQ ID NO.:40
kv4  EDVAVYYC -L3- FGQGTKVEIK  SEQ ID NO.:41

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 |
|---|---|---|---|---|---|---|---|---|---|---|---|---|---|---|---|---|---|---|---|---|---|---|---|---|---|---|---|
| mu5D5 | D | I | M | M | S | Q | S | P | S | S | L | T | V | S | V | G | E | K | V | T | V | S | C | K | S | S | Q |

| 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 | 61 |
|---|---|---|---|---|---|---|---|---|---|---|---|---|---|---|---|---|---|---|---|---|---|---|---|---|---|---|---|---|---|---|---|---|---|
| S | Q | K | N | Y | L | A | W | Y | Q | Q | K | P | G | Q | S | P | K | L | L | I | Y | W | A | S | T | R | E | S | G | V | P | D | R |

| 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 | 85 | 86 | 87 | 88 | 89 | 90 | 91 | 92 | 93 |
|---|---|---|---|---|---|---|---|---|---|---|---|---|---|---|---|---|---|---|---|---|---|---|---|---|---|---|---|---|---|---|---|
| F | T | G | S | G | S | G | T | D | F | T | L | T | I | T | S | V | K | A | D | D | L | A | V | Y | Y | C | Q | Q | Y | Y | A |

| 94 | 95 | 96 | 97 | 98 | 99 | 100 | 101 | 102 | 103 | 104 | 105 | 106 | 107 | 108 |
|---|---|---|---|---|---|---|---|---|---|---|---|---|---|---|
| Y | P | W | T | F | G | G | G | T | K | L | E | I | K | R |

(SEQ ID NO: 9)

HC

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 |
|---|---|---|---|---|---|---|---|---|---|---|---|---|---|---|---|---|---|---|---|---|---|---|---|---|---|---|---|---|---|---|---|---|---|
| mu5D5 | Q | V | Q | L | Q | Q | S | G | P | E | L | V | R | P | G | A | S | V | K | M | S | C | R | A | S | G | Y | T | F | T | S | Y | W |

| 34 | 35 | 36 | 37 | 38 | 39 | 40 | 41 | 42 | 43 | 44 | 45 | 46 | 47 | 48 | 49 | 50 | 51 | 52 | a | 53 | 54 | 55 | 56 | 57 | 58 | 59 | 60 | 61 | 62 | 63 | 64 | 65 |
|---|---|---|---|---|---|---|---|---|---|---|---|---|---|---|---|---|---|---|---|---|---|---|---|---|---|---|---|---|---|---|---|---|
| L | H | W | V | K | Q | R | P | G | Q | G | L | E | W | I | G | M | I | D | P | S | N | S | D | T | R | F | N | P | N | F | K | D |

| 66 | 67 | 68 | 69 | 70 | 71 | 72 | 73 | 74 | 75 | 76 | 77 | 78 | 79 | 80 | 81 | 82 | a | b | c | 83 | 84 | 85 | 86 | 87 | 88 | 89 | 90 | 91 | 92 | 93 | 94 | 95 |
|---|---|---|---|---|---|---|---|---|---|---|---|---|---|---|---|---|---|---|---|---|---|---|---|---|---|---|---|---|---|---|---|---|
| K | A | T | L | N | V | D | R | S | S | N | T | A | Y | M | L | L | S | S | L | T | S | A | D | S | A | V | Y | Y | C | A | T | Y |

| 96 | 97 | 98 | 99 | 100 | a | k | 101 | 102 | 103 | 104 | 105 | 106 | 107 | 108 | 109 | 110 | 111 | 112 | 113 |
|---|---|---|---|---|---|---|---|---|---|---|---|---|---|---|---|---|---|---|---|
| G | S | Y | V | S | P | L | D | Y | W | G | Q | G | T | S | V | T | V | S | S |

(SEQ ID NO: 10)

FIG. 7

5D5.v2 Light Chain

FR1-LC: DIQMTQSPSSLSASVGDRVTITC (SEQ ID NO: 179)
FR2-LC: WYQQKPGKAPKLLIY (SEQ ID NO: 180)
FR3-LC: GVPSRFSGSGSGTDFTLTISSLQPEDFATYYC (SEQ ID NO: 181)
FR4-LC: FGQGTKVEIKR (SEQ ID NO: 182)
HVR1-LC: KSSQSLLYTSSQKNYLA (SEQ ID NO: 183)
HVR2-LC: WASTRES (SEQ ID NO: 184)
HVR3-LC: QQYYAYPWT (SEQ ID NO: 185)
CL1: TVAAPSVFIFPPSDEQLKSGTASVVCLLNNFYPREAKVQWKVDNALQSGNSQESVTEQDSK
DSTYSLSSTLTLSKADYEKHKVYACEVTHQGLSSPVTKSFNRGEC (SEQ ID NO: 186)

5D5.v2 Heavy Chain

FR1-HC: EVQLVESGGGLVQPGGSLRLSCAAS (SEQ ID NO: 187)
FR2-HC: WVRQAPGKGLEWV (SEQ ID NO: 188)
FR3-HC: RFTISADTSKNTAYLQMNSLRAEDTAVYYC (SEQ ID NO: 189)
FR4-HC: WGQGTLVTVSS (SEQ ID NO: 190)
HVR1-HC: GYTFTSYWLH (SEQ ID NO: 191)
HVR2-HC: GMIDPSNSDTRFNPNFKD (SEQ ID NO: 192)
HVR3-HC: ATYRSYVTPLDY (SEQ ID NO: 193)
CH1: ASTKGPSVFPLAPSSKSTSGGTAALGCLVKDYFPEPVTVSWNSGALTSGVHTFPA
VLQSSGLYSLSSVVTVPSSSLGTQTYICNVNHKPSNTKVDKKVEPKSCDKTHT (SEQ ID NO: 194)
CPPCPAPELLGGPSVFLFPPKPKDTLMISRTPEVTCVVVDVSHEDPEVKFNWYVDGVEVH
NAKTKPREEQYNSTYRVVSVLTVLHQDWLNGKEYKCKVSNKALPAPIEKTISKAKGQPREP
QVYTLPPSREEMTKNQVSLSCAVKGFYPSDIAVEWESNGQPENNYKTTPPVLDSDGSFFL
VSKLTVDKSRWQQGNVFSCSVMHEALHNHYTQKSLSLSPGK (SEQ ID NO: 195)

Fc: CPPCPAPELLGGPSVFLFPPKPKDTLMISRTPEVTCVVVDVSHED
PEVKFNWYVDGVEVHNAKTKPREEQYNSTYRVVSVLTVLHQDWLNGKE
YKCKVSNKALPAPIEKTISKAKGQPREPQVYTLPPSREEMTKNQVSLWCL
VKGFYPSDIAVEWESNGQPENNYKTTPPVLDSDGSFFLYSKLTVDKSRW
QQGNVFSCSVMHEALHNHYTQKSLSLSPGK (SEQ ID NO: 196)

*FIG. 13* (covers 5D5.v2 Light Chain and Heavy Chain through CH1)

*FIG. 14* (covers Fc)

SEQUENCE LISTING

```
<160> NUMBER OF SEQ ID NOS: 197

<210> SEQ ID NO 1
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Lys Ser Ser Gln Ser Leu Leu Tyr Thr Ser Ser Gln Lys Asn Tyr Leu
1               5                   10                  15
```

-continued

Ala

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Trp Ala Ser Thr Arg Glu Ser
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln Gln Tyr Tyr Ala Tyr Pro Trp Thr
1               5

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Tyr Thr Phe Thr Ser Tyr Trp Leu His
1               5                   10

<210> SEQ ID NO 5
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Met Ile Asp Pro Ser Asn Ser Asp Thr Arg Phe Asn Pro Asn Phe
1               5                   10                  15

Lys Asp

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid except Arg

<400> SEQUENCE: 6

Xaa Tyr Gly Ser Tyr Val Ser Pro Leu Asp Tyr
1               5                   10

```
<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Thr Tyr Gly Ser Tyr Val Ser Pro Leu Asp Tyr
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ser Tyr Gly Ser Tyr Val Ser Pro Leu Asp Tyr
1               5                   10

<210> SEQ ID NO 9
<211> LENGTH: 114
<212> TYPE: PRT
<213> ORGANISM: Mus musculus

<400> SEQUENCE: 9

Asp Ile Met Met Ser Gln Ser Pro Ser Ser Leu Thr Val Ser Val Gly
1               5                   10                  15

Glu Lys Val Thr Val Ser Cys Lys Ser Gln Ser Leu Leu Tyr Thr
            20                  25                  30

Ser Ser Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Thr Ser Val Lys Ala Asp Asp Leu Ala Val Tyr Tyr Cys Gln Gln
                85                  90                  95

Tyr Tyr Ala Tyr Pro Trp Thr Phe Gly Gly Gly Thr Lys Leu Glu Ile
            100                 105                 110

Lys Arg

<210> SEQ ID NO 10
<211> LENGTH: 119
<212> TYPE: PRT
<213> ORGANISM: Mus musculus

<400> SEQUENCE: 10

Gln Val Gln Leu Gln Gln Ser Gly Pro Glu Leu Val Arg Pro Gly Ala
1               5                   10                  15

Ser Val Lys Met Ser Cys Arg Ala Ser Gly Tyr Thr Phe Thr Ser Tyr
            20                  25                  30

Trp Leu His Trp Val Lys Gln Arg Pro Gly Gln Gly Leu Glu Trp Ile
        35                  40                  45

Gly Met Ile Asp Pro Ser Asn Ser Asp Thr Arg Phe Asn Pro Asn Phe
    50                  55                  60

Lys Asp Lys Ala Thr Leu Asn Val Asp Arg Ser Ser Asn Thr Ala Tyr
```

```
            65                  70                  75                  80
Met Leu Leu Ser Ser Leu Thr Ser Ala Asp Ser Ala Val Tyr Tyr Cys
                85                  90                  95

Ala Thr Tyr Gly Ser Tyr Val Ser Pro Leu Asp Tyr Trp Gly Gln Gly
            100                 105                 110

Thr Ser Val Thr Val Ser Ser
        115

<210> SEQ ID NO 11
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Leu Pro Trp
                85                  90                  95

Thr Phe Gly Gln Gly Thr Lys Val Glu Ile Lys Arg
            100                 105

<210> SEQ ID NO 12
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Tyr Thr
            20                  25                  30

Ser Ser Gln Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Tyr Ala Tyr Pro Trp Thr Phe Gly Gln Gly Thr Lys Val Glu Ile
            100                 105                 110

Lys Arg

<210> SEQ ID NO 13
```

```
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Ile Ser Gly Asp Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Phe Asp Tyr Trp Gly Gln Gly Thr Leu Val Thr Val Ser
            100                 105                 110

Ser

<210> SEQ ID NO 14
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Trp Leu His Trp Val Arg Gln Ala Pro Gly Lys Gly Leu Glu Trp Val
        35                  40                  45

Gly Met Ile Asp Pro Ser Asn Ser Asp Thr Arg Phe Asn Pro Asn Phe
    50                  55                  60

Lys Asp Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Tyr Gly Ser Tyr Val Ser Pro Leu Asp Tyr Trp Gly Gln Gly
            100                 105                 110

Thr Leu Val Thr Val Ser Ser
        115

<210> SEQ ID NO 15
<211> LENGTH: 5
<212> TYPE: PRT
<213> ORGANISM: Homo sapiens

<400> SEQUENCE: 15

Leu Asp Ala Gln Thr
1               5
```

```
<210> SEQ ID NO 16
<211> LENGTH: 9
<212> TYPE: PRT
<213> ORGANISM: Homo sapiens

<400> SEQUENCE: 16

Leu Thr Glu Lys Arg Lys Lys Arg Ser
1               5

<210> SEQ ID NO 17
<211> LENGTH: 8
<212> TYPE: PRT
<213> ORGANISM: Homo sapiens

<400> SEQUENCE: 17

Lys Pro Asp Ser Ala Glu Pro Met
1               5

<210> SEQ ID NO 18
<211> LENGTH: 8
<212> TYPE: PRT
<213> ORGANISM: Homo sapiens

<400> SEQUENCE: 18

Asn Val Arg Cys Leu Gln His Phe
1               5

<210> SEQ ID NO 19
<211> LENGTH: 87
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Trp Val
            20                  25                  30

Arg Gln Ala Pro Gly Gln Gly Leu Glu Trp Met Gly Arg Val Thr Ile
        35                  40                  45

Thr Ala Asp Thr Ser Thr Ser Thr Ala Tyr Met Glu Leu Ser Ser Leu
    50                  55                  60

Arg Ser Glu Asp Thr Ala Val Tyr Tyr Cys Ala Arg Trp Gly Gln Gly
65                  70                  75                  80

Thr Leu Val Thr Val Ser Ser
                85

<210> SEQ ID NO 20
<211> LENGTH: 81
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gln Val Gln Leu Val Gln Ser Gly Ala Glu Val Lys Lys Pro Gly Ala
1               5                   10                  15

Ser Val Lys Val Ser Cys Lys Ala Ser Trp Val Arg Gln Ala Pro Gly
            20                  25                  30

Gln Gly Leu Glu Trp Met Arg Val Thr Ile Thr Ala Asp Thr Ser Thr
```

```
                35                  40                  45
Ser Thr Ala Tyr Met Glu Leu Ser Ser Leu Arg Ser Glu Asp Thr Ala
    50                  55                  60

Val Tyr Tyr Cys Ala Arg Trp Gly Gln Gly Thr Leu Val Thr Val Ser
65                  70                  75                  80

Ser

<210> SEQ ID NO 21
<211> LENGTH: 80
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gln Val Gln Leu Val Gln Ser Gly Ala Glu Val Lys Lys Pro Gly Ala
1               5                   10                  15

Ser Val Lys Val Ser Cys Lys Ala Ser Trp Val Arg Gln Ala Pro Gly
                20                  25                  30

Gln Gly Leu Glu Trp Met Arg Val Thr Ile Thr Ala Asp Thr Ser Thr
            35                  40                  45

Ser Thr Ala Tyr Met Glu Leu Ser Ser Leu Arg Ser Glu Asp Thr Ala
    50                  55                  60

Val Tyr Tyr Cys Ala Trp Gly Gln Gly Thr Leu Val Thr Val Ser Ser
65                  70                  75                  80

<210> SEQ ID NO 22
<211> LENGTH: 79
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gln Val Gln Leu Val Gln Ser Gly Ala Glu Val Lys Lys Pro Gly Ala
1               5                   10                  15

Ser Val Lys Val Ser Cys Lys Ala Ser Trp Val Arg Gln Ala Pro Gly
                20                  25                  30

Gln Gly Leu Glu Trp Met Arg Val Thr Ile Thr Ala Asp Thr Ser Thr
            35                  40                  45

Ser Thr Ala Tyr Met Glu Leu Ser Ser Leu Arg Ser Glu Asp Thr Ala
    50                  55                  60

Val Tyr Tyr Cys Trp Gly Gln Gly Thr Leu Val Thr Val Ser Ser
65                  70                  75

<210> SEQ ID NO 23
<211> LENGTH: 87
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Val Ser Trp Ile
                20                  25                  30
```

```
Arg Gln Pro Pro Gly Lys Gly Leu Glu Trp Ile Gly Arg Val Thr Ile
            35                  40                  45

Ser Val Asp Thr Ser Lys Asn Gln Phe Ser Leu Lys Leu Ser Ser Val
    50                  55                  60

Thr Ala Ala Asp Thr Ala Val Tyr Tyr Cys Ala Arg Trp Gly Gln Gly
65                  70                  75                  80

Thr Leu Val Thr Val Ser Ser
                85

<210> SEQ ID NO 24
<211> LENGTH: 81
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gln Val Gln Leu Gln Glu Ser Gly Pro Gly Leu Val Lys Pro Ser Gln
1               5                   10                  15

Thr Leu Ser Leu Thr Cys Thr Val Ser Trp Ile Arg Gln Pro Pro Gly
            20                  25                  30

Lys Gly Leu Glu Trp Ile Arg Val Thr Ile Ser Val Asp Thr Ser Lys
        35                  40                  45

Asn Gln Phe Ser Leu Lys Leu Ser Ser Val Thr Ala Ala Asp Thr Ala
    50                  55                  60

Val Tyr Tyr Cys Ala Arg Trp Gly Gln Gly Thr Leu Val Thr Val Ser
65                  70                  75                  80

Ser

<210> SEQ ID NO 25
<211> LENGTH: 80
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Val Gln Leu Gln Glu Ser Gly Pro Gly Leu Val Lys Pro Ser Gln
1               5                   10                  15

Thr Leu Ser Leu Thr Cys Thr Val Ser Trp Ile Arg Gln Pro Pro Gly
            20                  25                  30

Lys Gly Leu Glu Trp Ile Arg Val Thr Ile Ser Val Asp Thr Ser Lys
        35                  40                  45

Asn Gln Phe Ser Leu Lys Leu Ser Ser Val Thr Ala Ala Asp Thr Ala
    50                  55                  60

Val Tyr Tyr Cys Ala Trp Gly Gln Gly Thr Leu Val Thr Val Ser Ser
65                  70                  75                  80

<210> SEQ ID NO 26
<211> LENGTH: 79
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gln Val Gln Leu Gln Glu Ser Gly Pro Gly Leu Val Lys Pro Ser Gln
1               5                   10                  15
```

Thr Leu Ser Leu Thr Cys Thr Val Ser Trp Ile Arg Gln Pro Pro Gly
            20                  25                  30

Lys Gly Leu Glu Trp Ile Arg Val Thr Ile Ser Val Asp Thr Ser Lys
        35                  40                  45

Asn Gln Phe Ser Leu Lys Leu Ser Ser Val Thr Ala Ala Asp Thr Ala
    50                  55                  60

Val Tyr Tyr Cys Trp Gly Gln Gly Thr Leu Val Thr Val Ser Ser
65                  70                  75

<210> SEQ ID NO 27
<211> LENGTH: 87
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Trp Val
            20                  25                  30

Arg Gln Ala Pro Gly Lys Gly Leu Glu Trp Val Ser Arg Phe Thr Ile
        35                  40                  45

Ser Arg Asp Asn Ser Lys Asn Thr Leu Tyr Leu Gln Met Asn Ser Leu
    50                  55                  60

Arg Ala Glu Asp Thr Ala Val Tyr Tyr Cys Ala Arg Trp Gly Gln Gly
65                  70                  75                  80

Thr Leu Val Thr Val Ser Ser
                85

<210> SEQ ID NO 28
<211> LENGTH: 81
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Ala Ala Ser Trp Val Arg Gln Ala Pro Gly
            20                  25                  30

Lys Gly Leu Glu Trp Val Arg Phe Thr Ile Ser Arg Asp Asn Ser Lys
        35                  40                  45

Asn Thr Leu Tyr Leu Gln Met Asn Ser Leu Arg Ala Glu Asp Thr Ala
    50                  55                  60

Val Tyr Tyr Cys Ala Arg Trp Gly Gln Gly Thr Leu Val Thr Val Ser
65                  70                  75                  80

Ser

<210> SEQ ID NO 29
<211> LENGTH: 80
<212> TYPE: PRT
<213> ORGANISM: Artificial Sequence
<220> FEATURE:
<223> OTHER INFORMATION: Description of Artificial Sequence: Synthetic
      polypeptide -continued

```
<400> SEQUENCE: 29

Glu Val Gln Leu Val Glu Ser Gly Gly Gly Leu Val Gln Pro Gly Gly
1               5                   10                  15

Ser Leu Arg Leu Ser Cys Ala Ala Ser Trp Val Arg Gln Ala Pro Gly
            20                  25                  30

Lys Gly Leu Glu Trp Val Arg Phe Thr Ile Ser Arg Asp Asn Ser Lys
        35                  40                  45

Asn Thr Leu Tyr Leu Gln Met Asn Ser Leu Arg Ala Glu Asp Thr Ala
    50                  55                  60

Val Tyr Tyr Cys Ala Trp Gly Gln Gly Thr Leu Val Thr Val Ser Ser
65                  70                  75                  80

<210> SEQ ID NO 30
<211> LENGTH: 79
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Ala Ser Trp Val Arg Gln Ala Pro Gly
            20                  25                  30

Lys Gly Leu Glu Trp Val Arg Phe Thr Ile Ser Arg Asp Asn Ser Lys
        35                  40                  45

Asn Thr Leu Tyr Leu Gln Met Asn Ser Leu Arg Ala Glu Asp Thr Ala
    50                  55                  60

Val Tyr Tyr Cys Trp Gly Gln Gly Thr Leu Val Thr Val Ser Ser
65                  70                  75

<210> SEQ ID NO 31
<211> LENGTH: 87
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Trp Val
            20                  25                  30

Arg Gln Ala Pro Gly Lys Gly Leu Glu Trp Val Ser Arg Phe Thr Ile
        35                  40                  45

Ser Ala Asp Thr Ser Lys Asn Thr Ala Tyr Leu Gln Met Asn Ser Leu
    50                  55                  60

Arg Ala Glu Asp Thr Ala Val Tyr Tyr Cys Ser Arg Trp Gly Gln Gly
65                  70                  75                  80

Thr Leu Val Thr Val Ser Ser
                85

<210> SEQ ID NO 32
<211> LENGTH: 81
<212> TYPE: PRT
<213> ORGANISM: Artificial Sequence
<220> FEATURE:
<223> OTHER INFORMATION: Description of Artificial Sequence: Synthetic
```

-continued polypeptide

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Ala Ser Trp Val Arg Gln Ala Pro Gly
            20                  25                  30

Lys Gly Leu Glu Trp Val Arg Phe Thr Ile Ser Ala Asp Thr Ser Lys
        35                  40                  45

Asn Thr Ala Tyr Leu Gln Met Asn Ser Leu Arg Ala Glu Asp Thr Ala
    50                  55                  60

Val Tyr Tyr Cys Ser Arg Trp Gly Gln Gly Thr Leu Val Thr Val Ser
65                  70                  75                  80

Ser

<210> SEQ ID NO 33
<211> LENGTH: 80
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser Trp Val Arg Gln Ala Pro Gly
            20                  25                  30

Lys Gly Leu Glu Trp Val Arg Phe Thr Ile Ser Ala Asp Thr Ser Lys
        35                  40                  45

Asn Thr Ala Tyr Leu Gln Met Asn Ser Leu Arg Ala Glu Asp Thr Ala
    50                  55                  60

Val Tyr Tyr Cys Ser Trp Gly Gln Gly Thr Leu Val Thr Val Ser Ser
65                  70                  75                  80

<210> SEQ ID NO 34
<211> LENGTH: 87
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Trp Val
            20                  25                  30

Arg Gln Ala Pro Gly Lys Gly Leu Glu Trp Val Ser Arg Phe Thr Ile
        35                  40                  45

Ser Ala Asp Thr Ser Lys Asn Thr Ala Tyr Leu Gln Met Asn Ser Leu
    50                  55                  60

Arg Ala Glu Asp Thr Ala Val Tyr Tyr Cys Ala Arg Trp Gly Gln Gly
65                  70                  75                  80

Thr Leu Val Thr Val Ser Ser
                85

<210> SEQ ID NO 35
<211> LENGTH: 81

-continued

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Ala Ala Ser Trp Val Arg Gln Ala Pro Gly
            20                  25                  30

Lys Gly Leu Glu Trp Val Arg Phe Thr Ile Ser Ala Asp Thr Ser Lys
        35                  40                  45

Asn Thr Ala Tyr Leu Gln Met Asn Ser Leu Arg Ala Glu Asp Thr Ala
    50                  55                  60

Val Tyr Tyr Cys Ala Arg Trp Gly Gln Gly Thr Leu Val Thr Val Ser
65                  70                  75                  80

Ser

<210> SEQ ID NO 36
<211> LENGTH: 80
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Glu Val Gln Leu Val Glu Ser Gly Gly Gly Leu Val Gln Pro Gly Gly
1               5                   10                  15

Ser Leu Arg Leu Ser Cys Ala Ala Ser Trp Val Arg Gln Ala Pro Gly
            20                  25                  30

Lys Gly Leu Glu Trp Val Arg Phe Thr Ile Ser Ala Asp Thr Ser Lys
        35                  40                  45

Asn Thr Ala Tyr Leu Gln Met Asn Ser Leu Arg Ala Glu Asp Thr Ala
    50                  55                  60

Val Tyr Tyr Cys Ala Trp Gly Gln Gly Thr Leu Val Thr Val Ser Ser
65                  70                  75                  80

<210> SEQ ID NO 37
<211> LENGTH: 79
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Ala Ala Ser Trp Val Arg Gln Ala Pro Gly
            20                  25                  30

Lys Gly Leu Glu Trp Val Arg Phe Thr Ile Ser Ala Asp Thr Ser Lys
        35                  40                  45

Asn Thr Ala Tyr Leu Gln Met Asn Ser Leu Arg Ala Glu Asp Thr Ala
    50                  55                  60

Val Tyr Tyr Cys Trp Gly Gln Gly Thr Leu Val Thr Val Ser Ser
65                  70                  75

<210> SEQ ID NO 38
```

```
<211> LENGTH: 80
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Trp Tyr Gln Gln Lys Pro Gly Lys Ala
            20                  25                  30

Pro Lys Leu Leu Ile Tyr Gly Val Pro Ser Arg Phe Ser Gly Ser Gly
        35                  40                  45

Ser Gly Thr Asp Phe Thr Leu Thr Ile Ser Ser Leu Gln Pro Glu Asp
    50                  55                  60

Phe Ala Thr Tyr Tyr Cys Phe Gly Gln Gly Thr Lys Val Glu Ile Lys
65                  70                  75                  80

<210> SEQ ID NO 39
<211> LENGTH: 80
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Asp Ile Val Met Thr Gln Ser Pro Leu Ser Leu Pro Val Thr Pro Gly
1               5                   10                  15

Glu Pro Ala Ser Ile Ser Cys Trp Tyr Leu Gln Lys Pro Gly Gln Ser
            20                  25                  30

Pro Gln Leu Leu Ile Tyr Gly Val Pro Asp Arg Phe Ser Gly Ser Gly
        35                  40                  45

Ser Gly Thr Asp Phe Thr Leu Lys Ile Ser Arg Val Glu Ala Glu Asp
    50                  55                  60

Val Gly Val Tyr Tyr Cys Phe Gly Gln Gly Thr Lys Val Glu Ile Lys
65                  70                  75                  80

<210> SEQ ID NO 40
<211> LENGTH: 80
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Glu Ile Val Leu Thr Gln Ser Pro Gly Thr Leu Ser Leu Ser Pro Gly
1               5                   10                  15

Glu Arg Ala Thr Leu Ser Cys Trp Tyr Gln Gln Lys Pro Gly Gln Ala
            20                  25                  30

Pro Arg Leu Leu Ile Tyr Gly Ile Pro Asp Arg Phe Ser Gly Ser Gly
        35                  40                  45

Ser Gly Thr Asp Phe Thr Leu Thr Ile Ser Arg Leu Glu Pro Glu Asp
    50                  55                  60

Phe Ala Val Tyr Tyr Cys Phe Gly Gln Gly Thr Lys Val Glu Ile Lys
65                  70                  75                  80

<210> SEQ ID NO 41
<211> LENGTH: 80
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Asp Ile Val Met Thr Gln Ser Pro Asp Ser Leu Ala Val Ser Leu Gly
1               5                   10                  15

Glu Arg Ala Thr Ile Asn Cys Trp Tyr Gln Gln Lys Pro Gly Gln Pro
            20                  25                  30

Pro Lys Leu Leu Ile Tyr Gly Val Pro Asp Arg Phe Ser Gly Ser Gly
        35                  40                  45

Ser Gly Thr Asp Phe Thr Leu Thr Ile Ser Ser Leu Gln Ala Glu Asp
    50                  55                  60

Val Ala Val Tyr Tyr Cys Phe Gly Gln Gly Thr Lys Val Glu Ile Lys
65                  70                  75                  80

<210> SEQ ID NO 42
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 43
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Trp Val Arg Gln Ala Pro Gly Lys Gly Leu Glu Trp Val
1               5                   10

<210> SEQ ID NO 44
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys
            20                  25                  30

<210> SEQ ID NO 45
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 45

Trp Gly Gln Gly Thr Leu Val Thr Val Ser Ser
1               5                   10

<210> SEQ ID NO 46
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 47
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Trp Tyr Gln Gln Lys Pro Gly Lys Ala Pro Lys Leu Leu Ile Tyr
1               5                   10                  15

<210> SEQ ID NO 48
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 49
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Phe Gly Gln Gly Thr Lys Val Glu Ile Lys
1               5                   10

<210> SEQ ID NO 50
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(6)
```

```
<223> OTHER INFORMATION: Ala or Arg
<220> FEATURE:
<221> NAME/KEY: MOD_RES
<222> LOCATION: (8)..(8)
<223> OTHER INFORMATION: Thr or Asn
<220> FEATURE:
<221> NAME/KEY: MOD_RES
<222> LOCATION: (13)..(13)
<223> OTHER INFORMATION: Ala or Leu

<400> SEQUENCE: 50

Arg Phe Thr Ile Ser Xaa Asp Xaa Ser Lys Asn Thr Xaa Tyr Leu Gln
1               5                   10                  15

Met Asn Ser Leu Arg Ala Glu Asp Thr Ala Val Tyr Tyr Cys
            20                  25                  30

<210> SEQ ID NO 51
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys
            20                  25                  30

<210> SEQ ID NO 52
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Ala
            20                  25                  30

<210> SEQ ID NO 53
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 54
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54
```

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Ser
                20                  25                  30

<210> SEQ ID NO 55
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Ser Arg
                20                  25                  30

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Trp Ala Ser Thr Pro Ala Ser
1               5

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Trp Ala Ser Ile Arg Asp Arg
1               5

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Met Pro Asn Thr Arg Asp Ser
1               5

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Trp Ala Ser Thr Arg Asp Ile
1               5

```
<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Trp Ala Gly Ile Arg Glu Met
1               5

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Leu Ala Ser Asn Arg Glu Gly
1               5

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Trp Thr Gly Asn Arg Glu Met
1               5

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Trp Ala Arg Thr Arg Glu Ser
1               5

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Trp Ala Ser Thr Arg Glu Ser
1               5

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 65

Trp Ala Ser Thr Pro Glu Ser
1               5

<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid

<400> SEQUENCE: 66

Trp Ala Ser Xaa Arg Glu Ser
1               5

<210> SEQ ID NO 67
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Trp Ala Ser Asn Ile Thr Ser
1               5

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Trp Ala Asn Phe Arg Val Ser
1               5

<210> SEQ ID NO 69
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Trp Thr Ser Asn Arg Val Ser
1               5

<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Leu Gly Gly Thr Arg Val Ser
1               5
```

```
<210> SEQ ID NO 71
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Leu Ala Thr Thr Arg Val Ser
1               5

<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Trp Ala Ser Thr Arg Val Ser
1               5

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Trp Ala Ser Thr Leu Val Ser
1               5

<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Trp Ala Ser Thr Gly Val Gly
1               5

<210> SEQ ID NO 75
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Trp Ser Ser Thr Arg Val Ser
1               5

<210> SEQ ID NO 76
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 76

Gly Tyr Asn Phe Ile Gly Phe Trp Met His
1               5                   10

<210> SEQ ID NO 77
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gly Tyr Thr Phe Ile Asp Phe Trp Leu His
1               5                   10

<210> SEQ ID NO 78
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gly Tyr Thr Phe Thr Ser Phe Trp Leu His
1               5                   10

<210> SEQ ID NO 79
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Gly Tyr Thr Phe Thr Ser His Trp Leu His
1               5                   10

<210> SEQ ID NO 80
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gly Tyr Pro Phe Thr Arg Trp Leu His
1               5                   10

<210> SEQ ID NO 81
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gly Tyr Leu Phe Thr Ser Ser Trp Leu His
1               5                   10

<210> SEQ ID NO 82
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Gly Tyr Asn Phe Ser Ser Ser Trp Leu His
1               5                   10

<210> SEQ ID NO 83
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Gly Tyr Pro Phe Thr Lys Ser Trp Leu His
1               5                   10

<210> SEQ ID NO 84
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gly Tyr Ser Phe Thr Thr Ser Trp Val His
1               5                   10

<210> SEQ ID NO 85
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Gly Tyr Thr Phe Thr Asp Ser Trp Leu His
1               5                   10

<210> SEQ ID NO 86
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gly Tyr Thr Phe Ser Ser Ser Trp Leu His
1               5                   10

<210> SEQ ID NO 87
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Gly Tyr Thr Phe Thr Ser Ser Trp Leu His
```

-continued

```
<210> SEQ ID NO 88
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Gly Tyr Ala Phe Thr Ser Thr Trp Leu His
1               5                   10

<210> SEQ ID NO 89
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Gly Tyr Ile Phe Thr Ser Val Trp Leu His
1               5                   10

<210> SEQ ID NO 90
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Gly Tyr Asn Phe Thr Ser Val Trp Leu His
1               5                   10

<210> SEQ ID NO 91
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Gly Tyr Ser Phe Thr Ser Val Trp Leu His
1               5                   10

<210> SEQ ID NO 92
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gly Tyr Thr Phe Thr Arg Val Trp Leu His
1               5                   10

<210> SEQ ID NO 93
<211> LENGTH: 10
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 93

Gly Tyr Ala Phe Thr Ser Tyr Trp Leu His
1               5                   10

<210> SEQ ID NO 94
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Gly Tyr Ile Phe Thr Thr Tyr Trp Leu His
1               5                   10

<210> SEQ ID NO 95
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gly Tyr Thr Phe Thr Ser Tyr Trp Leu His
1               5                   10

<210> SEQ ID NO 96
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Gly Tyr Thr Phe Tyr Ser Tyr Trp Leu His
1               5                   10

<210> SEQ ID NO 97
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gly Met Ile Asp Pro Ser Asn Ser Asp Ile Arg Phe Asn Pro Asp Phe
1               5                   10                  15

Glu Asp

<210> SEQ ID NO 98
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Gly Met Ile Asp Pro Ser Asn Ser Asp Thr Arg Phe Asn Thr Lys Phe
1               5                   10                  15

-continued

Glu Asp

<210> SEQ ID NO 99
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Gly Met Ile Asp Pro Ser Asn Ser Asp Thr Arg Phe Asn Pro Lys Phe
1               5                   10                  15

His Asp

<210> SEQ ID NO 100
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Gly Met Ile Asp Pro Ser Tyr Ser Ile Thr Arg Phe Asn Pro Lys Phe
1               5                   10                  15

Lys Tyr

<210> SEQ ID NO 101
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gly Met Ile Asp Pro Ser Asn Ser Asp Thr Arg Phe Asn Pro Lys Phe
1               5                   10                  15

Asn Tyr

<210> SEQ ID NO 102
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Gly Met Ile Asp Pro Ser Asn Ser Asp Thr Arg Phe Asn Pro Lys Phe
1               5                   10                  15

Asn Asp

<210> SEQ ID NO 103
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Gly Met Ile Asp Pro Ser Asn Ser Asp Thr Arg Phe Asn Pro Lys Phe
1               5                   10                  15

Asn Glu

<210> SEQ ID NO 104
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Gly Met Ile Asp Pro Ser Asn Ser Asp Thr Arg Phe Asn Pro Asn Phe
1               5                   10                  15

Asp Asp

<210> SEQ ID NO 105
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Gly Met Ile Asp Pro Ser Asn Ser Asp Thr Arg Phe Asn Pro Asn Phe
1               5                   10                  15

Glu Asp

<210> SEQ ID NO 106
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Gly Met Ile Asp Pro Ser Asn Ser Asp Thr Arg Phe Asn Gln Asn Phe
1               5                   10                  15

Glu Asp

<210> SEQ ID NO 107
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Gly Met Ile Asp Pro Ser Asn Ser Asp Thr Arg Phe Asn Pro Asn Phe
1               5                   10                  15

Glu His

<210> SEQ ID NO 108
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Gly Met Ile Asp Pro Ser Asn Ser Asp Thr Arg Phe Asn Pro Asn Phe

-continued

```
1               5                  10                 15

Lys Glu

<210> SEQ ID NO 109
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Gly Met Ile Asp Pro Ser Asn Ser Asp Thr Arg Phe Asn Pro Asn Leu
1               5                  10                 15

Gln Asp

<210> SEQ ID NO 110
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Gly Met Ile Asp Pro Ser Asn Ser Asp Thr Arg Phe Asn Pro Ser Leu
1               5                  10                 15

Glu Asp

<210> SEQ ID NO 111
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Gly Met Ile Asp Pro Ser Asn Ser Asp Thr Arg Phe Asn Pro Thr Phe
1               5                  10                 15

Glu Asp

<210> SEQ ID NO 112
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Gly Met Ile Asp Pro Ser Asn Ser Asp Thr Arg Phe Asn Pro Val Leu
1               5                  10                 15

Lys Asp

<210> SEQ ID NO 113
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113
```

```
Ser Tyr Gly Ser Tyr Val Leu Pro Leu Asp Tyr
1               5                   10
```

<210> SEQ ID NO 114
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

```
Ser Tyr Gly Ser Tyr Val Ser Pro Leu Asp Tyr
1               5                   10
```

<210> SEQ ID NO 115
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

```
Ser Tyr Arg Ser Tyr Arg Ile Pro Leu Asp Tyr
1               5                   10
```

<210> SEQ ID NO 116
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

```
Ser Tyr Arg Ser Tyr Val Leu Pro Leu Asp Tyr
1               5                   10
```

<210> SEQ ID NO 117
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

```
Ser Tyr Arg Ser Tyr Val Leu Pro Leu Asp Gln
1               5                   10
```

<210> SEQ ID NO 118
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

```
Ser Tyr Arg Ser Tyr Phe Thr Pro Leu Asp Tyr
1               5                   10
```

<210> SEQ ID NO 119
<211> LENGTH: 11
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 119

Ser Tyr Ser Ser Tyr Met Arg Pro Leu Asp Tyr
1               5                   10

<210> SEQ ID NO 120
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Ser Tyr Ser Ser Tyr Thr Arg Pro Leu Asp Tyr
1               5                   10

<210> SEQ ID NO 121
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Ser Tyr Ser Ser Tyr Val Thr Ser Leu Asp Tyr
1               5                   10

<210> SEQ ID NO 122
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Thr Tyr Gly Ser Tyr Glu Lys Pro Leu Asp Tyr
1               5                   10

<210> SEQ ID NO 123
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Thr Tyr Gly Ser Tyr Val Lys Pro Leu Asp Tyr
1               5                   10

<210> SEQ ID NO 124
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Thr Tyr Gly Ser Tyr Val Arg Pro Leu Asp Tyr
1               5                   10
```

```
<210> SEQ ID NO 125
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Thr Tyr Gly Ser Tyr Val Ser Pro Leu Asp Tyr
1               5                   10

<210> SEQ ID NO 126
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Thr Tyr His Ser Tyr Val Thr Pro Leu Asp Tyr
1               5                   10

<210> SEQ ID NO 127
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Thr Tyr Arg Ser Tyr Val Ser Pro Leu Asp Tyr
1               5                   10

<210> SEQ ID NO 128
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Thr Tyr Arg Ser Tyr Lys Ser Pro Leu Asp Tyr
1               5                   10

<210> SEQ ID NO 129
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Thr Tyr Arg Ser Tyr Phe Thr Pro Leu Tyr Tyr
1               5                   10

<210> SEQ ID NO 130
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130
```

```
Thr Tyr Arg Gly Tyr Glu Thr Pro Leu Asp Tyr
1               5                   10

<210> SEQ ID NO 131
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Thr Tyr Arg Ser Tyr Phe Val Pro Leu Asp Tyr
1               5                   10

<210> SEQ ID NO 132
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Thr Tyr Ser Ser Tyr Val Lys Pro Leu Asp Tyr
1               5                   10

<210> SEQ ID NO 133
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Thr Tyr Ser Ser Tyr Val Arg Pro Leu Asp Tyr
1               5                   10

<210> SEQ ID NO 134
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Thr Tyr Ser Ser Tyr Met Arg Pro Leu Asp Tyr
1               5                   10

<210> SEQ ID NO 135
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Thr Tyr Ser Ser Tyr Met Ser Pro Leu Asp Tyr
1               5                   10

<210> SEQ ID NO 136
<211> LENGTH: 11
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 136

Thr Tyr Ser Ser Tyr Val Thr Ala Leu Asp Tyr
1               5                   10

<210> SEQ ID NO 137
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Thr Tyr Ser Ser Tyr Arg Thr Ala Leu Asp Tyr
1               5                   10

<210> SEQ ID NO 138
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Thr Tyr Thr Ser Tyr Arg Leu Pro Leu Asp Tyr
1               5                   10

<210> SEQ ID NO 139
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Trp Ala Ser Thr Arg Glu Ser
1               5

<210> SEQ ID NO 140
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Gly Tyr Thr Phe Thr Ser Tyr Trp Leu His
1               5                   10

<210> SEQ ID NO 141
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Gly Met Ile Asp Pro Ser Asn Ser Asp Thr Arg Phe Asn Pro Asn Phe
1               5                   10                  15
```

Lys Asp

<210> SEQ ID NO 142
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Ser Tyr Gly Ser Tyr Val Ser Pro Leu Asp Tyr
1               5                   10

<210> SEQ ID NO 143
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Ser Tyr Gly Ser Tyr Val Ser Pro Leu Asp Tyr
1               5                   10

<210> SEQ ID NO 144
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Ser Tyr Arg Ser Tyr Arg Thr Pro Leu Asp Tyr
1               5                   10

<210> SEQ ID NO 145
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Ser Tyr Arg Ser Tyr Val Thr Pro Leu Asp Tyr
1               5                   10

<210> SEQ ID NO 146
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Ser Tyr Arg Ser Tyr Val Val Pro Leu Asp Tyr
1               5                   10

<210> SEQ ID NO 147
<211> LENGTH: 11
<212> TYPE: PRT
<213> ORGANISM: Artificial Sequence
<220> FEATURE:
<223> OTHER INFORMATION: Description of Artificial Sequence: Synthetic -continued peptide

<400> SEQUENCE: 147

Ser Tyr Arg Ser Tyr Val Val Pro Leu Asp Ser
1               5                   10

<210> SEQ ID NO 148
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Ser Tyr Ser Ser Tyr Val Lys Pro Leu Asp Tyr
1               5                   10

<210> SEQ ID NO 149
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Ser Tyr Ser Ser Tyr Val Leu Pro Leu Asp Tyr
1               5                   10

<210> SEQ ID NO 150
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Thr Tyr Ala Ser Tyr Ala Thr Pro Leu Asp Tyr
1               5                   10

<210> SEQ ID NO 151
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Thr Tyr Ala Ser Tyr Val Thr Pro Leu Asp Tyr
1               5                   10

<210> SEQ ID NO 152
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Thr Tyr Gly Ser Tyr Val Thr Ala Leu Asp Tyr
1               5                   10

<210> SEQ ID NO 153

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Thr Tyr Gly Ser Tyr Val Thr Ala Leu Asp His
1               5                   10

<210> SEQ ID NO 154
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Thr Tyr Gly Ser Tyr Met Val Pro Leu Asp Tyr
1               5                   10

<210> SEQ ID NO 155
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Thr Tyr His Ser Tyr Leu Val Pro Leu Asn Tyr
1               5                   10

<210> SEQ ID NO 156
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Thr Tyr Lys Ser Tyr Val Thr Pro Leu Asp Tyr
1               5                   10

<210> SEQ ID NO 157
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Thr Tyr Arg Ser Tyr Arg Ser Pro Leu Asp Tyr
1               5                   10

<210> SEQ ID NO 158
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158
```

```
Thr Tyr Arg Ser Tyr Val Ser Pro Leu Asp Phe
1               5                   10

<210> SEQ ID NO 159
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Thr Tyr Arg Ser Tyr Val Thr Pro Leu Asp Tyr
1               5                   10

<210> SEQ ID NO 160
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Thr Tyr Ser Ser Tyr Trp Ile Pro Leu Asp Tyr
1               5                   10

<210> SEQ ID NO 161
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Thr Tyr Ser Ser Tyr Val Arg Pro Leu Asp Tyr
1               5                   10

<210> SEQ ID NO 162
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Thr Tyr Ser Ser Tyr Val Thr Ser Leu Asp Tyr
1               5                   10

<210> SEQ ID NO 163
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Thr Tyr Ser Ser Tyr Val Thr Ala Leu Asp Tyr
1               5                   10

<210> SEQ ID NO 164
<211> LENGTH: 11
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 164

Ile Tyr Trp Ala Ser Thr Arg Glu Ser Gly Val
1               5                   10

<210> SEQ ID NO 165
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Ile Tyr Trp Ala Ser Thr Arg Val Ser Gly Val
1               5                   10

<210> SEQ ID NO 166
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Ala Ser Gly Tyr Thr Phe Thr Ser Tyr Trp Leu His Trp Val
1               5                   10

<210> SEQ ID NO 167
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Ala Ser Gly Tyr Thr Phe Thr Ser Ser Trp Leu His Trp Val
1               5                   10

<210> SEQ ID NO 168
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Trp Val Gly Met Ile Asp Pro Ser Asn Ser Asp Thr Arg Phe Asn Pro
1               5                   10                  15

Asn Phe Lys Asp Arg Phe
            20

<210> SEQ ID NO 169
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Trp Val Gly Met Ile Asp Pro Ser Asn Ser Asp Thr Arg Phe Asn Thr

```
                1               5                  10                  15

Lys Phe Glu Asp Arg Phe
            20

<210> SEQ ID NO 170
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Trp Val Gly Met Ile Asp Pro Ser Asn Ser Asp Thr Arg Phe Asn Pro
1               5                  10                  15

Asn Phe Glu Asp Arg Phe
            20

<210> SEQ ID NO 171
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Cys Ala Arg Tyr Gly Ser Tyr Val Ser Pro Leu Asp Tyr Trp Gly
1               5                  10                  15

<210> SEQ ID NO 172
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Cys Ala Ser Tyr Gly Ser Tyr Val Ser Pro Leu Asp Tyr Trp Gly
1               5                  10                  15

<210> SEQ ID NO 173
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Cys Ala Thr Tyr Gly Ser Tyr Val Ser Pro Leu Asp Tyr Trp Gly
1               5                  10                  15

<210> SEQ ID NO 174
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Cys Ala Thr Tyr Arg Ser Tyr Val Ser Pro Leu Asp Tyr Trp Gly
1               5                  10                  15
```

<210> SEQ ID NO 175
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Cys Ala Ser Tyr Arg Ser Tyr Val Thr Pro Leu Asp Tyr Trp Gly
1               5                   10                  15

<210> SEQ ID NO 176
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Cys Ala Thr Tyr Arg Ser Tyr Val Thr Pro Leu Asp Tyr Trp Gly
1               5                   10                  15

<210> SEQ ID NO 177
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Cys Ala Thr Tyr Ser Ser Tyr Val Thr Ser Leu Asp Tyr Trp Gly
1               5                   10                  15

<210> SEQ ID NO 178
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Cys Ala Thr Tyr Ser Ser Tyr Val Thr Ala Leu Asp Tyr Trp Gly
1               5                   10                  15

<210> SEQ ID NO 179
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 180
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 180

Trp Tyr Gln Gln Lys Pro Gly Lys Ala Pro Lys Leu Leu Ile Tyr
1               5                   10                  15

<210> SEQ ID NO 181
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 182
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Phe Gly Gln Gly Thr Lys Val Glu Ile Lys Arg
1               5                   10

<210> SEQ ID NO 183
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Lys Ser Ser Gln Ser Leu Leu Tyr Thr Ser Ser Gln Lys Asn Tyr Leu
1               5                   10                  15

Ala

<210> SEQ ID NO 184
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Trp Ala Ser Thr Arg Glu Ser
1               5

<210> SEQ ID NO 185
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

```
Gln Gln Tyr Tyr Ala Tyr Pro Trp Thr
1               5
```

<210> SEQ ID NO 186
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

```
Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105
```

<210> SEQ ID NO 187
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

```
Glu Val Gln Leu Val Glu Ser Gly Gly Gly Leu Val Gln Pro Gly Gly
1               5                   10                  15

Ser Leu Arg Leu Ser Cys Ala Ala Ser
            20                  25
```

<210> SEQ ID NO 188
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

```
Trp Val Arg Gln Ala Pro Gly Lys Gly Leu Glu Trp Val
1               5                   10
```

<210> SEQ ID NO 189
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

```
Arg Phe Thr Ile Ser Ala Asp Thr Ser Lys Asn Thr Ala Tyr Leu Gln
1               5                   10                  15
```

-continued

```
Met Asn Ser Leu Arg Ala Glu Asp Thr Ala Val Tyr Tyr Cys
            20                  25                  30

<210> SEQ ID NO 190
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Trp Gly Gln Gly Thr Leu Val Thr Val Ser Ser
1               5                   10

<210> SEQ ID NO 191
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Gly Tyr Thr Phe Thr Ser Tyr Trp Leu His
1               5                   10

<210> SEQ ID NO 192
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Gly Met Ile Asp Pro Ser Asn Ser Asp Thr Arg Phe Asn Pro Asn Phe
1               5                   10                  15

Lys Asp

<210> SEQ ID NO 193
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Ala Thr Tyr Arg Ser Tyr Val Thr Pro Leu Asp Tyr
1               5                   10

<210> SEQ ID NO 194
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

```
Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr
            100                 105

<210> SEQ ID NO 195
<211> LENGTH: 222
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

Cys Pro Pro Cys Pro Ala Pro Glu Leu Leu Gly Gly Pro Ser Val Phe
  1               5                  10                  15

Leu Phe Pro Pro Lys Pro Lys Asp Thr Leu Met Ile Ser Arg Thr Pro
             20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
    50                  55                  60

Lys Pro Arg Glu Glu Gln Tyr Asn Ser Thr Tyr Arg Val Val Ser Val
 65                  70                  75                  80

Leu Thr Val Leu His Gln Asp Trp Leu Asn Gly Lys Glu Tyr Lys Cys
                 85                  90                  95

Lys Val Ser Asn Lys Ala Leu Pro Ala Pro Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Arg Glu Glu Met Thr Lys Asn Gln Val Ser Leu Ser Cys Ala Val
130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Val Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn His Tyr Thr Gln Lys Ser Leu Ser Leu Ser Pro Gly Lys
    210                 215                 220

<210> SEQ ID NO 196
<211> LENGTH: 222
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196
```

```
Cys Pro Pro Cys Pro Ala Pro Glu Leu Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
    50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
                100                 105                 110

Lys Ala Lys Gly Gln Pro Arg Glu Pro Gln Val Tyr Thr Leu Pro Pro
            115                 120                 125

Ser Arg Glu Glu Met Thr Lys Asn Gln Val Ser Leu Trp Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
            195                 200                 205

Asn His Tyr Thr Gln Lys Ser Leu Ser Leu Ser Pro Gly Lys
    210                 215                 220

<210> SEQ ID NO 197
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (98)..(98)
<223> OTHER INFORMATION: Ser or Thr
<220> FEATURE:
<221> NAME/KEY: MOD_RES
<222> LOCATION: (100)..(100)
<223> OTHER INFORMATION: Arg or Ser
<220> FEATURE:
<221> NAME/KEY: MOD_RES
<222> LOCATION: (104)..(104)
<223> OTHER INFORMATION: Thr or Ser
<220> FEATURE:
<221> NAME/KEY: MOD_RES
<222> LOCATION: (105)..(105)
<223> OTHER INFORMATION: Pro, Ser or Ala

<400> SEQUENCE: 197

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Trp Leu His Trp Val Arg Gln Ala Pro Gly Lys Gly Leu Glu Trp Val
        35                  40                  45

Gly Met Ile Asp Pro Ser Asn Ser Asp Thr Arg Phe Asn Pro Asn Phe
```

-continued

```
                 50                   55                   60
Lys Asp Arg Phe Thr Ile Ser Ala Asp Thr Ser Lys Asn Thr Ala Tyr
 65              70                   75                   80

Leu Gln Met Asn Ser Leu Arg Ala Glu Asp Thr Ala Val Tyr Tyr Cys
             85                   90                   95

Ala Xaa Tyr Xaa Ser Tyr Val Xaa Xaa Leu Asp Tyr Trp Gly Gln Gly
            100                 105                 110

Thr Leu Val Thr Val Ser Ser
            115
```

ANTI-CMET ANTIBODIES

RELATED APPLICATIONS

This application is a continuation application of Ser. No. 11/196,917 filed on Aug. 4, 2005 which application claims priority to provisional application No. 60/598,991 filed Aug. 5, 2004, the contents of which are incorporated herein in their entirety by reference.

REFERENCE TO A COMPUTER PROGRAM LISTING APPENDIX SUBMITTED ON A COMPACT DISC

This application is accompanied by a computer program listing appendix submission on a compact disc (in duplicate copies) which contains the file titled "Computer_Program_Appendix_Table_A.txt", created on Dec. 3, 2010, that is 163,328 bytes in size, the contents of which are incorporated in their entirety herein by reference. The computer program listing appendix contains the computer program of originally filed Table A.

TECHNICAL FIELD

The present invention relates generally to the fields of molecular biology and growth factor regulation. More specifically, the invention concerns modulators of the HGF/c-met signaling pathway, and uses of said modulators.

BACKGROUND

HGF is a mesenchyme-derived pleiotrophic factor with mitogenic, motogenic and morphogenic activities on a number of different cell types. HGF effects are mediated through a specific tyrosine kinase, c-met, and aberrant HGF and c-met expression are frequently observed in a variety of tumors. See, e.g., Maulik et al., Cytokine & Growth Factor Reviews (2002), 13:41-59; Danilkovitch-Miagkova & Zbar, J. Clin. Invest. (2002), 109(7):863-867. Regulation of the HGF/c-Met signaling pathway is implicated in tumor progression and metastasis. See, e.g., Trusolino & Comoglio, Nature Rev. (2002), 2:289-300).

HGF binds the extracellular domain of the Met receptor tyrosine kinase (RTK) and regulates diverse biological processes such as cell scattering, proliferation, and survival. HGF-Met signaling is essential for normal embryonic development especially in migration of muscle progenitor cells and development of the liver and nervous system (Bladt et al., 1995; Hamanoue et al., 1996; Maina et al., 1996; Schmidt et al., 1995; Uehara et al., 1995). Developmental phenotypes of Met and HGF knockout mice are very similar suggesting that HGF is the cognate ligand for the Met receptor (Schmidt et al., 1995; Uehara et al., 1995). HGF-Met also plays a role in liver regeneration, angiogenesis, and wound healing (Bussolino et al., 1992; Matsumoto and Nakamura, 1993; Nusrat et al., 1994). The precursor Met receptor undergoes proteolytic cleavage into an extracellular α subunit and membrane spanning β subunit linked by disulfide bonds (Tempest et al., 1988). The β subunit contains the cytoplasmic kinase domain and harbors a multi-substrate docking site at the C-terminus where adapter proteins bind and initiate signaling (Bardelli et al., 1997; Nguyen et al., 1997; Pelicci et al., 1995; Ponzetto et al., 1994; Weidner et al., 1996). Upon HGF binding, activation of Met leads to tyrosine phosphorylation and downstream signaling through Gab1 and Grb2/Sos mediated PI3-kinase and Ras/MAPK activation respectively, which drives cell motility and proliferation (Furge et al., 2000; Hartmann et al., 1994; Ponzetto et al., 1996; Royal and Park, 1995).

Met was shown to be transforming in a carcinogen-treated osteosarcoma cell line (Cooper et al., 1984; Park et al., 1986). Met overexpression or gene-amplification has been observed in a variety of human cancers. For example, Met protein is overexpressed at least 5-fold in colorectal cancers and reported to be gene-amplified in liver metastasis (Di Renzo et al., 1995; Liu et al., 1992). Met protein is also reported to be overexpressed in oral squamous cell carcinoma, hepatocellular carcinoma, renal cell carcinoma, breast carcinoma, and lung carcinoma (Jin et al., 1997; Morello et al., 2001; Natali et al., 1996; Olivero et al., 1996; Suzuki et al., 1994). In addition, overexpression of mRNA has been observed in hepatocellular carcinoma, gastric carcinoma, and colorectal carcinoma (Boix et al., 1994; Kuniyasu et al., 1993; Liu et al., 1992).

A number of mutations in the kinase domain of Met have been found in renal papillary carcinoma which leads to constitutive receptor activation (Olivero et al., 1999; Schmidt et al., 1997; Schmidt et al., 1999). These activating mutations confer constitutive Met tyrosine phosphorylation and result in MAPK activation, focus formation, and tumorigenesis (Jeffers et al., 1997). In addition, these mutations enhance cell motility and invasion (Giordano et al., 2000; Lorenzato et al., 2002). HGF-dependent Met activation in transformed cells mediates increased motility, scattering, and migration which eventually leads to invasive tumor growth and metastasis (Jeffers et al., 1996; Meiners et al., 1998).

Met has been shown to interact with other proteins that drive receptor activation, transformation, and invasion. In neoplastic cells, Met is reported to interact with α6β4 integrin, a receptor for extracellular matrix (ECM) components such as laminins, to promote HGF-dependent invasive growth (Trusolino et al., 2001). In addition, the extracellular domain of Met has been shown to interact with a member of the semaphorin family, plexin B1, and to enhance invasive growth (Giordano et al., 2002). Furthermore, CD44v6, which has been implicated in tumorigenesis and metastasis, is also reported to form a complex with Met and HGF and result in Met receptor activation (Orian-Rousseau et al., 2002).

Met is a member of the subfamily of RTKs which include Ron and Sea (Maulik et al., 2002). Prediction of the extracellular domain structure of Met suggests shared homology with the semaphorins and plexins. The N-terminus of Met contains a Sema domain of approximately 500 amino acids that is conserved in all semaphorins and plexins. The semaphorins and plexins belong to a large family of secreted and membrane-bound proteins first described for their role in neural development (Van Vactor and Lorenz, 1999). However, more recently semaphorin overexpression has been correlated with tumor invasion and metastasis. A cysteine-rich PSI domain (also referred to as a Met Related Sequence domain) found in plexins, semaphorins, and integrins lies adjacent to the Sema domain followed by four IPT repeats that are immunoglobulin-like regions found in plexins and transcription factors. A recent study suggests that the Met Sema domain is sufficient for HGF and heparin binding (Gherardi et al., 2003). Furthermore, Kong-Beltran et al. (Cancer Cell (2004), 6:61-73) have reported that the Sema domain of Met is necessary for receptor dimerization and activation.

Numerous molecules targeted at the HGF/c-met pathway have been reported. These molecules include antibodies such as those described in U.S. Pat. No. 5,686,292. A portion of the extracellular domain of c-met has also been shown to be capable of antagonistic effects against the HGF/c-met pathway. In view of the important role that this pathway plays in the etiology of various pathological conditions, however, it is clear that there continues to be a need for agents that have clinical attributes that are optimal for development as therapeutic agents. The invention described herein meets this need and provides other benefits.

All references cited herein, including patent applications and publications, are incorporated by reference in their entirety.

DISCLOSURE OF THE INVENTION

The invention is in part based on the identification of a variety of antagonists of the HGF/c-met biological pathway, which is a biological/cellular process that presents as an important and advantageous therapeutic target. The invention provides compositions and methods based on interfering with HGF/c-met activation, including but not limited to interfering with HGF binding to the extracellular portion of c-met and receptor multimerization. Antagonists of the invention, as described herein, provide important therapeutic and diagnostic agents for use in targeting pathological conditions associated with abnormal or unwanted signaling of the HGF/c-met pathway. Accordingly, the invention provides methods, compositions, kits and articles of manufacture related to modulating the HGF/c-met pathway, including modulation of c-met ligand binding, c-met dimerization, activation, and other biological/physiological activities associated with HGF/c-met signaling.

In one aspect, the invention provides anti-HGF/c-met therapeutic agents suitable for therapeutic use and capable of effecting varying degrees of disruption of the HGF/c-met signaling pathway. For example, in one embodiment, the invention provides a humanized anti-c-met antibody wherein the monovalent affinity of the antibody to human c-met (e.g., affinity of the antibody as a Fab fragment to human c-met) is substantially the same as the monovalent affinity of a murine antibody (e.g., affinity of the murine antibody as a Fab fragment to human c-met) comprising, consisting or consisting essentially of a light chain and heavy chain variable domain sequence as depicted in FIG. 7 (SEQ ID NO:9 and 10). In another embodiment, the invention provides a humanized anti-c-met antibody wherein the monovalent affinity of the antibody to human c-met (e.g., affinity of the antibody as a Fab fragment to human c-met) is lower, for example at least 3, 5, 7 or 10-fold lower, than the monovalent affinity of a murine antibody (e.g., affinity of the murine antibody as a Fab fragment to human c-met) comprising, consisting or consisting essentially of a light chain and heavy chain variable domain sequence as depicted in FIG. 7 (SEQ ID NO: 9 and 10). In another embodiment, the invention provides an anti-c-met humanized antibody wherein the monovalent affinity of the antibody to human c-met (e.g., affinity of the antibody as a Fab fragment to human c-met) is greater, for example at least 3, 5, 7, 10 or 13-fold greater, than the monovalent affinity of a murine antibody (e.g., affinity of the murine antibody as a Fab fragment to human c-met) comprising, consisting or consisting essentially of a light chain and heavy chain variable domain sequence as depicted in FIG. 7 (SEQ ID NO: 9 and 10). In one embodiment, the monovalent affinity of the murine antibody to human c-met is substantially the same as the binding affinity of a Fab fragment comprising variable domain sequences of an antibody produced by hybridoma cell line deposited under American Type Culture Collection Accession Number ATCC HB-11894 (hybridoma 1A3.3.13) or HB-11895 (hybridoma 5D5.11.6). As is well-established in the art, binding affinity of a ligand to its receptor can be determined using any of a variety of assays, and expressed in terms of a variety of quantitative values. Accordingly, in one embodiment, the binding affinity is expressed as Kd values and reflects intrinsic binding affinity (e.g., with minimized avidity effects). Generally and preferably, binding affinity is measured in vitro, whether in a cell-free or cell-associated setting. As described in greater detail herein, fold difference in binding affinity can be quantified in terms of the ratio of the monovalent binding affinity value of a humanized antibody (e.g., in Fab form) and the monovalent binding affinity value of a reference/comparator antibody (e.g., in Fab form) (e.g., a murine antibody having donor hypervariable region sequences), wherein the binding affinity values are determined under similar assay conditions. Thus, in one embodiment, the fold difference in binding affinity is determined as the ratio of the Kd values of the humanized antibody in Fab form and said reference/comparator Fab antibody. For example, in one embodiment, if an antibody of the invention (A) has an affinity that is "3-fold lower" than the affinity of a reference antibody (M), then if the Kd value for A is 3×, the Kd value of M would be 1×, and the ratio of Kd of A to Kd of M would be 3:1. Conversely, in one embodiment, if an antibody of the invention (C) has an affinity that is "3-fold greater" than the affinity of a reference antibody (R), then if the Kd value for C is 1×, the Kd value of R would be 3×, and the ratio of Kd of C to Kd of R would be 1:3. Any of a number of assays known in the art, including those described herein, can be used to obtain binding affinity measurements, including, for example, Biacore, radioimmunoassay (RIA) and ELISA.

In one aspect, a HGF/c-met antagonist of the invention comprises an anti-c-met antibody comprising:

(a) at least one, two, three, four or five hypervariable region (HVR) sequences selected from the group consisting of:

(i) HVR-L1 comprising sequence A1-A17, wherein A1-A17 is KSSQSLLYTSSQKNYLA (SEQ ID NO:1)

(ii) HVR-L2 comprising sequence B1-B7, wherein B1-B7 is WASTRES (SEQ ID NO:2)

(iii) HVR-L3 comprising sequence C1-C9, wherein C1-C9 is QQYYAYPWT (SEQ ID NO:3)

(iv) HVR-H1 comprising sequence D1-D10, wherein D1-D10 is GYTFTSYWLH (SEQ ID NO:4)

(v) HVR-H2 comprising sequence E1-E18, wherein E1-E18 is GMIDPSNSDTRFNPNFKD (SEQ ID NO:5) and (vi) HVR-H3 comprising sequence F1-F11, wherein F1-F11 is XYGSYVSPLDY (SEQ ID NO:6) and X is not R;

and (b) at least one variant HVR, wherein the variant HVR sequence comprises modification of at least one residue of the sequence depicted in SEQ ID NOs:1, 2, 3, 4, 5 or 6. In one embodiment, HVR-L1 of an antibody of the invention comprises the sequence of SEQ ID NO: 1. In one embodiment, HVR-L2 of an antibody of the invention comprises the sequence of SEQ ID NO:2. In one embodiment, HVR-L3 of an antibody of the invention comprises the sequence of SEQ ID NO:3. In one embodiment, HVR-H1 of an antibody of the invention comprises the sequence of SEQ ID NO:4. In one embodiment, HVR-H2 of an antibody of the invention comprises the sequence of SEQ ID NO:5. In one embodiment, HVR-H3 of an antibody of the invention comprises the sequence of SEQ ID NO:6. In one embodiment, HVR-H3 comprises TYGSYVSPLDY (SEQ ID NO: 7). In one embodiment, HVR-H3 comprises SYGSYVSPLDY (SEQ ID NO: 8). In one embodiment, an antibody of the invention comprising these sequences (in combination as described herein) is humanized or human.

In one aspect, the invention provides an antibody comprising one, two, three, four, five or six HVRs, wherein each HVR comprises, consists or consists essentially of a sequence selected from the group consisting of SEQ ID NOs: 1, 2, 3, 4, 5, 6, 7, and 8, and wherein SEQ ID NO:1 corresponds to an HVR-L1, SEQ ID NO:2 corresponds to an HVR-L2, SEQ ID NO:3 corresponds to an HVR-L3, SEQ ID NO:4 corresponds to an HVR-H1, SEQ ID NO:5 corresponds to an HVR-H2, and SEQ ID NOs:6, 7 or 8 corresponds to an HVR-H3. In one embodiment, an antibody of the invention comprises HVR-L1, HVR-L2, HVR-L3, HVR-H1, HVR-H2, and HVR-H3, wherein each, in order, comprises SEQ ID NO:1, 2, 3, 4, 5 and 7. In one embodiment, an antibody of the invention comprises HVR-L1, HVR-L2, HVR-L3, HVR-H1, HVR-H2, and HVR-H3, wherein each, in order, comprises SEQ ID NO:1, 2, 3, 4, 5 and 8.

Variant HVRs in an antibody of the invention can have modifications of one or more residues within the HVR. In one embodiment, a HVR-L2 variant comprises 1-5 (1, 2, 3, 4 or 5) substitutions in any combination of the following positions: B1 (M or L), B2 (P, T, G or S), B3 (N, G, R or T), B4 (I, N or F), B5 (P, I, L or G), B6 (A, D, T or V) and B7 (R, I, M or G). In one embodiment, a HVR-H1 variant comprises 1-5 (1, 2, 3, 4 or 5) substitutions in any combination of the following positions: D3 (N, P, L, S, A, I), D5 (I, S or Y), D6 (G, D, T, K, R), D7 (F, H, R, S, T or V) and D9 (M or V). In one embodiment, a HVR-H2 variant comprises 1-4 (1,2, 3 or 4) substitutions in any combination of the following positions: E7 (Y), E9 (I), E10 (I), E14 (T or Q), E15 (D, K, S, T or V), E16 (L), E17 (E, H, N or D) and E18 (Y, E or H). In one embodiment, a HVR-H3 variant comprises 1-5 (1, 2, 3, 4 or 5) substitutions in any combination of the following positions: F1 (T, S), F3 (R, S, H, T, A, K), F4 (G), F6 (R, F, M, T, E, K, A, L, W), F7 (L, I, T, R, K, V), F8 (S, A), F10 (Y, N) and F11 (Q, S, H, F). Letter(s) in parenthesis following each position indicates an illustrative substitution (i.e., replacement) amino acid; as would be evident to one skilled in the art, suitability of other amino acids as substitution amino acids in the context described herein can be routinely assessed using techniques known in the art and/or described herein. In one embodiment, a HVR-L1 comprises the sequence of SEQ ID NO:1. In one embodiment, F1 in a variant HVR-H3 is T. In one embodiment, F1 in a variant HVR-H3 is S. In one embodiment, F3 in a variant HVR-H3 is R. In one embodiment, F3 in a variant HVR-H3 is S. In one embodiment, F7 in a variant HVR-H3 is T. In one embodiment, an antibody of the invention comprises a variant HVR-H3 wherein F1 is T or S, F3 is R or S, and F7 is T.

In one embodiment, an antibody of the invention comprises a variant HVR-H3 wherein F1 is T, F3 is R and F7 is T. In one embodiment, an antibody of the invention comprises a variant HVR-H3 wherein F1 is S. In one embodiment, an antibody of the invention comprises a variant HVR-H3 wherein F1 is T, and F3 is R. In one embodiment, an antibody of the invention comprises a variant HVR-H3 wherein F1 is S, F3 is R and F7 is T. In one embodiment, an antibody of the invention comprises a variant HVR-H3 wherein F1 is T, F3 is S, F7 is T, and F8 is S. In one embodiment, an antibody of the invention comprises a variant HVR-H3 wherein F1 is T, F3 is S, F7 is T, and F8 is A. In some embodiments, said variant HVR-H3 antibody further comprises HVR-L1, HVR-L2, HVR-L3, HVR-H1 and HVR-H2 wherein each comprises, in order, the sequence depicted in SEQ ID NOs: 1, 2, 3, 4 and 5. In some embodiments, these antibodies further comprise a human subgroup III heavy chain framework consensus sequence. In one embodiment of these antibodies, the framework consensus sequence comprises substitution at position 71, 73 and/or 78. In some embodiments of these antibodies, position 71 is A, 73 is T and/or 78 is A. In one embodiment of these antibodies, these antibodies further comprise a human κI light chain framework consensus sequence.

In one embodiment, an antibody of the invention comprises a variant HVR-L2 wherein B6 is V. In some embodiments, said variant HVR-L2 antibody further comprises HVR-L1, HVR-L3, HVR-H1, HVR-H2 and HVR-H3, wherein each comprises, in order, the sequence depicted in SEQ ID NOs:1, 3, 4, 5 and 6. In some embodiments, said variant HVR-L2 antibody further comprises HVR-L1, HVR-L3, HVR-H1, HVR-H2 and HVR-H3, wherein each comprises, in order, the sequence depicted in SEQ ID NOs:1, 3, 4, 5 and 7. In some embodiments, said variant HVR-L2 antibody further comprises HVR-L1, HVR-L3, HVR-H1, HVR-112 and HVR-H3, wherein each comprises, in order, the sequence depicted in SEQ ID NOs:1, 3, 4, 5 and 8. In some embodiments, these antibodies further comprise a human subgroup III heavy chain framework consensus sequence. In one embodiment of these antibodies, the framework consensus sequence comprises substitution at position 71, 73 and/or 78. In some embodiments of these antibodies, position 71 is A, 73 is T and/or 78 is A. In one embodiment of these antibodies, these antibodies further comprise a human κI light chain framework consensus sequence.

In one embodiment, an antibody of the invention comprises a variant HVR-H2 wherein E14 is T, E15 is K and E17 is E. In one embodiment, an antibody of the invention comprises a variant HVR-H2 wherein E17 is E. In some embodiments, said variant HVR-H3 antibody further comprises HVR-L1, HVR-L2, HVR-L3, HVR-H1, and HVR-H3 wherein each comprises, in order, the sequence depicted in SEQ ID NOs:1, 2, 3, 4 and 6. In some embodiments, said variant HVR-H2 antibody further comprises HVR-L1, HVR-L2, HVR-L3, HVR-H1, and HVR-H3, wherein each comprises, in order, the sequence depicted in SEQ ID NOs:1, 2, 3, 4, and 7. In some embodiments, said variant HVR-H2 antibody further comprises HVR-L1, HVR-L2, HVR-L3, HVR-H1, and HVR-H3, wherein each comprises, in order, the sequence depicted in SEQ ID NOs:1, 2, 3, 4, and 8. In some embodiments, these antibodies further comprise a human subgroup III heavy chain framework consensus sequence. In one embodiment of these antibodies, the framework consensus sequence comprises substitution at position 71, 73 and/or 78. In some embodiments of these antibodies, position 71 is A, 73 is T and/or 78 is A. In one embodiment of these antibodies, these antibodies further comprise a human κI light chain framework consensus sequence.

In one aspect, the invention provides an antibody comprising one, two, three, four, five or all of the HVR sequences depicted in FIGS. 2, 3 and/or 4 (SEQ ID NOs:56-163).

A therapeutic agent for use in a host subject preferably elicits little to no immunogenic response against the agent in said subject. In one embodiment, the invention provides such an agent. For example, in one embodiment, the invention provides a humanized antibody that elicits and/or is expected to elicit a human anti-mouse antibody response (HAMA) at a substantially reduced level compared to an antibody comprising the sequence of SEQ ID NO: 9 & 10 in a host subject. In another example, the invention provides a humanized antibody that elicits and/or is expected to elicit minimal or no human anti-mouse antibody response (HAMA). In one example, an antibody of the invention elicits anti-mouse antibody response that is at or less than a clinically-acceptable level.

A humanized antibody of the invention may comprise one or more human and/or human consensus non-hypervariable region (e.g., framework) sequences in its heavy and/or light chain variable domain. In some embodiments, one or more additional modifications are present within the human and/or human consensus non-hypervariable region sequences. In one embodiment, the heavy chain variable domain of an antibody of the invention comprises a human consensus framework sequence, which in one embodiment is the subgroup III consensus framework sequence. In one embodiment, an antibody of the invention comprises a variant subgroup III consensus framework sequence modified at least one amino acid position. For example, in one embodiment, a variant subgroup III consensus framework sequence may comprise a substitution at one or more of positions 71, 73 and/or 78. In one embodiment, said substitution is R71A, N73T and/or N78A, in any combination thereof.

As is known in the art, and as described in greater detail hereinbelow, the amino acid position/boundary delineating a hypervariable region of an antibody can vary, depending on the context and the various definitions known in the art (as described below). Some positions within a variable domain may be viewed as hybrid hypervariable positions in that these positions can be deemed to be within a hypervariable region under one set of criteria while being deemed to be outside a hypervariable region under a different set of criteria. One or more of these positions can also be found in extended hypervariable regions (as further defined below). The invention provides antibodies comprising modifications in these hybrid hypervariable positions. In one embodiment, these hybrid hypervariable positions include one or more of positions 26-30, 33-35B, 47-49, 57-65, 93, 94 and 102 in a heavy chain variable domain. In one embodiment, these hybrid hypervariable positions include one or more of positions 24-29, 35-36, 46-49, 56 and 97 in a light chain variable domain. In one embodiment, an antibody of the invention comprises a variant human subgroup consensus framework sequence modified at one or more hybrid hypervariable positions. In one embodiment, an antibody of the invention comprises a heavy chain variable domain comprising a variant human subgroup III consensus framework sequence modified at one or more of positions 27-28, 30, 33-35, 49, 57-65, 94 and 102. In one embodiment, the antibody comprises a F27Y substitution. In one embodiment, the antibody comprises a T28N, P, L, S, A or I substitution. In one embodiment, the antibody comprises a S30I, T or Y substitution. In one embodiment, the antibody comprises a A33W substitution. In one embodiment, the antibody comprises a M34L or M34V substitution. In one embodiment, the antibody comprises a S35H substitution. In one embodiment, the antibody comprises a T57I substitution. In one embodiment, the antibody comprises a Y58R substitution. In one embodiment, the antibody comprises a Y59F substitution. In one embodiment, the antibody comprises a A60N substitution. In one embodiment, the antibody comprises a D61P, T or Q substitution. In one embodiment, the antibody comprises a S62N, D, K, T or V substitution. In one embodiment, the antibody comprises a V63F or V63L substitution. In one embodiment, the antibody comprises a K64E, H, N, D or Q substitution. In one embodiment, the antibody comprises a G65D, Y, E or H substitution. In one embodiment, the antibody comprises a R94T or R94S substitution. In one embodiment, the antibody comprises a Y102Q, S, H or F substitution. In one embodiment, an antibody of the invention comprising said R94T or R94S modification further comprises one or more modifications at position 96 and/or 100. In one embodiment, said modifications comprise a G96R and/or S100T substitution (i.e., in HVR-H3). In one embodiment, an antibody of the invention comprises a light chain variable domain comprising a variant human kappa subgroup I consensus framework sequence modified at one or more of positions 24, 25, 29 and 56. In one embodiment, the antibody comprises a R24K substitution. In one embodiment, the antibody comprises a A25S substitution. In one embodiment, the antibody comprises a I29Q substitution. In one embodiment, the antibody comprises a S56R, I, M or G substitution.

In one embodiment, an antibody of the invention comprises a heavy chain variable domain comprising a variant human subgroup III consensus framework sequence modified at 1, 2, 3, 4, 5, 6, 7, 8, 9, 10, 11, 12, 13, 14, 15, 16, 17 or all of positions 27-28, 30, 33-35, 49, 57-65, 94 and 102. In one embodiment, modification is selected from the group consisting of F27Y, T28(N, P, L, S, A or I), S30(I, T or Y), A33W, M34(L, V), S35H, T57I, Y58R, Y59F, A60N, D61(P, T, Q), S62(N, D, K, T, V), V63(F, L), K64(E, H, N, D, Q), G65(D, Y, E, H), R94(T, S) and Y102(Q, S, H, F). In one embodiment, an antibody of the invention comprising said R94T or R94S modification further comprises one or more modifications at position 96 and/or 100. In one embodiment, said modifications comprise a G96R and/or S100T substitution (i.e., in HVR-H3).

In one embodiment, an antibody of the invention comprises a light chain variable domain comprising a variant human kappa subgroup I consensus framework sequence modified at 1, 2, 3 or all of positions 24, 25, 29 and 56. In one embodiment, modification is selected from the group consisting of R24K, A25S, I29Q and S56(R, I, M, G).

An antibody of the invention can comprise any suitable human or human consensus light chain framework sequences, provided the antibody exhibits the desired biological characteristics (e.g., a desired binding affinity). In one embodiment, an antibody of the invention comprises at least a portion (or all) of the framework sequence of human κ light chain. In one embodiment, an antibody of the invention comprises at least a portion (or all) of human κ subgroup I framework consensus sequence.

In one embodiment, an antibody of the invention comprises a heavy and/or light chain variable domain comprising framework sequence depicted in SEQ ID NO: 12 and/or 14 (FIG. 1), provided position 94 in the heavy chain is not R (and is preferably but not necessarily S or T).

In one aspect, an antibody of the invention is a humanized anti-c-met antibody that inhibits binding of human hepatocyte growth factor to its receptor better than a reference antibody comprising a chimeric anti-c-met antibody comprising a light chain and heavy chain variable sequence as depicted in FIG. 7 (SEQ ID NO: 9 and 10). For example, in one embodiment, an antibody of the invention inhibits HGF binding with an IC50 value that is less than about half that of the chimeric antibody. In one embodiment, the IC50 value of an antibody of the invention is about 0.1, 0.2, 0.3 or 0.4 that of the chimeric antibody. Comparison of abilities to inhibit HGF binding to its receptor can be performed according to various methods known in the art, including as described in the Examples below. In one embodiment, IC50 values are determined across an antibody concentration range from about 0.01 nM to around 1000 nM.

In one aspect, an antibody of the invention is a humanized anti-c-met antibody that inhibits human hepatocyte growth factor (HGF) receptor activation better than a reference antibody comprising a chimeric anti-c-met antibody comprising a light chain and heavy chain variable sequence as depicted in FIG. 7 (SEQ ID NO: 9 and 10). For example in one embodiment, an antibody of the invention inhibits receptor activation with an IC50 value that is less than about half that of the chimeric antibody. In one embodiment, the IC50 value of an antibody of the invention is about 0.1, 0.2, 0.3 or 0.4 that of the chimeric antibody. Comparison of abilities to inhibit HGF receptor activation can be performed according to various methods known in the art, including as described in the Examples below. In one embodiment, IC50 values are determined across an antibody concentration range from about 0.1 nM to about 100 nM.

In one aspect, an antibody of the invention is a humanized anti-c-met antibody that inhibits c-met-dependent cell proliferation better than a reference antibody comprising a chimeric anti-c-met antibody comprising a light chain and heavy chain variable sequence as depicted in FIG. 7 (SEQ ID NO: 9 and 10). For example, in one embodiment, an antibody of the invention inhibits cell proliferation with an IC50 value that is less than about half that of the chimeric antibody. In one embodiment, the IC50 value of an antibody of the invention is about 0.1, 0.2, 0.3 or 0.4 that of the chimeric antibody. Comparison of abilities to inhibit cell proliferation can be performed according to various methods known in the art, including as described in the Examples below. In one embodiment, IC50 values are determined across an antibody concentration range from about 0.01 nM to about 100 nM.

In one embodiment, both the humanized antibody and chimeric antibody are monovalent. In one embodiment, both the humanized antibody and chimeric antibody comprise a single Fab region linked to an Fc region. In one embodiment, the reference chimeric antibody comprises variable domain sequences depicted in FIG. 7 (SEQ ID NO: 9 and 10) linked to a human Fc region. In one embodiment, the human Fc region is that of an IgG (e.g., IgG1, 2, 3 or 4).

In one aspect, the invention provides an antibody comprising a heavy chain variable domain comprising the HVR1-HC, HVR2-HC and/or HVR3-HC sequence depicted in FIG. 13. In one embodiment, the variable domain comprises FR1-HC, FR2-HC, FR3-HC and/or FR4-HC sequence depicted in FIG. 13. In one embodiment, the antibody comprises CH1 and/or Fc sequence depicted in FIG. 13. In one embodiment, an antibody of the invention comprises a heavy chain variable domain comprising the HVR1-HC, HVR2-HC and/or HVR3-HC sequence, and the FR1-HC, FR2-HC, FR3-HC and/or FR4-HC sequence depicted in FIG. 13. In one embodiment, an antibody of the invention comprises a heavy chain variable domain comprising the HVR1-HC, HVR2-HC and/or HVR3-HC sequence, and the CH1 and/or Fc sequence depicted in FIG. 13. In one embodiment, an antibody of the invention comprises a heavy chain variable domain comprising the HVR1-HC, HVR2-HC and/or HVR3-HC sequence, and the FR1-HC, FR2-HC, FR3-HC and/or FR4-HC sequence depicted in FIG. 13, and the CH1 and/or Fc sequence depicted in FIG. 13. In one embodiment, the Fc region of the antibody of the invention comprises a complex between a polypeptide comprising the Fc sequence in FIG. 13 and a polypeptide comprising the Fc sequence in FIG. 14.

In one aspect, the invention provides an antibody comprising a light chain variable domain comprising HVR1-LC, HVR2-LC and/or HVR3-LC sequence depicted in FIG. 13. In one embodiment, the variable domain comprises FR1-LC, FR2-LC, FR3-LC and/or FR4-LC sequence depicted in FIG. 13. In one embodiment, the antibody comprises CL1 sequence depicted in FIG. 13.

In one embodiment, an antibody of the invention comprises light and heavy chain variable domains as described in the preceding two paragraphs. In one embodiment, the antibody is monovalent and comprises an Fc region. In one embodiment, the Fc region comprises at least one protuberance (knob) and at least one cavity (hole), wherein presence of the protuberance and cavity enhances formation of a complex between an Fc polypeptide comprising the protuberance and an Fc polypeptide comprising the cavity, for example as described in WO 2005/063816. In one embodiment, the Fc region of an antibody of the invention comprises a first and a second Fc polypeptide, wherein the first and second polypeptide each comprises one or more mutations with respect to wild type human Fc. In one embodiment, a cavity mutation is T366S, L368A and/or Y407V. In one embodiment, a protuberance mutation is T366W. In one embodiment, the first polypeptide comprises the Fc sequence depicted in FIG. 13 and the second polypeptide comprises the Fc sequence depicted in FIG. 14.

Antagonists of the invention can be used to modulate one or more aspects of HGF/c-met-associated effects, including but not limited to c-met activation, downstream molecular signaling (e.g., mitogen activated protein kinase (MAPK) phosphorylation), cell proliferation, cell migration, cell survival, cell morphogenesis and angiogenesis. These effects can be modulated by any biologically relevant mechanism, including disruption of ligand (e.g., HGF) binding to c-met, c-met phosphorylation and/or c-met multimerization. Accordingly, in one embodiment, the invention provides a c-met antagonist antibody that inhibits binding of HGF to c-met. In one embodiment, a c-met antagonist antibody of the invention disrupts c-met multimerization (e.g., dimerization). In one embodiment, a c-met antagonist antibody of the invention disrupts dimerization function of c-met Sema domain. In one example, a c-met antagonist antibody interferes with ability of c-met Sema domain to effect c-met dimerization. Interference can be direct or indirect. For example, a c-met antagonist antibody may bind to a sequence within the c-met Sema domain, and thereby inhibit interaction of said bound domain with its binding partner (such as another c-met molecule). In another example, a c-met antagonist antibody may bind to a sequence that is not within the c-met Sema domain, but wherein said binding results in disruption of the ability of the c-met Sema domain to interact with its binding partner (such as another c-met molecule). In one embodiment, an antagonist antibody of the invention binds to c-met (e.g., the extracellular domain) such that c-met dimerization is disrupted. In one embodiment, an antagonist antibody of the invention binds to c-met such that ability of c-met Sema domain to effect c-met dimerization is disrupted. For example, in one embodiment, the invention provides an antagonist antibody which upon binding to a c-met molecule inhibits dimerization of said molecule. In one embodiment, a c-met antagonist antibody of the invention specifically binds a sequence in the c-met Sema domain.

In one embodiment, an antagonist antibody of the invention disrupts c-met dimerization comprising homodimerization. In one embodiment, an antagonist antibody of the invention disrupts c-met dimerization comprising heterodimerization (i.e., c-met dimerization with a non-c-met molecule).

In some instances, it may be advantageous to have a c-met antagonist antibody that does not interfere with binding of a ligand (such as HGF) to c-met. Accordingly, in one embodiment, the invention provides an antibody that does not bind an HGF binding site on c-met. In another embodiment, an antibody of the invention does not substantially inhibit HGF binding to c-met. In one embodiment, an antibody of the invention does not substantially compete with HGF for binding to c-met. In one example, an antagonist antibody of the invention can be used in conjunction with one or more other antagonists, wherein the antagonists are targeted at different processes and/or functions within the HGF/c-met axis. Thus, in one embodiment, a c-met antagonist antibody of the invention binds to an epitope on c-met distinct from an epitope bound by another c-met antagonist (such as the Fab fragment of the monoclonal antibody produced by the hybridoma cell line deposited under American Type Culture Collection Accession Number ATCC HB-11894 (hybridoma 1A3.3.13)). In another embodiment, a c-met antagonist antibody of the invention is distinct from (i.e., it is not) a Fab fragment of the monoclonal antibody produced by the hybridoma cell line deposited under American Type Culture Collection Accession Number ATCC HB-11894 (hybridoma 1A3.3.13).

In one embodiment, the invention provides a c-met antagonist antibody that disrupts both c-met multimerization and ligand binding. For example, an antagonist antibody of the invention that inhibits c-met multimerization (e.g., dimerization) may further comprise an ability to compete with HGF for binding to c-met.

In one embodiment of a c-met antagonist antibody of the invention, binding of the antagonist to c-met inhibits c-met activation by HGF. In another embodiment of a c-met antagonist antibody of the invention, binding of the antagonist to c-met in a cell inhibits proliferation, survival, scattering, morphogenesis and/or motility of the cell.

In one embodiment, a c-met antagonist antibody of the invention specifically binds at least a portion of c-met Sema domain or variant thereof. In one example, an antagonist antibody of the invention specifically binds at least one of the sequences selected from the group consisting of LDAQT (SEQ ID NO:15) (e.g., residues 269-273 of c-met), LTEKRKKRS (SEQ ID NO:16) (e.g., residues 300-308 of c-met), KPDSAEPM (SEQ ID NO:17) (e.g., residues 350-357 of c-met) and NVRCLQHF (SEQ ID NO:18) (e.g., residues 381-388 of c-met). In one embodiment, an antagonist antibody of the invention specifically binds a conformational epitope formed by part or all of at least one of the sequences selected from the group consisting of LDAQT (e.g., residues 269-273 of c-met), LTEKRKKRS (e.g., residues 300-308 of c-met), KPDSAEPM (e.g., residues 350-357 of c-met) and NVRCLQHF (e.g., residues 381-388 of c-met). In one embodiment, an antagonist antibody of the invention specifically binds an amino acid sequence having at least 50%, 60%, 70%, 80%, 90%, 95%, 98% sequence identity or similarity with the sequence LDAQT, LTEKRKKRS, KPDSAEPM and/or NVRCLQHF.

In one embodiment, an antibody of the invention specifically binds to HGF receptor of a first animal species, and does not specifically bind to HGF receptor of a second animal species. In one embodiment, the first animal species is human and/or primate (e.g., cynomolgus monkey), and the second animal species is murine (e.g., mouse) and/or canine. In one embodiment, the first animal species is human. In one embodiment, the first animal species is primate, for example cynomolgus monkey. In one embodiment, the second animal species is murine, for example mouse. In one embodiment, the second animal species is canine.

In one aspect, the invention provides compositions comprising one or more antagonist antibodies of the invention and a carrier. In one embodiment, the carrier is pharmaceutically acceptable.

In one aspect, the invention provides nucleic acids encoding a c-met antagonist antibody of the invention.

In one aspect, the invention provides vectors comprising a nucleic acid of the invention.

In one aspect, the invention provides host cells comprising a nucleic acid or a vector of the invention. A vector can be of any type, for example a recombinant vector such as an expression vector. Any of a variety of host cells can be used. In one embodiment, a host cell is a prokaryotic cell, for example, *E. coli*. In one embodiment, a host cell is a eukaryotic cell, for example a mammalian cell such as Chinese Hamster Ovary (CHO) cell.

In one aspect, the invention provides methods for making an antagonist of the invention. For example, the invention provides a method of making a c-met antagonist antibody (which, as defined herein includes full length and fragments thereof), said method comprising expressing in a suitable host cell a recombinant vector of the invention encoding said antibody (or fragment thereof), and recovering said antibody.

In one aspect, the invention provides an article of manufacture comprising a container; and a composition contained within the container, wherein the composition comprises one or more c-met antagonist antibodies of the invention. In one embodiment, the composition comprises a nucleic acid of the invention. In one embodiment, a composition comprising an antagonist antibody further comprises a carrier, which in some embodiments is pharmaceutically acceptable. In one embodiment, an article of manufacture of the invention further comprises instructions for administering the composition (e.g., the antagonist antibody) to a subject.

In one aspect, the invention provides a kit comprising a first container comprising a composition comprising one or more c-met antagonist antibodies of the invention; and a second container comprising a buffer. In one embodiment, the buffer is pharmaceutically acceptable. In one embodiment, a composition comprising an antagonist antibody further comprises a carrier, which in some embodiments is pharmaceutically acceptable. In one embodiment, a kit further comprises instructions for administering the composition (e.g., the antagonist antibody) to a subject.

In one aspect, the invention provides use of a c-met antagonist antibody of the invention in the preparation of a medicament for the therapeutic and/or prophylactic treatment of a disease, such as a cancer, a tumor, a cell proliferative disorder, an immune (such as autoimmune) disorder and/or an angiogenesis-related disorder.

In one aspect, the invention provides use of a nucleic acid of the invention in the preparation of a medicament for the therapeutic and/or prophylactic treatment of a disease, such as a cancer, a tumor, a cell proliferative disorder, an immune (such as autoimmune) disorder and/or an angiogenesis-related disorder.

In one aspect, the invention provides use of an expression vector of the invention in the preparation of a medicament for the therapeutic and/or prophylactic treatment of a disease, such as a cancer, a tumor, a cell proliferative disorder, an immune (such as autoimmune) disorder and/or an angiogenesis-related disorder.

In one aspect, the invention provides use of a host cell of the invention in the preparation of a medicament for the therapeutic and/or prophylactic treatment of a disease, such as a cancer, a tumor, a cell proliferative disorder, an immune (such as autoimmune) disorder and/or an angiogenesis-related disorder.

In one aspect, the invention provides use of an article of manufacture of the invention in the preparation of a medicament for the therapeutic and/or prophylactic treatment of a disease, such as a cancer, a tumor, a cell proliferative disorder, an immune (such as autoimmune) disorder and/or an angiogenesis-related disorder.

In one aspect, the invention provides use of a kit of the invention in the preparation of a medicament for the therapeutic and/or prophylactic treatment of a disease, such as a cancer, a tumor, a cell proliferative disorder, an immune (such as autoimmune) disorder and/or an angiogenesis-related disorder.

The invention provides methods and compositions useful for modulating disease states associated with dysregulation of the HGF/c-met signaling axis. The HGF/c-met signaling pathway is involved in multiple biological and physiological functions, including, e.g., cell proliferation and angiogenesis. Thus, in one aspect, the invention provides a method comprising administering to a subject an antibody of the invention.

In one aspect, the invention provides a method of inhibiting c-met activated cell proliferation, said method comprising contacting a cell or tissue with an effective amount of a antibody of the invention, whereby cell proliferation associated with c-met activation is inhibited.

In one aspect, the invention provides a method of treating a pathological condition associated with dysregulation of c-met activation in a subject, said method comprising administering to the subject an effective amount of an antibody of the invention, whereby said condition is treated.

In one aspect, the invention provides a method of inhibiting the growth of a cell that expresses c-met or hepatocyte growth factor, or both, said method comprising contacting said cell with an antibody of the invention thereby causing an inhibition of growth of said cell. In one embodiment, the cell is contacted by HGF expressed by a different cell (e.g., through a paracrine effect).

In one aspect, the invention provides a method of therapeutically treating a mammal having a cancerous tumor comprising a cell that expresses c-met or hepatocyte growth factor, or both, said method comprising administering to said mammal an effective amount of an antibody of the invention, thereby effectively treating said mammal. In one embodiment, the cell is contacted by HGF expressed by a different cell (e.g., through a paracrine effect).

In one aspect, the invention provides a method for treating or preventing a cell proliferative disorder associated with increased expression or activity of c-met or hepatocyte growth, or both, said method comprising administering to a subject in need of such treatment an effective amount of an antibody of the invention, thereby effectively treating or preventing said cell proliferative disorder. In one embodiment, said proliferative disorder is cancer.

In one aspect, the invention provides a method for inhibiting the growth of a cell, wherein growth of said cell is at least in part dependent upon a growth potentiating effect of c-met or hepatocyte growth factor, or both, said method comprising contacting said cell with an effective amount of an antibody of the invention, thereby inhibiting the growth of said cell. In one embodiment, the cell is contacted by HGF expressed by a different cell (e.g., through a paracrine effect).

A method of therapeutically treating a tumor in a mammal, wherein the growth of said tumor is at least in part dependent upon a growth potentiating effect of c-met or hepatocyte growth factor, or both, said method comprising contacting said cell with an effective amount of an antibody of the invention, thereby effectively treating said tumor. In one embodiment, the cell is contacted by HGF expressed by a different cell (e.g., through a paracrine effect).

Methods of the invention can be used to affect any suitable pathological state, for example, cells and/or tissues associated with dysregulation of the HGF/c-met signaling pathway. In one embodiment, a cell that is targeted in a method of the invention is a cancer cell. For example, a cancer cell can be one selected from the group consisting of a breast cancer cell, a colorectal cancer cell, a lung cancer cell, a papillary carcinoma cell (e.g., of the thyroid gland), a colon cancer cell, a pancreatic cancer cell, an ovarian cancer cell, a cervical cancer cell, a central nervous system cancer cell, an osteogenic sarcoma cell, a renal carcinoma cell, a hepatocellular carcinoma cell, a bladder cancer cell, a gastric carcinoma cell, a head and neck squamous carcinoma cell, a melanoma cell and a leukemia cell. In one embodiment, a cell that is targeted in a method of the invention is a hyperproliferative and/or hyperplastic cell. In one embodiment, a cell that is targeted in a method of the invention is a dysplastic cell. In yet another embodiment, a cell that is targeted in a method of the invention is a metastatic cell.

Methods of the invention can further comprise additional treatment steps. For example, in one embodiment, a method further comprises a step wherein a targeted cell and/or tissue (e.g., a cancer cell) is exposed to radiation treatment or a chemotherapeutic agent.

As described herein, c-met activation is an important biological process the dysregulation of which leads to numerous pathological conditions. Accordingly, in one embodiment of methods of the invention, a cell that is targeted (e.g., a cancer cell) is one in which activation of c-met is enhanced as compared to a normal cell of the same tissue origin. In one embodiment, a method of the invention causes the death of a targeted cell. For example, contact with an antagonist of the invention may result in a cell's inability to signal through the c-met pathway, which results in cell death.

Dysregulation of c-met activation (and thus signaling) can result from a number of cellular changes, including, for example, overexpression of HGF (c-met's cognate ligand) and/or c-met itself. Accordingly, in some embodiments, a method of the invention comprises targeting a cell wherein c-met or hepatoctye growth factor, or both, is more abundantly expressed by said cell (e.g., a cancer cell) as compared to a normal cell of the same tissue origin. A c-met-expressing cell can be regulated by HGF from a variety of sources, i.e. in an autocrine or paracrine manner. For example, in one embodiment of methods of the invention, a targeted cell is contacted/bound by hepatocyte growth factor expressed in a different cell (e.g., via a paracrine effect). Said different cell can be of the same or of a different tissue origin. In one embodiment, a targeted cell is contacted/bound by HGF expressed by the targeted cell itself (e.g., via an autocrine effect/loop). C-met activation and/or signaling can also occur independent of ligand. Hence, in one embodiment of methods of the invention, c-met activation in a targeted cell occurs independent of ligand.

BRIEF DESCRIPTION OF THE DRAWINGS

FIGS. 1A and 1B depict alignment of sequences of the variable light and heavy chains for the following: light chain human subgroup I consensus sequence, heavy chain human subgroup III consensus sequence, murine 5D5 anti-c-met antibody and 5D5-grafted "humanized" antibody.

FIGS. 2A and 2B depict various HVR sequences of selected affinity-matured antibodies from libraries with individually-randomized HVR.

FIG. 3 depicts HVR-1-H3 sequences of selected affinity-matured antibodies from a library pool comprising a combination of 6 libraries encompassing all six HVRs wherein each library is randomized in a single HVR.

FIG. 4 depicts results of Biacore analysis of selected anti-c-met antibodies.

FIGS. 5A,B & 6A,B depict exemplary acceptor human consensus framework sequences for use in practicing the instant invention with sequence identifiers as follows:

Variable Heavy (VH) Consensus Frameworks (FIGS. 5A, B)

human VH subgroup I consensus framework minus Kabat CDRs (SEQ ID NO:19)

human VH subgroup I consensus framework minus extended hypervariable regions (SEQ ID NOs:20-22)

human VH subgroup II consensus framework minus Kabat CDRs (SEQ ID NO:23)

human VH subgroup II consensus framework minus extended hypervariable regions (SEQ ID NOs:24-26)

human VH subgroup III consensus framework minus Kabat CDRs (SEQ ID NO:27)

human VH subgroup III consensus framework minus extended hypervariable regions (SEQ ID NOs:28-30)

human VH acceptor framework minus Kabat CDRs (SEQ ID NO:31)

human VH acceptor framework minus extended hypervariable regions (SEQ ID NOs:32-33)

human VH acceptor 2 framework minus Kabat CDRs (SEQ ID NO:34)

human VH acceptor 2 framework minus extended hypervariable regions (SEQ ID NOs:35-37)

Variable Light (VL) Consensus Frameworks (FIGS. 6A,B)

human VL kappa subgroup I consensus framework (SEQ ID NO:38)

human VL kappa subgroup II consensus framework (SEQ ID NO:39)

human VL kappa subgroup III consensus framework (SEQ ID NO:40)

human VL kappa subgroup IV consensus framework (SEQ ID NO:41)

FIG. 7 depicts donor (murine antibody 5D5) light chain (LC) and heavy chain (HC) variable domain sequences.

Figure 8:
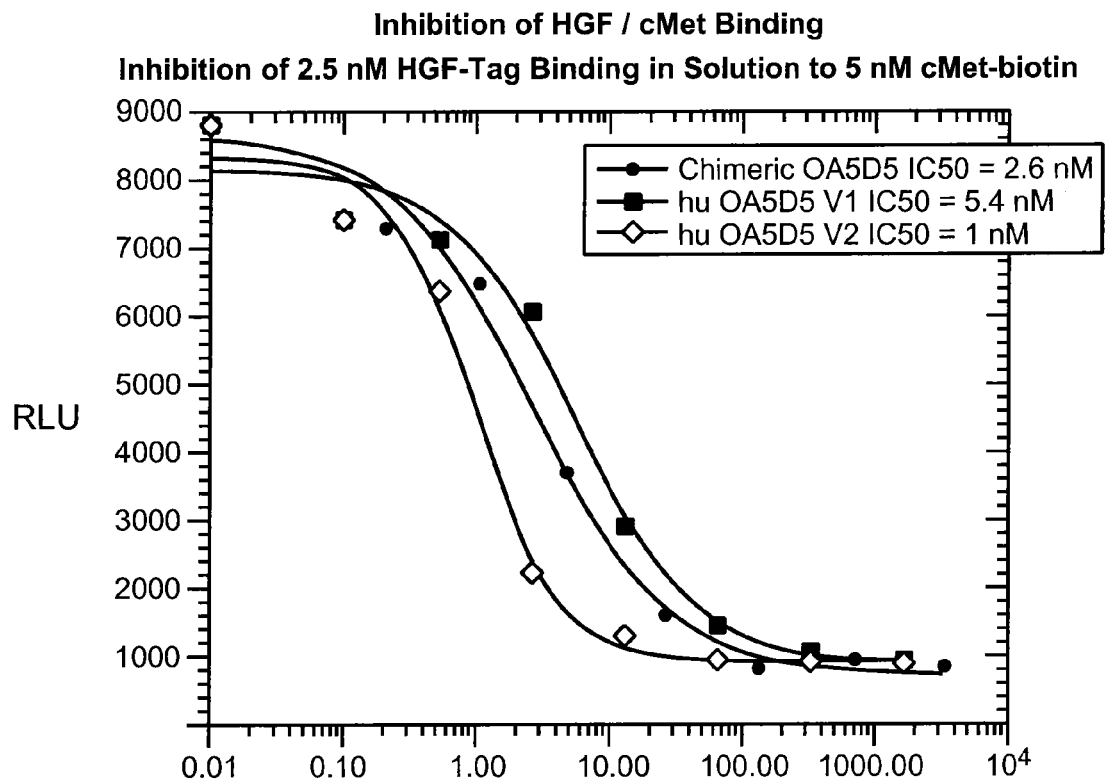

FIG. 8 depicts graphical data for blocking of HGF binding to its receptor by an antibody of the invention.

Figure 9:
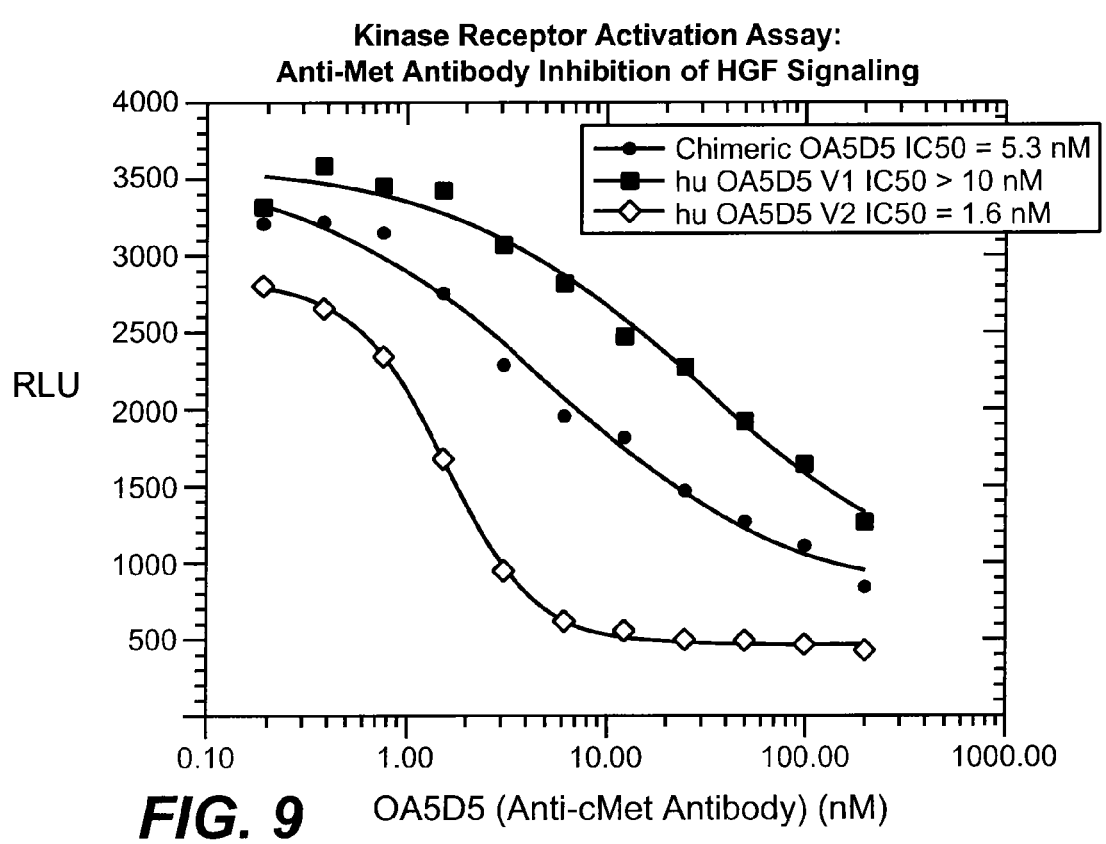

FIG. 9 depicts graphical data for inhibition of HGF receptor activation by an antibody of the invention.

Figure 10:
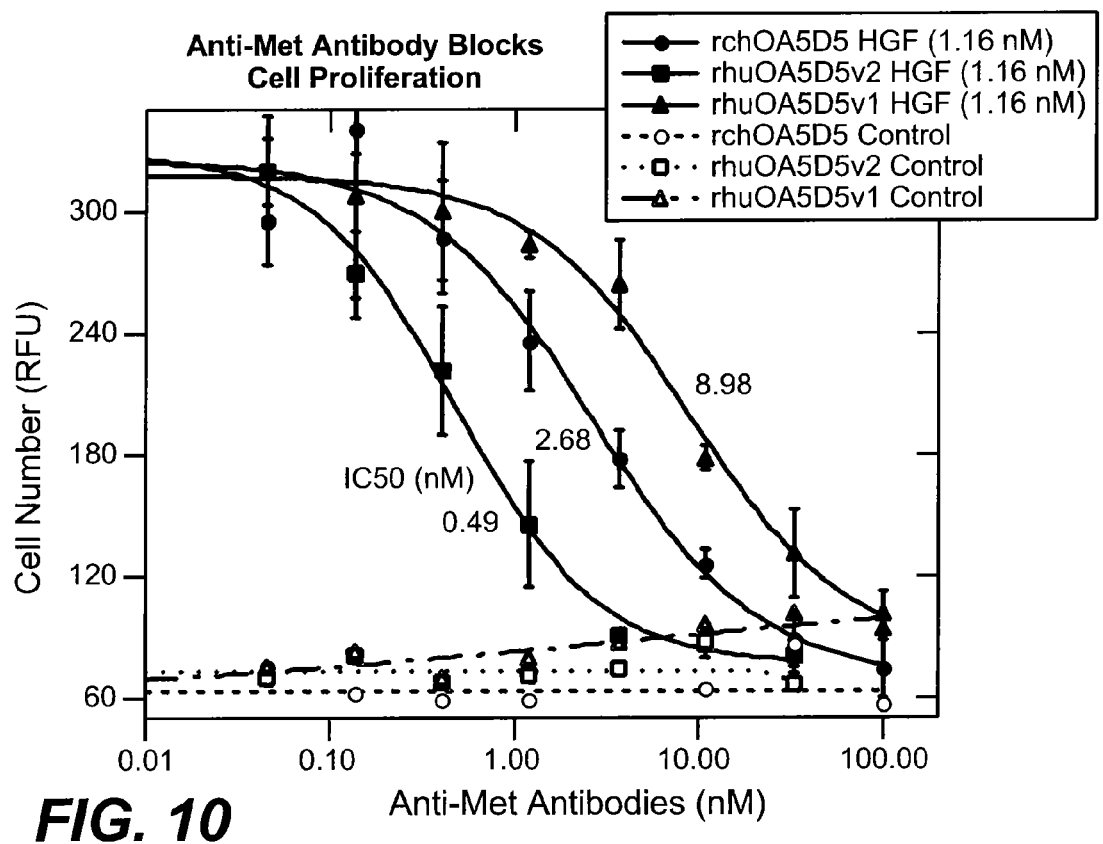

FIG. 10 depicts graphical data for inhibition of cell proliferation by an antibody of the invention. "rchOA5D5 HGF" refers to chimeric one-armed 5D5 antibody plus HGF; "rhuOA5D5v2 HGF" refers to OA5D5.v2 plus HGF; "rhuOA5D5v1 HGF" refers to OA5D5.v1 plus HGF". "rchOA5D5 Control" refers to chimeric one-armed 5D5 antibody without HGF; "rhuOA5D5v2 Control" refers to OA5D5.v2 without HGF; "rhuOA5D5v1 Control" refers to OA5D5.v1 without HGF".

Figure 11A:
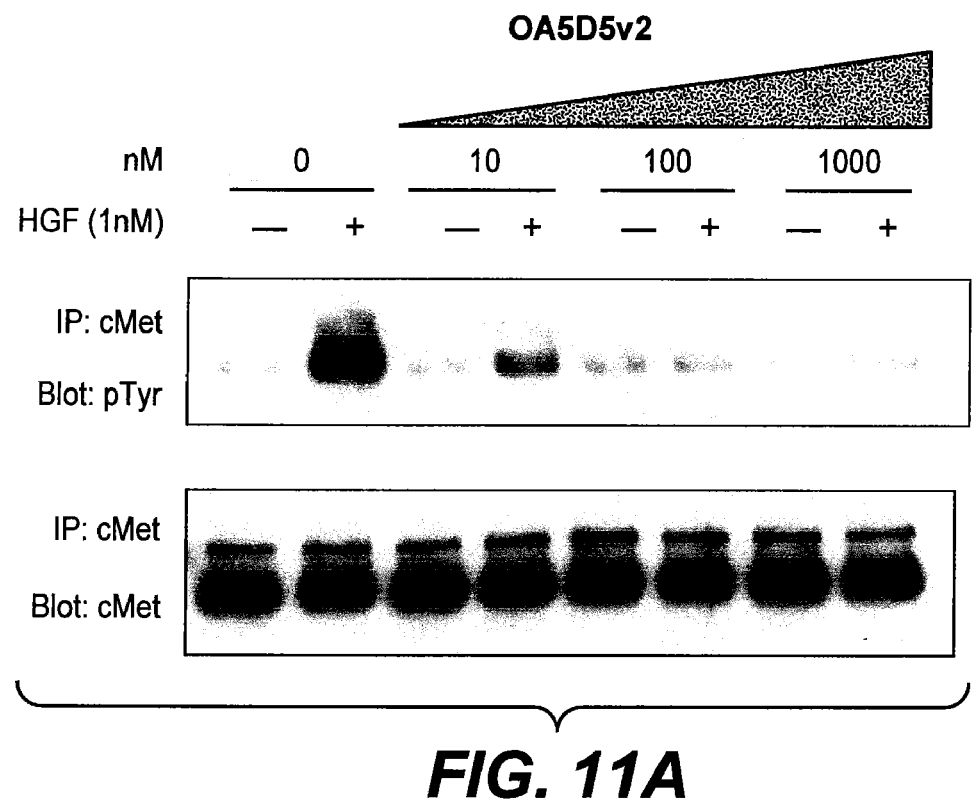
Figure 11B:
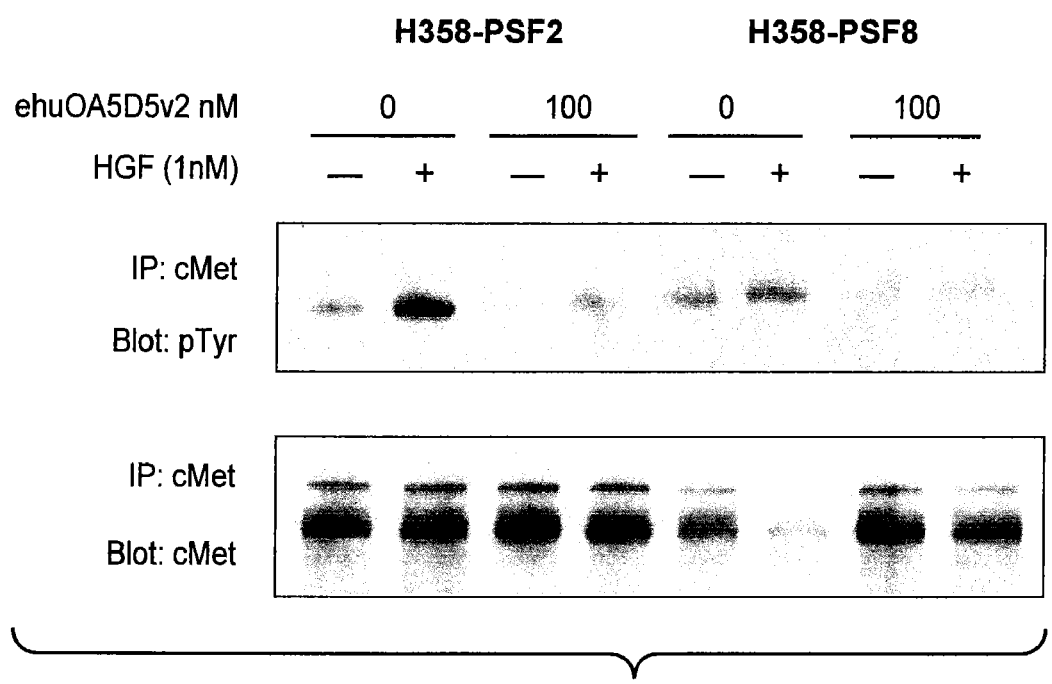

FIGS. 11A, B depicts data for inhibition of receptor phosphorylation in the presence of an antibody of the invention. FIG. 11A depicts receptor phosphorylation of H358 cells. FIG. 11B depicts receptor phosphorylation of H358 cells transfected with HGF.

Figure 12:
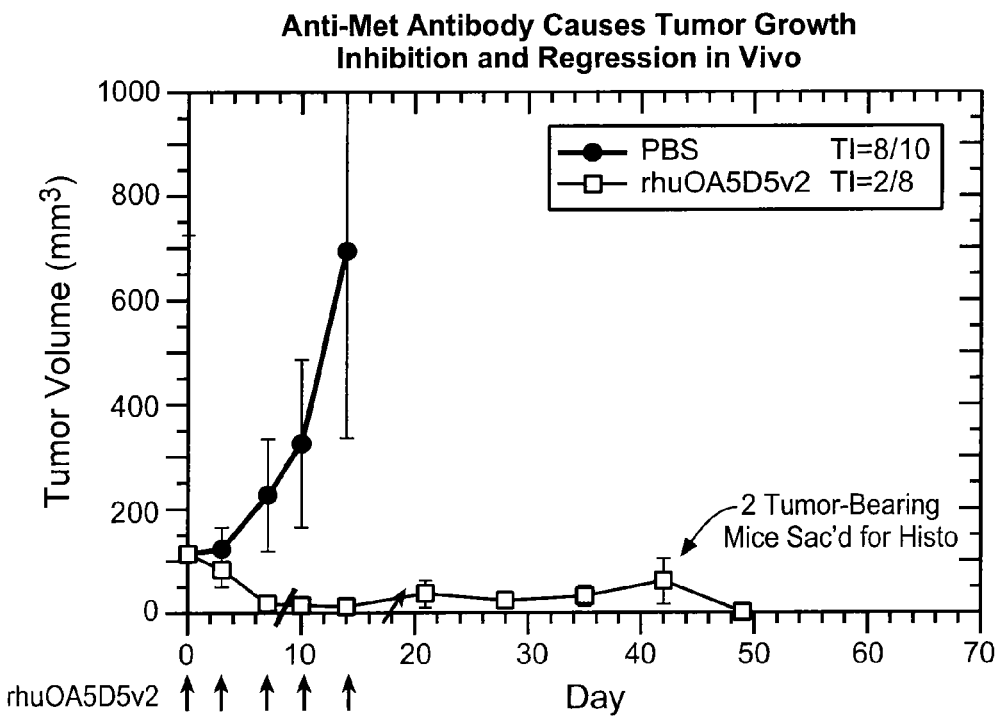

FIG. 12 depicts graphical data showing in vivo efficacy of an antibody of the invention. "TI" refers to tumor incidence. TI=8/10 refers to 8 mice having tumors out of a group of 10 mice. TI=2/8 refers to 2 mice having tumors out of a group of 8 mice.

FIG. 13 depicts amino acid sequences of the framework (FR), hypervariable region (HVR), first constant domain (CL or CH1) and Fc region (Fc) of one embodiment of an antibody of the invention (5D5.v2). The Fc sequence depicted comprises "hole" (cavity) mutations T366S, L368A and Y407V, as described in WO 2005/063816.

FIG. 14 depicts sequence of an Fc polypeptide comprising "knob" (protuberance) mutation T366W, as described in WO 2005/063816. In one embodiment, an Fc polypeptide comprising this sequence forms a complex with an Fc polypeptide comprising the Fc sequence of FIG. 13 to generate an Fc region of an antibody of the invention.

MODES FOR CARRYING OUT THE INVENTION

The invention provides methods, compositions, kits and articles of manufacture for identifying and/or using inhibitors of the HGF/c-met signaling pathway.

Details of these methods, compositions, kits and articles of manufacture are provided herein.

General Techniques

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., ed., 1994); "A Practical Guide to Molecular Cloning" (Perbal Bernard V., 1988); "Phage Display: A Laboratory Manual" (Barbas et al., 2001).

DEFINITIONS

A "modification" of an amino acid residue/position, as used herein, refers to a change of a primary amino acid sequence as compared to a starting amino acid sequence, wherein the change results from a sequence alteration involving said amino acid residue/positions. For example, typical modifications include substitution of the residue (or at said position) with another amino acid (e.g., a conservative or non-conservative substitution), insertion of one or more (generally fewer than 5 or 3) amino acids adjacent to said residue/position, and deletion of said residue/position. An "amino acid substitution", or variation thereof, refers to the replacement of an existing amino acid residue in a predetermined (starting) amino acid sequence with a different amino acid residue. Generally and preferably, the modification results in alteration in at least one physicobiochemical activity of the variant polypeptide compared to a polypeptide comprising the starting (or "wild type") amino acid sequence. For example, in the case of an antibody, a physicobiochemical activity that is altered can be binding affinity, binding capability and/or binding effect upon a target molecule.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The term "variable domain residue numbering as in Kabat" or "amino acid position numbering as in Kabat", and variations thereof, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, a FR or CDR of the variable domain. For example, a heavy chain variable domain may include a single amino acid insert (residue 52a according to Kabat) after residue 52 of H2 and inserted residues (e.g. residues 82a, 82b, and 82c, etc according to Kabat) after heavy chain FR residue 82. The Kabat numbering of residues may be determined for a given antibody by alignment at regions of homology of the sequence of the antibody with a "standard" Kabat numbered sequence.

The phrase "substantially similar," or "substantially the same", as used herein, denotes a sufficiently high degree of similarity between two numeric values (generally one associated with an antibody of the invention and the other associated with a reference/comparator antibody) such that one of skill in the art would consider the difference between the two values to be of little or no biological and/or statistical significance within the context of the biological characteristic measured by said values (e.g., Kd values). The difference between said two values is preferably less than about 50%, preferably less than about 40%, preferably less than about 30%, preferably less than about 20%, preferably less than about 10% as a function of the value for the reference/comparator antibody.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described in the following.

In one embodiment, the "Kd" or "Kd value" according to this invention is measured by a radiolabeled antigen binding assay (RIA) performed with the Fab version of an antibody of interest and its antigen as described by the following assay that measures solution binding affinity of Fabs for antigen by equilibrating Fab with a minimal concentration of ($^{125}$I)-labeled antigen in the presence of a titration series of unlabeled antigen, then capturing bound antigen with an anti-Fab antibody-coated plate (Chen, et al., (1999) *J. Mol Biol* 293: 865-881). To establish conditions for the assay, microtiter plates (Dynex) are coated overnight with 5 ug/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbant plate (Nunc #269620), 100 pM or 26 pM [$^{125}$I]-antigen are mixed with serial dilutions of a Fab of interest (e.g., consistent with assessment of an anti-VEGF antibody, Fab-12, in Presta et al., (1997) *Cancer Res.* 57:4593-4599). The Fab of interest is then incubated overnight; however, the incubation may continue for a longer period (e.g., 65 hours) to insure that equilibrium is reached. Thereafter, the mixtures are transferred to the capture plate for incubation at room temperature (e.g., for one hour). The solution is then removed and the plate washed eight times with 0.1% Tween-20 in PBS. When the plates have dried, 150 ul/well of scintillant (MicroScint-20; Packard) is added, and the plates are counted on a Topcount gamma counter (Packard) for ten minutes. Concentrations of each Fab that give less than or equal to 20% of maximal binding are chosen for use in competitive binding assays. According to another embodiment the Kd or Kd value is measured by using surface plasmon resonance assays using a BIAcore™-2000 or a BIAcore™-3000 (BIAcore, Inc., Piscataway, N.J.) at 25 C with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 ug/ml (~0.2 uM) before injection at a flow rate of 5 ul/minute to achieve approximately 10 response units (RU) of coupled protein. Following the injection of antigen, 1M ethanolamine is injected to block unreacted groups. For kinetics measurements, two-fold serial dilutions of Fab (0.78 nM to 500 nM) are injected in PBS with 0.05% Tween 20 (PBST) at 25° C. at a flow rate of approximately 25 ul/min. Association rates ($k_{on}$) and dissociation rates ($k_{off}$) are calculated using a simple one-to-one Langmuir binding model (BIAcore Evaluation Software version 3.2) by simultaneous fitting the association and dissociation sensorgram. The equilibrium dissociation constant (Kd) is calculated as the ratio $k_{off}/k_{on}$. See, e.g., Chen, Y., et al., (1999) *J. Mol Biol* 293:865-881. If the on-rate exceeds $10^6$ M$^{-1}$ S$^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-Aminco spectrophotometer (ThermoSpectronic) with a stirred cuvette.

An "on-rate" or "rate of association" or "association rate" or "$k_{on}$" according to this invention can also be determined with the same surface plasmon resonance technique described above using a BIAcore™-2000 or a BIAcore™-3000 (BIAcore, Inc., Piscataway, N.J.) at 25 C with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 ug/ml (~0.2 uM) before injection at a flow rate of 5 ul/minute to achieve approximately 10 response units (RU) of coupled protein. Following the injection of 1M ethanolamine to block unreacted groups. For kinetics measurements, two-fold serial dilutions of Fab (0.78 nM to 500 nM) are injected in PBS with 0.05% Tween 20 (PBST) at 25° C. at a flow rate of approximately 25 ul/min. Association rates ($k_{on}$) and dissociation rates ($k_{off}$) are calculated using a simple one-to-one Langmuir binding model (BIAcore Evaluation Software version 3.2) by simultaneous fitting the association and dissociation sensorgram. The equilibrium dissociation constant (Kd) was calculated as the ratio $k_{off}/k_{on}$. See, e.g., Chen, Y., et al., (1999) *J. Mol Biol* 293:865-881. However, if the on-rate exceeds $10^6$ $M^{-1}$ $S^{-1}$ by the surface plasmon resonance assay above, then the on-rate is preferably determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-Aminco spectrophotometer (ThermoSpectronic) with a stirred cuvette. The "Kd" or "Kd value" according to this invention is in one embodiment measured by a radiolabeled antigen binding assay (RIA) performed with the Fab version of the antibody and antigen molecule as described by the following assay that measures solution binding affinity of Fabs for antigen by equilibrating Fab with a minimal concentration of ($^{125}$I)-labeled antigen in the presence of a titration series of unlabeled antigen, then capturing bound antigen with an anti-Fab antibody-coated plate (Chen, et al., (1999) *J. Mol Biol* 293: 865-881). To establish conditions for the assay, microtiter plates (Dynex) are coated overnight with 5 ug/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbant plate (Nunc #269620), 100 pM or 26 pM [$^{125}$I]-antigen are mixed with serial dilutions of a Fab of interest (consistent with assessment of an anti-VEGF antibody, Fab-12, in Presta et al., (1997) *Cancer Res.* 57:4593-4599). The Fab of interest is then incubated overnight; however, the incubation may continue for a longer period (e.g., 65 hours) to insure that equilibrium is reached. Thereafter, the mixtures are transferred to the capture plate for incubation at room temperature for one hour. The solution is then removed and the plate washed eight times with 0.1% Tween-20 in PBS. When the plates have dried, 150 ul/well of scintillant (MicroScint-20; Packard) is added, and the plates are counted on a Topcount gamma counter (Packard) for ten minutes. Concentrations of each Fab that give less than or equal to 20% of maximal binding are chosen for use in competitive binding assays. According to another embodiment, the Kd or Kd value is measured by using surface plasmon resonance assays using a BIAcore™-2000 or a BIAcore™-3000 (BIAcore, Inc., Piscataway, N.J.) at 25 C with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 ug/ml (~0.2 uM) before injection at a flow rate of 5 ul/minute to achieve approximately 10 response units (RU) of coupled protein. Following the injection of antigen, 1M ethanolamine is injected to block unreacted groups. For kinetics measurements, two-fold serial dilutions of Fab (0.78 nM to 500 nM) are injected in PBS with 0.05% Tween 20 (PBST) at 25° C. at a flow rate of approximately 25 ul/min. Association rates ($k_{on}$) and dissociation rates ($k_{off}$) are calculated using a simple one-to-one Langmuir binding model (BIAcore Evaluation Software version 3.2) by simultaneous fitting the association and dissociation sensorgram. The equilibrium dissociation constant (Kd) is calculated as the ratio $k_{off}/k_{on}$. See, e.g., Chen, Y., et al., (1999) *J. Mol Biol* 293:865-881. If the on-rate exceeds $10^6$ $M^{-1}$ $S^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-Aminco spectrophotometer (ThermoSpectronic) with a stirred cuvette.

In one embodiment, an "on-rate" or "rate of association" or "association rate" or "$k_{on}$" according to this invention is determined with the same surface plasmon resonance technique described above using a BIAcore™-2000 or a BIAcore™-3000 (BIAcore, Inc., Piscataway, N.J.) at 25 C with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 ug/ml (~0.2 uM) before injection at a flow rate of 5 ul/minute to achieve approximately 10 response units (RU) of coupled protein. Following the injection of antigen, 1M ethanolamine is injected to block unreacted groups. For kinetics measurements, two-fold serial dilutions of Fab (0.78 nM to 500 nM) are injected in PBS with 0.05% Tween 20 (PBST) at 25° C. at a flow rate of approximately 25 ul/min. Association rates ($k_{on}$) and dissociation rates ($k_{off}$) are calculated using a simple one-to-one Langmuir binding model (BIAcore Evaluation Software version 3.2) by simultaneous fitting the association and dissociation sensorgram. The equilibrium dissociation constant (Kd) was calculated as the ratio $k_{off}/k_{on}$. See, e.g., Chen, Y., et al., (1999) *J. Mol Biol* 293:865-881. However, if the on-rate exceeds $10^6$ $M^{-1}$ $S^{-1}$ by the surface plasmon resonance assay above, then the on-rate is preferably determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-Aminco spectrophotometer (ThermoSpectronic) with a stirred cuvette.

The phrase "substantially reduced," or "substantially different", as used herein, denotes a sufficiently high degree of difference between two numeric values (generally one associated with an antibody of the invention and the other associated with a reference/comparator antibody) such that one of skill in the art would consider the difference between the two values to be of statistical significance within the context of the biological characteristic measured by said values (e.g., Kd values, HAMA response). The difference between said two values is preferably greater than about 10%, preferably greater than about 20%, preferably greater than about 30%, preferably greater than about 40%, preferably greater than about 50% as a function of the value for the reference/comparator antibody.

"Percent (%) amino acid sequence identity" with respect to a peptide or polypeptide sequence is defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2, wherein the complete source code for the ALIGN-2 program is provided in Table A below. The ALIGN-2 sequence comparison computer program was authored by Genentech, Inc. and the source code shown in Table A below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in FIG. 8 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

Unless specifically stated otherwise, all % amino acid sequence identity values used herein are obtained as described in the immediately preceding paragraph using the ALIGN-2 computer program of Table A.

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "recombinant vectors"). In general, expression vectors of utility in recombinant DNA techniques are often in the form of plasmids. In the present specification, "plasmid" and "vector" may be used interchangeably as the plasmid is the most commonly used form of vector.

"Polynucleotide," or "nucleic acid," as used interchangeably herein, refer to polymers of nucleotides of any length, and include DNA and RNA. The nucleotides can be deoxyribonucleotides, to ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), "(O)NR$_2$ ("amidate"), P(O) R, P(O)OR', CO or CH$_2$ ("formacetal"), in which each R or R' is independently H or substituted or unsubstituted alkyl (1-20 C.) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, generally single stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

The term "hepatocyte growth factor" or "HGF", as used herein, refers, unless specifically or contextually indicated otherwise, to any native or variant (whether native or synthetic) HGF polypeptide that is capable of activating the HGF/c-met signaling pathway under conditions that permit such process to occur. The term "wild type HGF" generally refers to a polypeptide comprising the amino acid sequence of a naturally occurring HGF protein. The term "wild type HGF sequence", generally refers to an amino acid sequence found in a naturally occurring HGF.

The terms "antibody" and "immunoglobulin" are used interchangeably in the broadest sense and include monoclonal antibodies (e.g., full length or intact monoclonal antibodies), polyclonal antibodies, multivalent antibodies, multispecific antibodies (e.g., bispecific antibodies so long as they exhibit the desired biological activity) and may also include certain antibody fragments (as described in greater detail herein). An antibody can be human, humanized and/or affinity matured.

"Antibody fragments" comprise only a portion of an intact antibody, wherein the portion preferably retains at least one, preferably most or all, of the functions normally associated with that portion when present in an intact antibody. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half life modulation, ADCC function and complement binding. In one embodiment, an antibody fragment is a monovalent antibody that has an in vivo half life substantially similar to an intact antibody. For example, such an antibody fragment may comprise one antigen binding arm linked to an Fc sequence capable of conferring in vivo stability to the fragment. In one embodiment, an antibody of the invention is a one-armed antibody as described in WO2005/063816. In one embodiment, the one-armed antibody comprises Fc mutations constituting "knobs" and "holes" as described in WO2005/063816. For example, a hole mutation can be one or more of T366A, L368A and/or Y407V in an Fc polypeptide, and a knob mutation can be T366W.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6851-6855 (1984)).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992). See also the following review articles and references cited therein: Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994).

An "antigen" is a predetermined antigen to which an antibody can selectively bind. The target antigen may be polypeptide, carbohydrate, nucleic acid, lipid, hapten or other naturally occurring or synthetic compound. Preferably, the target antigen is a polypeptide. An "acceptor human framework" for the purposes herein is a framework comprising the amino acid sequence of a VL or VH framework derived from a human immunoglobulin framework, or from a human consensus framework. An acceptor human framework "derived from" a human immunoglobulin framework or human consensus framework may comprise the same amino acid sequence thereof, or may contain pre-existing amino acid sequence changes. Where pre-existing amino acid changes are present, preferably no more than 5 and preferably 4 or less, or 3 or less, pre-existing amino acid changes are present. Where pre-existing amino acid changes are present in a VH, preferably those changes are only at three, two or one of positions 71H, 73H and 78H; for instance, the amino acid residues at those positions may be 71A, 73T and/or 78A. In one embodiment, the VL acceptor human framework is identical in sequence to the VL human immunoglobulin framework sequence or human consensus framework sequence.

A "human consensus framework" is a framework which represents the most commonly occurring amino acid residue in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al. In one embodiment, for the VL, the subgroup is subgroup kappa I as in Kabat et al. In one embodiment, for the VH, the subgroup is subgroup III as in Kabat et al.

A "VH subgroup III consensus framework" comprises the consensus sequence obtained from the amino acid sequences in variable heavy subgroup III of Kabat et al. In one embodiment, the VH subgroup III consensus framework amino acid sequence comprises at least a portion or all of each of the following sequences: EVQLVESGGGLVQPGGSL-RLSCAAS (SEQ ID NO:42)-H1-WVRQAPGKGLEWV (SEQ ID NO:43)-H2-RFTISRDNSKNTLYLQMNSL-RAEDTAVYYC (SEQ ID NO:44)-H3-WGQGTLVTVSS (SEQ ID NO:45).

A "VL subgroup I consensus framework" comprises the consensus sequence obtained from the amino acid sequences in variable light kappa subgroup I of Kabat et al. In one embodiment, the VH subgroup I consensus framework amino acid sequence comprises at least a portion or all of each of the following sequences:

DIQMTQSPSSLSASVGDRVTITC (SEQ ID NO:46)-L1-WYQQKPGKAPKLLIY (SEQ ID NO:47)-L2-GVPSRF-SGSGSGTDFTLTISSLQPEDFATYYC (SEQ ID NO:48)-L3-FGQGTKVEIK (SEQ ID NO:49).

An "unmodified human framework" is a human framework which has the same amino acid sequence as the acceptor human framework, e.g. lacking human to non-human amino acid substitution(s) in the acceptor human framework.

An "altered hypervariable region" for the purposes herein is a hypervariable region comprising one or more (e.g. one to about 16) amino acid substitution(s) therein.

An "un-modified hypervariable region" for the purposes herein is a hypervariable region having the same amino acid sequence as a non-human antibody from which it was derived, i.e. one which lacks one or more amino acid substitutions therein.

The term "hypervariable region", "HVR", or "HV", when used herein refers to the regions of an antibody variable domain which are hypervariable in sequence and/or form structurally defined loops. Generally, antibodies comprise six hypervariable regions; three in the VH (H1, H2, H3), and three in the VL (L1, L2, L3). A number of hypervariable region delineations are in use and are encompassed herein. The Kabat Complementarity Determining Regions (CDRs) are based on sequence variability and are the most commonly used (Kabat et al., *Sequences of Proteins of Immunological Interest,* 5th Ed. Public Health Service, National Institutes of Health, Bethesda, Md. (1991)). Chothia refers instead to the location of the structural loops (Chothia and Lesk *J. Mol. Biol.* 196:901-917 (1987)). The AbM hypervariable regions represent a compromise between the Kabat CDRs and Chothia structural loops, and are used by Oxford Molecular's AbM antibody modeling software. The "contact" hypervariable regions are based on an analysis of the available complex crystal structures. The residues from each of these hypervariable regions are noted below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B |
| | | (Kabat Numbering) | | |
| H1 | H31-H35 | H26-H35 | H26-H32 | H30-H35 |
| | | (Chothia Numbering) | | |
| H2 | H50-H65 | H50-H58 | H53-H55 | H47-H58 |
| H3 | H95-H102 | H95-H102 | H96-H101 | H93-H101 |

Hypervariable regions may comprise "extended hypervariable regions" as follows: 24-36 or 24-34 (L1), 46-56 or 50-56 (L2) and 89-97 (L3) in the VL and 26-35 (H1), 50-65 or 49-65 (H2) and 93-102, 94-102 or 95-102 (H3) in the VH. The variable domain residues are numbered according to Kabat et al., supra for each of these definitions.

"Framework" or "FR" residues are those variable domain residues other than the hypervariable region residues as herein defined.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues.

An "affinity matured" antibody is one with one or more alterations in one or more CDRs thereof which result in an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. *Bio/technology* 10:779-783 (1992) describes affinity maturation by VH and VL domain shuffling. Random mutagenesis of CDR and/or framework residues is described by: Barbas et al. *Proc Nat. Acad. Sci, USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

A "blocking" antibody or an "antagonist" antibody is one which inhibits or reduces biological activity of the antigen it bind. Preferred blocking antibodies or antagonist antibodies substantially or completely inhibit the biological activity of the antigen.

An "agonist antibody", as used herein, is an antibody which mimics at least one of the functional activities of a polypeptide of interest.

A "disorder" is any condition that would benefit from treatment with a substance/molecule or method of the invention. This includes chronic and acute disorders or diseases including those pathological conditions which predispose the mammal to the disorder in question. Non-limiting examples of disorders to be treated herein include malignant and benign tumors; non-leukemias and lymphoid malignancies; neuronal, glial, astrocytal, hypothalamic and other glandular, macrophagal, epithelial, stromal and blastocoelic disorders; and inflammatory, immunologic and other angiogenesis-related disorders.

The terms "cell proliferative disorder" and "proliferative disorder" refer to disorders that are associated with some degree of abnormal cell proliferation. In one embodiment, the cell proliferative disorder is cancer.

"Tumor", as used herein, refers to all neoplastic cell growth and proliferation, whether malignant or benign, and all precancerous and cancerous cells and tissues. The terms "cancer", "cancerous", "cell proliferative disorder", "proliferative disorder" and "tumor" are not mutually exclusive as referred to herein.

The terms "cancer" and "cancerous" refer to or describe the physiological condition in mammals that is typically characterized by unregulated cell growth/proliferation. Examples of cancer include but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancer.

Dysregulation of angiogenesis can lead to many disorders that can be treated by compositions and methods of the invention. These disorders include both non-neoplastic and neoplastic conditions. Neoplastics include but are not limited those described above. Non-neoplastic disorders include but are not limited to undesired or aberrant hypertrophy, arthritis, rheumatoid arthritis (RA), psoriasis, psoriatic plaques, sarcoidosis, atherosclerosis, atherosclerotic plaques, diabetic and other proliferative retinopathies including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, chronic inflammation, lung inflammation, acute lung injury/ARDS, sepsis, primary pulmonary hypertension, malignant pulmonary effusions, cerebral edema (e.g., associated with acute stroke/closed head injury/trauma), synovial inflammation, pannus formation in RA, myositis ossificans, hypertropic bone formation, osteoarthritis (OA), refractory ascites, polycystic ovarian disease, endometriosis, 3rd spacing of fluid diseases (pancreatitis, compartment syndrome, burns, bowel disease), uterine fibroids, premature labor, chronic inflammation such as IBD (Crohn's disease and ulcerative colitis), renal allograft rejection, inflammatory bowel disease, nephrotic syndrome, undesired or aberrant tissue mass growth (non-cancer), hemophilic joints, hypertrophic scars, inhibition of hair growth, Osler-Weber syndrome, pyogenic granuloma retrolental fibroplasias, scleroderma, trachoma, vascular adhesions, synovitis, dermatitis, preeclampsia, ascites, pericardial effusion (such as that associated with pericarditis), and pleural effusion.

As used herein, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or disorder.

An "effective amount" refers to an amount effective, at dosages and for periods of time necessary, to achieve the desired therapeutic or prophylactic result.

A "therapeutically effective amount" of a substance/molecule of the invention, agonist or antagonist may vary according to factors such as the disease state, age, sex, and weight of the individual, and the ability of the substance/molecule, agonist or antagonist to elicit a desired response in the individual. A therapeutically effective amount is also one in which any toxic or detrimental effects of the substance/molecule, agonist or antagonist are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents e.g. methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "chemotherapeutic agent" is a chemical compound useful in the treatment of cancer. Examples of chemotherapeutic agents include alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1 I and calicheamicin omegaI1 (see, e.g., Agnew, *Chem Intl. Ed. Engl.*, 33: 183-186 (1994)); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhône-Poulenc Rorer, Antony, France); chloranbucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylornithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Also included in this definition are anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), EVISTA® raloxifene, droloxifene, 4-hydroxytamoxifen, trioxifene, keoxifene, LY117018, onapristone, and FARESTON® toremifene; anti-progesterones; estrogen receptor down-regulators (ERDs); agents that function to suppress or shut down the ovaries, for example, leutinizing hormone-releasing hormone (LHRH) agonists such as LUPRON® and ELIGARD® leuprolide acetate, goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole. In addition, such definition of chemotherapeutic agents includes bisphosphonates such as clodronate (for example, BONEFOS® or OSTAC®), DIDROCAL® etidronate, NE-58095, ZOMETA® zoledronic acid/zoledronate, FOSAMAX® alendronate, AREDIA® pamidronate, SKELID® tiludronate, or ACTONEL® risedronate; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; LURTOTECAN® topoisomerase 1 inhibitor; ABARELIX® rmRH; lapatinib ditosylate (an ErbB-2 and EGFR dual tyrosine kinase small-molecule inhibitor also known as GW572016); and pharmaceutically acceptable salts, acids or derivatives of any of the above.

A "growth inhibitory agent" when used herein refers to a compound or composition which inhibits growth of a cell whose growth is dependent upon HGF/c-met activation either in vitro or in vivo. Thus, the growth inhibitory agent may be one which significantly reduces the percentage of HGF/c-met-dependent cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

"Doxorubicin" is an anthracycline antibiotic. The full chemical name of doxorubicin is (8S-cis)-10-[(3-amino-2,3, 6-trideoxy-α-L-lyxo-hexapyranosyl)oxy]-7,8,9,10-tetrahydro-6,8,11-trihydroxy-8-(hydroxyacetyl)-1-methoxy-5,12-naphthacenedione.

Generating Variant Antibodies Exhibiting Reduced or Absence of HAMA Response

Reduction or elimination of a HAMA response is a significant aspect of clinical development of suitable therapeutic agents. See, e.g., Khaxzaeli et al., J. Natl. Cancer Inst. (1988), 80:937; Jaffers et al., Transplantation (1986), 41:572; Shawler et al., J. Immunol. (1985), 135:1530; Sears et al., J. Biol. Response Mod. (1984), 3:138; Miller et al., Blood (1983), 62:988; Hakimi et al., J. Immunol. (1991), 147:1352; Reichmann et al., Nature (1988), 332:323; Junghans et al., Cancer Res. (1990), 50:1495. As described herein, the invention provides antibodies that are humanized such that HAMA response is reduced or eliminated. Variants of these antibodies can further be obtained using routine methods known in the art, some of which are further described below.

For example, an amino acid sequence from an antibody as described herein can serve as a starting (parent) sequence for diversification of the framework and/or hypervariable sequence(s). A selected framework sequence to which a starting hypervariable sequence is linked is referred to herein as an acceptor human framework. While the acceptor human frameworks may be from, or derived from, a human immunoglobulin (the VL and/or VH regions thereof), preferably the acceptor human frameworks are from, or derived from, a human consensus framework sequence as such frameworks have been demonstrated to have minimal, or no, immunogenicity in human patients.

Where the acceptor is derived from a human immunoglobulin, one may optionally select a human framework sequence that is selected based on its homology to the donor framework sequence by aligning the donor framework sequence with various human framework sequences in a collection of human framework sequences, and select the most homologous framework sequence as the acceptor.

In one embodiment, human consensus frameworks herein are from, or derived from, VH subgroup III and/or VL kappa subgroup I consensus framework sequences.

Thus, the VH acceptor human framework may comprise one, two, three or all of the following framework sequences:

FR1 comprising EVQLVESGGGLVQPGGSLRLSCAAS (SEQ ID NO:42),

FR2 comprising WVRQAPGKGLEWV (SEQ ID NO:43),

FR3 comprising FR3 comprises RFTISX1DX2SKNTX3YLQMNSLRAEDTAVYYC (SEQ ID NO:50), wherein X1 is A or R, X2 is T or N, and X3 is A or L, FR4 comprising WGQGTLVTVSS (SEQ ID NO:45).

Examples of VH consensus frameworks include:

human VH subgroup I consensus framework minus Kabat CDRs (SEQ ID No: 19);

human VH subgroup I consensus framework minus extended hypervariable regions (SEQ ID NOs:20-22);

human VH subgroup II consensus framework minus Kabat CDRs (SEQ ID NO:23);

human VH subgroup II consensus framework minus extended hypervariable regions (SEQ ID NOs:24-26);

human VH subgroup III consensus framework minus Kabat CDRs (SEQ ID NO:27);

human VH subgroup III consensus framework minus extended hypervariable regions (SEQ ID NO:28-30);

human VH acceptor framework minus Kabat CDRs (SEQ ID NO:31);

human VH acceptor framework minus extended hypervariable regions (SEQ ID NOs:32-33);

human VH acceptor 2 framework minus Kabat CDRs (SEQ ID NO:34); or human VH acceptor 2 framework minus extended hypervariable regions (SEQ ID NOs:35-37).

In one embodiment, the VH acceptor human framework comprises one, two, three or all of the following framework sequences:

FR1 comprising EVQLVESGGGLVQPGGSLRLSCAAS (SEQ ID NO:42),

FR2 comprising WVRQAPGKGLEWV (SEQ ID NO:43),

FR3 comprising RFTISADTSKNTAYLQMNSLRAED-TAVYYC (SEQ ID NO:51),

RFTISADTSKNTAYLQMNSLRAEDTAVYYCA (SEQ ID NO:52),

RFTISADTSKNTAYLQMNSLRAEDTAVYYCAR (SEQ ID NO:53),

RFTISADTSKNTAYLQMNSLRAEDTAVYYCS (SEQ ID NO:54), or

RFTISADTSKNTAYLQMNSLRAEDTAVYYCSR (SEQ ID NO:55)

FR4 comprising WGQGTLVTVSS (SEQ ID NO:45).

The VL acceptor human framework may comprise one, two, three or all of the following framework sequences:

FR1 comprising DIQMTQSPSSLSASVGDRVTITC (SEQ ID NO:46),

FR2 comprising WYQQKPGKAPKLLIY (SEQ ID NO:47),

FR3 comprising GVPSRFSGSGSGTDFTLTISSLQPEDFA-TYYC (SEQ ID NO:48),

FR4 comprising FGQGTKVEIK (SEQ ID NO:49).

Examples of VL consensus frameworks include:

human VL kappa subgroup I consensus framework (SEQ ID NO:38);

human VL kappa subgroup II consensus framework (SEQ ID NO:39);

human VL kappa subgroup III consensus framework (SEQ ID NO:40); or human VL kappa subgroup IV consensus framework (SEQ ID NO:41)

While the acceptor may be identical in sequence to the human framework sequence selected, whether that be from a human immunoglobulin or a human consensus framework, the present invention contemplates that the acceptor sequence may comprise pre-existing amino acid substitutions relative to the human immunoglobulin sequence or human consensus framework sequence. These pre-existing substitutions are preferably minimal; usually four, three, two or one amino acid differences only relative to the human immunoglobulin sequence or consensus framework sequence.

Hypervariable region residues of the non-human antibody are incorporated into the VL and/or VH acceptor human frameworks. For example, one may incorporate residues corresponding to the Kabat CDR residues, the Chothia hypervariable loop residues, the Abm residues, and/or contact residues. Optionally, the extended hypervariable region residues as follows are incorporated: 24-34 (L1), 50-56 (L2) and 89-97 (L3), 26-35 (H1), 50-65 or 49-65 (H2) and 93-102, 94-102, or 95-102 (H3).

While "incorporation" of hypervariable region residues is discussed herein, it will be appreciated that this can be achieved in various ways, for example, nucleic acid encoding the desired amino acid sequence can be generated by mutating nucleic acid encoding the mouse variable domain sequence so that the framework residues thereof are changed to acceptor human framework residues, or by mutating nucleic acid encoding the human variable domain sequence so that the hypervariable domain residues are changed to non-human residues, or by synthesizing nucleic acid encoding the desired sequence, etc.

In the examples herein, hypervariable region-grafted variants were generated by Kunkel mutagenesis of nucleic acid encoding the human acceptor sequences, using a separate oligonucleotide for each hypervariable region. Kunkel et al., Methods Enzymol. 154:367-382 (1987). Appropriate changes can be introduced within the framework and/or hypervariable region, using routine techniques, to correct and re-establish proper hypervariable region-antigen interactions.

Phage(mid) display (also referred to herein as phage display in some contexts) can be used as a convenient and fast method for generating and screening many different potential variant antibodies in a library generated by sequence randomization. However, other methods for making and screening altered antibodies are available to the skilled person.

Phage(mid) display technology has provided a powerful tool for generating and selecting novel proteins which bind to a ligand, such as an antigen. Using the techniques of phage (mid) display allows the generation of large libraries of protein variants which can be rapidly sorted for those sequences that bind to a target molecule with high affinity. Nucleic acids encoding variant polypeptides are generally fused to a nucleic acid sequence encoding a viral coat protein, such as the gene III protein or the gene VIII protein. Monovalent phagemid display systems where the nucleic acid sequence encoding the protein or polypeptide is fused to a nucleic acid sequence encoding a portion of the gene III protein have been developed. (Bass, S., *Proteins,* 8:309 (1990); Lowman and Wells, *Methods: A Companion to Methods in Enzymology,* 3:205 (1991)). In a monovalent phagemid display system, the gene fusion is expressed at low levels and wild type gene III proteins are also expressed so that infectivity of the particles is retained. Methods of generating peptide libraries and screening those libraries have been disclosed in many patents (e.g. U.S. Pat. No. 5,723,286, U.S. Pat. No. 5,432,018, U.S. Pat. No. 5,580,717, U.S. Pat. No. 5,427,908 and U.S. Pat. No. 5,498,530).

Libraries of antibodies or antigen binding polypeptides have been prepared in a number of ways including by altering a single gene by inserting random DNA sequences or by cloning a family of related genes. Methods for displaying antibodies or antigen binding fragments using phage(mid) display have been described in U.S. Pat. Nos. 5,750,373, 5,733,743, 5,837,242, 5,969,108, 6,172,197, 5,580,717, and 5,658,727. The library is then screened for expression of antibodies or antigen binding proteins with the desired characteristics.

Methods of substituting an amino acid of choice into a template nucleic acid are well established in the art, some of which are described herein. For example, hypervariable region residues can be substituted using the Kunkel method. See, e.g., Kunkel et al., *Methods Enzymol.* 154:367-382 (1987).

The sequence of oligonucleotides includes one or more of the designed codon sets for the hypervariable region residues to be altered. A codon set is a set of different nucleotide triplet sequences used to encode desired variant amino acids. Codon sets can be represented using symbols to designate particular nucleotides or equimolar mixtures of nucleotides as shown in below according to the IUB code.

IUB Codes
G Guanine
A Adenine
T Thymine
C Cytosine
R (A or G)
Y (C or T)
M (A or C)
K (G or T)
S (C or G)
W (A or T)
H (A or C or T)
B (C or G or T)
V (A or C or G)
D (A or G or T)
N (A or C or G or T)

For example, in the codon set DVK, D can be nucleotides A or G or T; V can be A or G or C; and K can be G or T. This codon set can present 18 different codons and can encode amino acids Ala, Trp, Tyr, Lys, Thr, Asn, Lys, Ser, Arg, Asp, Glu, Gly, and Cys.

Oligonucleotide or primer sets can be synthesized using standard methods. A set of oligonucleotides can be synthesized, for example, by solid phase synthesis, containing sequences that represent all possible combinations of nucleotide triplets provided by the codon set and that will encode the desired group of amino acids. Synthesis of oligonucleotides with selected nucleotide "degeneracy" at certain positions is well known in that art. Such sets of nucleotides having certain codon sets can be synthesized using commercial nucleic acid synthesizers (available from, for example, Applied Biosystems, Foster City, Calif.), or can be obtained commercially (for example, from Life Technologies, Rockville, Md.). Therefore, a set of oligonucleotides synthesized having a particular codon set will typically include a plurality of oligonucleotides with different sequences, the differences established by the codon set within the overall sequence. Oligonucleotides, as used according to the invention, have sequences that allow for hybridization to a variable domain nucleic acid template and also can include restriction enzyme sites for cloning purposes.

In one method, nucleic acid sequences encoding variant amino acids can be created by oligonucleotide-mediated mutagenesis. This technique is well known in the art as described by Zoller et al. *Nucleic Acids Res.* 10:6487-6504 (1987). Briefly, nucleic acid sequences encoding variant amino acids are created by hybridizing an oligonucleotide set encoding the desired codon sets to a DNA template, where the template is the single-stranded form of the plasmid containing a variable region nucleic acid template sequence. After hybridization, DNA polymerase is used to synthesize an entire second complementary strand of the template that will thus incorporate the oligonucleotide primer, and will contain the codon sets as provided by the oligonucleotide set.

Generally, oligonucleotides of at least 25 nucleotides in length are used. An optimal oligonucleotide will have 12 to 15 nucleotides that are completely complementary to the template on either side of the nucleotide(s) coding for the mutation(s). This ensures that the oligonucleotide will hybridize properly to the single-stranded DNA template molecule. The oligonucleotides are readily synthesized using techniques known in the art such as that described by Crea et al., *Proc. Nat'l. Acad. Sci. USA,* 75:5765 (1978).

The DNA template is generated by those vectors that are either derived from bacteriophage M13 vectors (the commercially available M13mp18 and M13mp19 vectors are suitable), or those vectors that contain a single-stranded phage origin of replication as described by Viera et al., *Meth. Enzymol.,* 153:3 (1987). Thus, the DNA that is to be mutated can be inserted into one of these vectors in order to generate single-stranded template. Production of the single-stranded template is described in sections 4.21-4.41 of Sambrook et al., above.

To alter the native DNA sequence, the oligonucleotide is hybridized to the single stranded template under suitable hybridization conditions. A DNA polymerizing enzyme, usually T7 DNA polymerase or the Klenow fragment of DNA polymerase I, is then added to synthesize the complementary strand of the template using the oligonucleotide as a primer for synthesis. A heteroduplex molecule is thus formed such that one strand of DNA encodes the mutated form of gene 1, and the other strand (the original template) encodes the native, unaltered sequence of gene 1. This heteroduplex molecule is then transformed into a suitable host cell, usually a prokaryote such as E. coli JM101. After growing the cells, they are plated onto agarose plates and screened using the oligonucleotide primer radiolabelled with a 32-Phosphate to identify the bacterial colonies that contain the mutated DNA.

The method described immediately above may be modified such that a homoduplex molecule is created wherein both strands of the plasmid contain the mutation(s). The modifications are as follows: The single stranded oligonucleotide is annealed to the single-stranded template as described above. A mixture of three deoxyribonucleotides, deoxyriboadenosine (dATP), deoxyriboguanosine (dGTP), and deoxyribothymidine (dTT), is combined with a modified thiodeoxyribocytosine called dCTP-(aS) (which can be obtained from Amersham). This mixture is added to the template-oligonucleotide complex. Upon addition of DNA polymerase to this mixture, a strand of DNA identical to the template except for the mutated bases is generated. In addition, this new strand of DNA will contain dCTP-(aS) instead of dCTP, which serves to protect it from restriction endonuclease digestion. After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell.

As indicated previously the sequence of the oligonucleotide set is of sufficient length to hybridize to the template nucleic acid and may also, but does not necessarily, contain restriction sites. The DNA template can be generated by those vectors that are either derived from bacteriophage M13 vectors or vectors that contain a single-stranded phage origin of replication as described by Viera et al. *Meth. Enzymol.,* 153:3 (1987). Thus, the DNA that is to be mutated must be inserted into one of these vectors in order to generate single-stranded template. Production of the single-stranded template is described in sections 4.21-4.41 of Sambrook et al., supra.

According to another method, a library can be generated by providing upstream and downstream oligonucleotide sets, each set having a plurality of oligonucleotides with different sequences, the different sequences established by the codon sets provided within the sequence of the oligonucleotides. The upstream and downstream oligonucleotide sets, along with a variable domain template nucleic acid sequence, can be used in a polymerase chain reaction to generate a "library" of PCR products. The PCR products can be referred to as "nucleic acid cassettes", as they can be fused with other related or unrelated nucleic acid sequences, for example, viral coat proteins and dimerization domains, using established molecular biology techniques.

The sequence of the PCR primers includes one or more of the designed codon sets for the solvent accessible and highly diverse positions in a hypervariable region. As described above, a codon set is a set of different nucleotide triplet sequences used to encode desired variant amino acids.

Antibody selectants that meet the desired criteria, as selected through appropriate screening/selection steps can be isolated and cloned using standard recombinant techniques.

Vectors, Host Cells and Recombinant Methods

For recombinant production of an antibody of the invention, the nucleic acid encoding it is isolated and inserted into a replicable vector for further cloning (amplification of the DNA) or for expression. DNA encoding the antibody is readily isolated and sequenced using conventional procedures (e.g., by using oligonucleotide probes that are capable of binding specifically to genes encoding the heavy and light chains of the antibody). Many vectors are available. The choice of vector depends in part on the host cell to be used. Generally, preferred host cells are of either prokaryotic or eukaryotic (generally mammalian) origin.

Generating Antibodies Using Prokaryotic Host Cells:

Vector Construction

Polynucleotide sequences encoding polypeptide components of the antibody of the invention can be obtained using standard recombinant techniques. Desired polynucleotide sequences may be isolated and sequenced from antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, E. coli is typically transformed using pBR322, a plasmid derived from an E. coli species. pBR322 contains genes encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies are described in detail in Carter et al., U.S. Pat. No. 5,648,237.

In addition, phage vectors containing replicon and control sequences that are compatible with the host microorganism can be used as transforming vectors in connection with these hosts. For example, bacteriophage such as λGEM.TM.-11 may be utilized in making a recombinant vector which can be used to transform susceptible host cells such as E. coli LE392.

The expression vector of the invention may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g. the presence or absence of a nutrient or a change in temperature.

A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector of the invention. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters suitable for use with prokaryotic hosts include the PhoA promoter, the β-galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker operably to ligate them to cistrons encoding the target light and heavy chains (Siebenlist et al. (1980) Cell 20: 269) using linkers or adaptors to supply any required restriction sites.

In one aspect of the invention, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e. cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, Ipp, or heat-stable enterotoxin II (STII) leaders, LamB, PhoE, PelB, OmpA and MBP. In one embodiment of the invention, the signal sequences used in both cistrons of the expression system are STII signal sequences or variants thereof.

In another aspect, the production of the immunoglobulins according to the invention can occur in the cytoplasm of the host cell, and therefore does not require the presence of secretion signal sequences within each cistron. In that regard, immunoglobulin light and heavy chains are expressed, folded and assembled to form functional immunoglobulins within the cytoplasm. Certain host strains (e.g., the *E. coli* trxB⁻ strains) provide cytoplasm conditions that are favorable for disulfide bond formation, thereby permitting proper folding and assembly of expressed protein subunits. Proba and Pluckthun *Gene,* 159:203 (1995).

The present invention provides an expression system in which the quantitative ratio of expressed polypeptide components can be modulated in order to maximize the yield of secreted and properly assembled antibodies of the invention. Such modulation is accomplished at least in part by simultaneously modulating translational strengths for the polypeptide components.

One technique for modulating translational strength is disclosed in Simmons et al., U.S. Pat. No. 5,840,523. It utilizes variants of the translational initiation region (TIR) within a cistron. For a given TIR, a series of amino acid or nucleic acid sequence variants can be created with a range of translational strengths, thereby providing a convenient means by which to adjust this factor for the desired expression level of the specific chain. TIR variants can be generated by conventional mutagenesis techniques that result in codon changes which can alter the amino acid sequence, although silent changes in the nucleotide sequence are preferred. Alterations in the TIR can include, for example, alterations in the number or spacing of Shine-Dalgarno sequences, along with alterations in the signal sequence. One method for generating mutant signal sequences is the generation of a "codon bank" at the beginning of a coding sequence that does not change the amino acid sequence of the signal sequence (i.e., the changes are silent). This can be accomplished by changing the third nucleotide position of each codon; additionally, some amino acids, such as leucine, serine, and arginine, have multiple first and second positions that can add complexity in making the bank. This method of mutagenesis is described in detail in Yansura et al. (1992) *METHODS: A Companion to Methods in Enzymol.* 4:151-158.

Preferably, a set of vectors is generated with a range of TIR strengths for each cistron therein. This limited set provides a comparison of expression levels of each chain as well as the yield of the desired antibody products under various TIR strength combinations. TIR strengths can be determined by quantifying the expression level of a reporter gene as described in detail in Simmons et al. U.S. Pat. No. 5,840,523. Based on the translational strength comparison, the desired individual TIRs are selected to be combined in the expression vector constructs of the invention.

Prokaryotic host cells suitable for expressing antibodies of the invention include Archaebacteria and Eubacteria, such as Gram-negative or Gram-positive organisms. Examples of useful bacteria include *Escherichia* (e.g., *E. coli*), *Bacilli* (e.g., *B. subtilis*), *Enterobacteria, Pseudomonas* species (e.g., *P. aeruginosa*), *Salmonella typhimurium, Serratia marcescans, Klebsiella, Proteus, Shigella, Rhizobia, Vitreoscilla,* or *Paracoccus*. In one embodiment, gram-negative cells are used. In one embodiment, *E. coli* cells are used as hosts for the invention. Examples of *E. coli* strains include strain W3110 (Bachmann, *Cellular and Molecular Biology,* vol. 2 (Washington, D.C.: American Society for Microbiology, 1987), pp. 1190-1219; ATCC Deposit No. 27,325) and derivatives thereof, including strain 33D3 having genotype W3110 ΔfhuA (ΔtonA) ptr3 lac Iq lacL8 ΔompTΔ(nmpc-fepE) degP41 kan$^R$ (U.S. Pat. No. 5,639,635). Other strains and derivatives thereof, such as *E. coli* 294 (ATCC 31,446), *E. coli* B, *E. coli*$_\lambda$ 1776 (ATCC 31,537) and *E. coli* RV308 (ATCC 31,608) are also suitable. These examples are illustrative rather than limiting. Methods for constructing derivatives of any of the above-mentioned bacteria having defined genotypes are known in the art and described in, for example, Bass et al., *Proteins,* 8:309-314 (1990). It is generally necessary to select the appropriate bacteria taking into consideration replicability of the replicon in the cells of a bacterium. For example, *E. coli, Serratia,* or *Salmonella* species can be suitably used as the host when well known plasmids such as pBR322, pBR325, pACYC177, or pKN410 are used to supply the replicon. Typically the host cell should secrete minimal amounts of proteolytic enzymes, and additional protease inhibitors may desirably be incorporated in the cell culture.

Antibody Production

Host cells are transformed with the above-described expression vectors and cultured in conventional nutrient media modified as appropriate for inducing promoters, selecting transformants, or amplifying the genes encoding the desired sequences.

Transformation means introducing DNA into the prokaryotic host so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the polypeptides of the invention are grown in media known in the art and suitable for culture of the selected host cells. Examples of suitable media include luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. For *E. coli* growth, for example, the preferred temperature ranges from about 20° C. to about 39° C., more preferably from about 25° C. to about 37° C., even more preferably at about 30° C. The pH of the medium may be any pH ranging from about 5 to about 9, depending mainly on the host organism. For *E. coli*, the pH is preferably from about 6.8 to about 7.4, and more preferably about 7.0.

If an inducible promoter is used in the expression vector of the invention, protein expression is induced under conditions suitable for the activation of the promoter. In one aspect of the invention, PhoA promoters are used for controlling transcription of the polypeptides. Accordingly, the transformed host cells are cultured in a phosphate-limiting medium for induction. Preferably, the phosphate-limiting medium is the C.R.A.P medium (see, e.g., Simmons et al., *J. Immunol. Methods* (2002), 263:133-147). A variety of other inducers may be used, according to the vector construct employed, as is known in the art.

In one embodiment, the expressed polypeptides of the present invention are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

In one aspect of the invention, antibody production is conducted in large quantity by a fermentation process. Various large-scale fed-batch fermentation procedures are available for production of recombinant proteins. Large-scale fermentations have at least 1000 liters of capacity, preferably about 1,000 to 100,000 liters of capacity. These fermentors use agitator impellers to distribute oxygen and nutrients, especially glucose (the preferred carbon/energy source). Small scale fermentation refers generally to fermentation in a fermentor that is no more than approximately 100 liters in volumetric capacity, and can range from about 1 liter to about 100 liters.

In a fermentation process, induction of protein expression is typically initiated after the cells have been grown under suitable conditions to a desired density, e.g., an $OD_{550}$ of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the polypeptides of the invention, various fermentation conditions can be modified. For example, to improve the proper assembly and folding of the secreted antibody polypeptides, additional vectors overexpressing chaperone proteins, such as Dsb proteins (DsbA, DsbB, DsbC, DsbD and or DsbG) or FkpA (a peptidylprolyl cis,trans-isomerase with chaperone activity) can be used to co-transform the host prokaryotic cells. The chaperone proteins have been demonstrated to facilitate the proper folding and solubility of heterologous proteins produced in bacterial host cells. Chen et al. (1999) *J Bio Chem* 274:19601-19605; Georgiou et al., U.S. Pat. No. 6,083,715; Georgiou et al., U.S. Pat. No. 6,027,888; Bothmann and Pluckthun (2000) *J. Biol. Chem.* 275:17100-17105; Ramm and Pluckthun (2000) *J. Biol. Chem.* 275:17106-17113; Arie et al. (2001) *Mol. Microbiol.* 39:199-210.

To minimize proteolysis of expressed heterologous proteins (especially those that are proteolytically sensitive), certain host strains deficient for proteolytic enzymes can be used for the present invention. For example, host cell strains may be modified to effect genetic mutation(s) in the genes encoding known bacterial proteases such as Protease III, OmpT, DegP, Tsp, Protease I, Protease Mi, Protease V, Protease VI and combinations thereof. Some *E. coli* protease-deficient strains are available and described in, for example, Joly et al. (1998), supra; Georgiou et al., U.S. Pat. No. 5,264,365; Georgiou et al., U.S. Pat. No. 5,508,192; Hara et al., *Microbial Drug Resistance*, 2:63-72 (1996).

In one embodiment, *E. coli* strains deficient for proteolytic enzymes and transformed with plasmids overexpressing one or more chaperone proteins are used as host cells in the expression system of the invention.

Antibody Purification

In one embodiment, the antibody protein produced herein is further purified to obtain preparations that are substantially homogeneous for further assays and uses. Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

In one aspect, Protein A immobilized on a solid phase is used for immunoaffinity purification of the full length antibody products of the invention. Protein A is a 41 kD cell wall protein from *Staphylococcus aureas* which binds with a high affinity to the Fc region of antibodies. Lindmark et al (1983) *J. Immunol. Meth.* 62:1-13. The solid phase to which Protein A is immobilized is preferably a column comprising a glass or silica surface, more preferably a controlled pore glass column or a silicic acid column. In some applications, the column has been coated with a reagent, such as glycerol, in an attempt to prevent nonspecific adherence of contaminants.

As the first step of purification, the preparation derived from the cell culture as described above is applied onto the Protein A immobilized solid phase to allow specific binding of the antibody of interest to Protein A. The solid phase is then washed to remove contaminants non-specifically bound to the solid phase. Finally the antibody of interest is recovered from the solid phase by elution.

Generating Antibodies Using Eukaryotic Host Cells:

The vector components generally include, but are not limited to, one or more of the following: a signal sequence, an origin of replication, one or more marker genes, an enhancer element, a promoter, and a transcription termination sequence.

(i) Signal Sequence Component

A vector for use in a eukaryotic host cell may also contain a signal sequence or other polypeptide having a specific cleavage site at the N-terminus of the mature protein or polypeptide of interest. The heterologous signal sequence selected preferably is one that is recognized and processed (i.e., cleaved by a signal peptidase) by the host cell. In mammalian cell expression, mammalian signal sequences as well as viral secretory leaders, for example, the herpes simplex gD signal, are available.

The DNA for such precursor region is ligated in reading frame to DNA encoding the antibody.

(ii) Origin of Replication

Generally, an origin of replication component is not needed for mammalian expression vectors. For example, the SV40 origin may typically be used only because it contains the early promoter.

(iii) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, where relevant, or (c) supply critical nutrients not available from complex media.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the antibody nucleic acid, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., ATCC CRL-9096).

Alternatively, host cells (particularly wild-type hosts that contain endogenous DHFR) transformed or co-transformed with DNA sequences encoding an antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

(iv) Promoter Component

Expression and cloning vectors usually contain a promoter that is recognized by the host organism and is operably linked to the antibody polypeptide nucleic acid. Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Antibody polypeptide transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., *Nature* 297:598-601 (1982) on expression of human β-interferon cDNA in mouse cells under the control of a thymidine kinase promoter from herpes simplex virus. Alternatively, the Rous Sarcoma Virus long terminal repeat can be used as the promoter.

(v) Enhancer Element Component

Transcription of DNA encoding the antibody polypeptide of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, *Nature* 297:17-18 (1982) on enhancing elements for activation of eukaryotic promoters. The enhancer may be spliced into the vector at a position 5' or 3' to the antibody polypeptide-encoding sequence, but is preferably located at a site 5' from the promoter.

(vi) Transcription Termination Component

Expression vectors used in eukaryotic host cells will typically also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding an antibody. One useful transcription termination component is the bovine growth hormone polyadenylation region. See WO94/11026 and the expression vector disclosed therein.

(vii) Selection and Transformation of Host Cells

Suitable host cells for cloning or expressing the DNA in the vectors herein include higher eukaryote cells described herein, including vertebrate host cells. Propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/-DHFR (CHO, Urlaub et al., *Proc. Natl. Acad. Sci. USA* 77:4216 (1980)); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and a human hepatoma line (Hep G2).

Host cells are transformed with the above-described expression or cloning vectors for antibody production and cultured in conventional nutrient media modified as appropriate for inducing promoters, selecting transformants, or amplifying the genes encoding the desired sequences.

(viii) Culturing the Host Cells

The host cells used to produce an antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

(ix) Purification of Antibody

When using recombinant techniques, the antibody can be produced intracellularly, or directly secreted into the medium. If the antibody is produced intracellularly, as a first step, the particulate debris, either host cells or lysed fragments, are removed, for example, by centrifugation or ultrafiltration. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.* 62:1-13 (1983)). Protein G is recommended for all mouse isotypes and for human γ3 (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

Activity Assays

The antibodies of the present invention can be characterized for their physical/chemical properties and biological functions by various assays known in the art.

The purified immunoglobulins can be further characterized by a series of assays including, but not limited to, N-terminal sequencing, amino acid analysis, non-denaturing size exclusion high pressure liquid chromatography (HPLC), mass spectrometry, ion exchange chromatography and papain digestion.

In certain embodiments of the invention, the immunoglobulins produced herein are analyzed for their biological activity. In some embodiments, the immunoglobulins of the present invention are tested for their antigen binding activity. The antigen binding assays that are known in the art and can be used herein include without limitation any direct or competitive binding assays using techniques such as western blots, radioimmunoassays, ELISA (enzyme linked immunosorbent assay), "sandwich" immunoassays, immunoprecipitation assays, fluorescent immunoassays, and protein A immunoassays. An illustrative antigen binding assay is provided below in the Examples section.

In one embodiment, the present invention contemplates an altered antibody that possesses some but not all effector functions, which make it a desired candidate for many applications in which the half life of the antibody in vivo is important yet certain effector functions (such as complement and ADCC) are unnecessary or deleterious. In certain embodiments, the Fc activities of the produced immunoglobulin are measured to ensure that only the desired properties are maintained. In vitro and/or in vivo cytotoxicity assays can be conducted to confirm the reduction/depletion of CDC and/or ADCC activities. For example, Fc receptor (FcR) binding assays can be conducted to ensure that the antibody lacks Fc'γR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol* 9:457-92 (1991). An example of an in vitro assay to assess ADCC activity of a molecule of interest is described in U.S. Pat. No. 5,500,362 or U.S. Pat. No. 5,821,337. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *PNAS (USA)* 95:652-656 (1998). C1q binding assays may also be carried out to confirm that the antibody is unable to bind C1q and hence lacks CDC activity. To assess complement activation, a CDC assay, e.g. as described in Gazzano-Santoro et al., *J. Immunol. Methods* 202:163 (1996), may be performed. FcRn binding and in vivo clearance/half life determinations can also be performed using methods known in the art, e.g. those described in the Examples section.

Humanized Antibodies

The present invention encompasses humanized antibodies. Various methods for humanizing non-human antibodies are known in the art. For example, a humanized antibody can have one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al. (1986) *Nature* 321:522-525; Riechmann et al. (1988) *Nature* 332:323-327; Verhoeyen et al. (1988) *Science* 239:1534-1536), by substituting non-human hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework for the humanized antibody (Sims et al. (1993) *J. Immunol.* 151:2296; Chothia et al. (1987) *J. Mol. Biol.* 196:901. Another method uses a particular framework derived from the consensus sequence of all human antibodies of a particular subgroup of light or heavy chains. The same framework may be used for several different humanized antibodies (Carter et al. (1992) *Proc. Natl. Acad. Sci. USA*, 89:4285; Presta et al. (1993) *J. Immunol.*, 151:2623).

It is further important that antibodies be humanized with retention of high affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Antibody Variants

In one aspect, the invention provides antibody fragment comprising modifications in the interface of Fc polypeptides comprising the Fc region, wherein the modifications facilitate and/or promote heterodimerization. These modifications comprise introduction of a protuberance into a first Fc polypeptide and a cavity into a second Fc polypeptide, wherein the protuberance is positionable in the cavity so as to promote complexing of the first and second Fc polypeptides. Methods of generating antibodies with these modifications are known in the art, e.g., as described in U.S. Pat. No. 5,731,168.

In some embodiments, amino acid sequence modification(s) of the antibodies described herein are contemplated. For example, it may be desirable to improve the binding affinity and/or other biological properties of the antibody. Amino acid sequence variants of the antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics. The amino acid alterations may be introduced in the subject antibody amino acid sequence at the time that sequence is made.

A useful method for identification of certain residues or regions of the antibody that are preferred locations for mutagenesis is called "alanine scanning mutagenesis" as described by Cunningham and Wells (1989) *Science*, 244: 1081-1085. Here, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed immunoglobulins are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody to an enzyme (e.g. for ADEPT) or a polypeptide which increases the serum half-life of the antibody.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Conservative substitutions are shown in Table 2 under the heading of "preferred substitutions". If such substitutions result in a change in biological activity, then more substantial changes, denominated "exemplary substitutions" in Table 2, or as further described below in reference to amino acid classes, may be introduced and the products screened.

TABLE 2

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Amino acids may be grouped according to similarities in the properties of their side chains (in A. L. Lehninger, in Biochemistry, second ed., pp. 73-75, Worth Publishers, New York (1975)):

(1) non-polar: Ala (A), Val (V), Leu (L), Ile (I), Pro (P), Phe (F), Trp (W), Met (M)

(2) uncharged polar: Gly (G), Ser (S), Thr (T), Cys (C), Tyr (Y), Asn (N), Gln (Q)

(3) acidic: Asp (D), Glu (E)

(4) basic: Lys (K), Arg (R), His (H)

Alternatively, naturally occurring residues may be divided into groups based on common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class. Such substituted residues also may be introduced into the conservative substitution sites or, more preferably, into the remaining (non-conserved) sites.

One type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g. 6-7 sites) are mutated to generate all possible amino acid substitutions at each site. The antibodies thus generated are displayed from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to introduce one or more amino acid modifications in an Fc region of the immunoglobulin polypeptides of the invention, thereby generating a Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions including that of a hinge cysteine.

In accordance with this description and the teachings of the art, it is contemplated that in some embodiments, an antibody used in methods of the invention may comprise one or more alterations as compared to the wild type counterpart antibody, e.g. in the Fc region. These antibodies would nonetheless retain substantially the same characteristics required for therapeutic utility as compared to their wild type counterpart. For example, it is thought that certain alterations can be made in the Fc region that would result in altered (i.e., either improved or diminished) C1q binding and/or Complement Dependent Cytotoxicity (CDC), e.g., as described in WO99/51642. See also Duncan & Winter Nature 322:738-40 (1988); U.S. Pat. No. 5,648,260; U.S. Pat. No. 5,624,821; and WO94/29351 concerning other examples of Fc region variants.

Immunoconjugates

The invention also pertains to immunoconjugates, or antibody-drug conjugates (ADC), comprising an antibody conjugated to a cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate).

The use of antibody-drug conjugates for the local delivery of cytotoxic or cytostatic agents, i.e. drugs to kill or inhibit tumor cells in the treatment of cancer (Syrigos and Epenetos (1999) Anticancer Research 19:605-614; Niculescu-Duvaz and Springer (1997) Adv. Drg Del. Rev. 26:151-172; U.S. Pat. No. 4,975,278) theoretically allows targeted delivery of the drug moiety to tumors, and intracellular accumulation therein, where systemic administration of these unconjugated drug agents may result in unacceptable levels of toxicity to normal cells as well as the tumor cells sought to be eliminated (Baldwin et al., (1986) Lancet pp. (Mar. 15, 1986):603-05; Thorpe, (1985) "Antibody Carriers Of Cytotoxic Agents In Cancer Therapy: A Review," in Monoclonal Antibodies '84: Biological And Clinical Applications, A. Pinchera et al. (ed.s), pp. 475-506). Maximal efficacy with minimal toxicity is sought thereby. Both polyclonal antibodies and monoclonal antibodies have been reported as useful in these strategies (Rowland et al., (1986) Cancer Immunol. Immunother., 21:183-87). Drugs used in these methods include daunomycin, doxorubicin, methotrexate, and vindesine (Rowland et al., (1986) supra). Toxins used in antibody-toxin conjugates include bacterial toxins such as diphtheria toxin, plant toxins such as ricin, small molecule toxins such as geldanamycin (Mandler et al (2000) Jour. of the Nat. Cancer Inst. 92(19): 1573-1581; Mandler et al (2000) Bioorganic & Med. Chem. Letters 10:1025-1028; Mandler et al (2002) Bioconjugate Chem. 13:786-791), maytansinoids (EP 1391213; Liu et al., (1996) Proc. Natl. Acad. Sci. USA 93:8618-8623), and calicheamicin (Lode et al (1998) Cancer Res. 58:2928; Hinman et al (1993) Cancer Res. 53:3336-3342). The toxins may effect their cytotoxic and cytostatic effects by mechanisms including tubulin binding, DNA binding, or topoisomerase inhibition. Some cytotoxic drugs tend to be inactive or less active when conjugated to large antibodies or protein receptor ligands.

ZEVALIN® (ibritumomab tiuxetan, Biogen/Idec) is an antibody-radioisotope conjugate composed of a murine IgG1 kappa monoclonal antibody directed against the CD20 antigen found on the surface of normal and malignant B lymphocytes and $^{111}$In or $^{90}$Y radioisotope bound by a thiourea linker-chelator (Wiseman et al (2000) Eur. Jour. Nucl. Med. 27(7):766-77; Wiseman et al (2002) Blood 99(12):4336-42; Witzig et al (2002) J. Clin. Oncol. 20(10):2453-63; Witzig et al (2002) J. Clin. Oncol. 20(15):3262-69). Although ZEVALIN has activity against B-cell non-Hodgkin's Lymphoma (NHL), administration results in severe and prolonged cytopenias in most patients. MYLOTARG™ (gemtuzumab ozogamicin, Wyeth Pharmaceuticals), an antibody drug conjugate composed of a hu CD33 antibody linked to calicheamicin, was approved in 2000 for the treatment of acute myeloid leukemia by injection (Drugs of the Future (2000) 25(7):686; U.S. Pat. Nos. 4,970,198; 5,079,233; 5,585,089; 5,606,040; 5,693,762; 5,739,116; 5,767,285; 5,773,001). Cantuzumab mertansine (Immunogen, Inc.), an antibody drug conjugate composed of the huC242 antibody linked via the disulfide linker SPP to the maytansinoid drug moiety, DM1, is advancing into Phase II trials for the treatment of cancers that express CanAg, such as colon, pancreatic, gastric, and others. MLN-2704 (Millennium Pharm., BZL Biologics, Immunogen Inc.), an antibody drug conjugate composed of the anti-prostate specific membrane antigen (PSMA) monoclonal antibody linked to the maytansinoid drug moiety, DM1, is under development for the potential treatment of prostate tumors. The auristatin peptides, auristatin E (AE) and monomethylauristatin (MMAE), synthetic analogs of dolastatin, were conjugated to chimeric monoclonal antibodies cBR96 (specific to Lewis Y on carcinomas) and cAC10 (specific to CD30 on hematological malignancies) (Doronina et al (2003) Nature Biotechnology 21(7):778-784) and are under therapeutic development.

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science*, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Conjugates of an antibody and one or more small molecule toxins, such as a calicheamicin, maytansinoids, a trichothecene, and CC1065, and the derivatives of these toxins that have toxin activity, are also contemplated herein.

Maytansine and Maytansinoids

In one embodiment, an antibody (full length or fragments) of the invention is conjugated to one or more maytansinoid molecules.

Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533, the disclosures of which are hereby expressly incorporated by reference.

Maytansinoid-Antibody Conjugates

In an attempt to improve their therapeutic index, maytansine and maytansinoids have been conjugated to antibodies specifically binding to tumor cell antigens. Immunoconjugates containing maytansinoids and their therapeutic use are disclosed, for example, in U.S. Pat. Nos. 5,208,020, 5,416,064 and European Patent EP 0 425 235 B1, the disclosures of which are hereby expressly incorporated by reference. Liu et al., *Proc. Natl. Acad. Sci. USA* 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al., *Cancer Research* 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansonoid conjugate was tested in vitro on the human breast cancer cell line SK-BR-3, which expresses $3 \times 10^5$ HER-2 surface antigens per cell. The drug conjugate achieved a degree of cytotoxicity similar to the free maytansinoid drug, which could be increased by increasing the number of maytansinoid molecules per antibody molecule. The A7-maytansinoid conjugate showed low systemic cytotoxicity in mice.

Antibody-Maytansinoid Conjugates (Immunoconjugates)

Antibody-maytansinoid conjugates are prepared by chemically linking an antibody to a maytansinoid molecule without significantly diminishing the biological activity of either the antibody or the maytansinoid molecule. An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B1, and Chari et al., *Cancer Research* 52:127-131 (1992). The linking groups include disulfide groups, thioether groups, acid labile groups, photolabile groups, peptidase labile groups, or esterase labile groups, as disclosed in the above-identified patents, disulfide and thioether groups being preferred.

Conjugates of the antibody and maytansinoid may be made using a variety of bifunctional protein coupling agents such as N-succinimidyl-3-(2-pyridyldithio)propionate (SPDP), succinimidyl-4-(N-maleimidomethyl)cyclohexane-1-carboxylate, iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particularly preferred coupling agents include N-succinimidyl-3-(2-pyridyldithio)propionate (SPDP) (Carlsson et al., *Biochem. J.* 173:723-737 [1978]) and N-succinimidyl-4-(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. In a preferred embodiment, the linkage is formed at the C-3 position of maytansinol or a maytansinol analogue.

Calicheamicin

Another immunoconjugate of interest comprises an antibody conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, $\gamma_1^I$, $\alpha_2^I$, $\alpha_3^I$, N-acetyl-$\gamma_1^I$, PSAG and $\theta^I_1$ (Hinman et al., *Cancer Research* 53:3336-3342 (1993), Lode et al., *Cancer Research* 58:2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Other Cytotoxic Agents

Other antitumor agents that can be conjugated to the antibodies of the invention include BCNU, streptozoicin, vincristine and 5-fluorouracil, the family of agents known collectively LL-E33288 complex described in U.S. Pat. Nos. 5,053, 394, 5,770,710, as well as esperamicins (U.S. Pat. No. 5,877, 296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for detection, it may comprise a radioactive atom for scintigraphic studies, for example $tc^{99m}$ or $I^{123}$, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99m}$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al (1978) Biochem. Biophys. Res. Commun. 80: 49-57 can be used to incorporate iodine-123. "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl-3-(2-pyridyldithio)propionate (SPDP), succinimidyl-4-(N-maleimidomethyl)cyclohexane-1-carboxylate, iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., Cancer Research 52:127-131 (1992); U.S. Pat. No. 5,208,020) may be used.

The compounds of the invention expressly contemplate, but are not limited to, ADC prepared with cross-linker reagents: BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A). See pages 467-498, 2003-2004 Applications Handbook and Catalog.

Preparation of Antibody Drug Conjugates

In the antibody drug conjugates (ADC) of the invention, an antibody (Ab) is conjugated to one or more drug moieties (D), e.g. about 1 to about 20 drug moieties per antibody, through a linker (L). The ADC of Formula I may be prepared by several routes, employing organic chemistry reactions, conditions, and reagents known to those skilled in the art, including: (1) reaction of a nucleophilic group of an antibody with a bivalent linker reagent, to form Ab-L, via a covalent bond, followed by reaction with a drug moiety D; and (2) reaction of a nucleophilic group of a drug moiety with a bivalent linker reagent, to form D-L, via a covalent bond, followed by reaction with the nucleophilic group of an antibody.

Ab-(L-D)$_p$    I

Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol.

Antibody drug conjugates of the invention may also be produced by modification of the antibody to introduce electrophilic moieties, which can react with nucleophilic substituents on the linker reagent or drug. The sugars of glycosylated antibodies may be oxidized, e.g. with periodate oxidizing reagents, to form aldehyde or ketone groups which may react with the amine group of linker reagents or drug moieties. The resulting imine Schiff base groups may form a stable linkage, or may be reduced, e.g. by borohydride reagents to form stable amine linkages. In one embodiment, reaction of the carbohydrate portion of a glycosylated antibody with either galactose oxidase or sodium meta-periodate may yield carbonyl (aldehyde and ketone) groups in the protein that can react with appropriate groups on the drug (Hermanson, *Bioconjugate Techniques*). In another embodiment, proteins containing N-terminal serine or threonine residues can react with sodium meta-periodate, resulting in production of an aldehyde in place of the first amino acid (Geoghegan & Stroh, (1992) Bioconjugate Chem. 3:138-146; U.S. Pat. No. 5,362,852). Such aldehyde can be reacted with a drug moiety or linker nucleophile.

Likewise, nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

Alternatively, a fusion protein comprising the antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

In yet another embodiment, the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

Antibody Derivatives

The antibodies of the present invention can be further modified to contain additional nonproteinaceous moieties that are known in the art and readily available. Preferably, the moieties suitable for derivatization of the antibody are water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly (n-vinyl pyrrolidone)polyethylene glycol, propropylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymers are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

Pharmaceutical Formulations

Therapeutic formulations comprising an antibody of the invention are prepared for storage by mixing the antibody having the desired degree of purity with optional physiologically acceptable carriers, excipients or stabilizers (*Remington's Pharmaceutical Sciences* 16th edition, Osol, A. Ed. (1980)), in the form of aqueous solutions, lyophilized or other dried formulations. Acceptable carriers, excipients, or stabilizers are nontoxic to recipients at the dosages and concentrations employed, and include buffers such as phosphate, citrate, histidine and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the immunoglobulin of the invention, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated immunoglobulins remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Uses

An antibody of the present invention may be used in, for example, in vitro, ex vivo and in vivo therapeutic methods. Antibodies of the invention can be used as an antagonist to partially or fully block the specific antigen activity in vitro, ex vivo and/or in vivo. Moreover, at least some of the antibodies of the invention can neutralize antigen activity from other species. Accordingly, the antibodies of the invention can be used to inhibit a specific antigen activity, e.g., in a cell culture containing the antigen, in human subjects or in other mammalian subjects having the antigen with which an antibody of the invention cross-reacts (e.g. chimpanzee, baboon, marmoset, cynomolgus and rhesus, pig or mouse). In one embodiment, the antibody of the invention can be used for inhibiting antigen activities by contacting the antibody with the antigen such that antigen activity is inhibited. Preferably, the antigen is a human protein molecule.

In one embodiment, an antibody of the invention can be used in a method for inhibiting an antigen in a subject suffering from a disorder in which the antigen activity is detrimental, comprising administering to the subject an antibody of the invention such that the antigen activity in the subject is inhibited. Preferably, the antigen is a human protein molecule and the subject is a human subject. Alternatively, the subject can be a mammal expressing the antigen with which an antibody of the invention binds. Still further the subject can be a mammal into which the antigen has been introduced (e.g., by administration of the antigen or by expression of an antigen transgene). An antibody of the invention can be administered to a human subject for therapeutic purposes. Moreover, an antibody of the invention can be administered to a non-human mammal expressing an antigen with which the immunoglobulin cross-reacts (e.g., a primate, pig or mouse) for veterinary purposes or as an animal model of human disease. Regarding the latter, such animal models may be useful for evaluating the therapeutic efficacy of antibodies of the invention (e.g., testing of dosages and time courses of administration). Blocking antibodies of the invention that are therapeutically useful include, for example but are not limited to, anti-HER2, anti-VEGF, anti-IgE, anti-CD11, anti-interferon and anti-tissue factor antibodies. The antibodies of the invention can be used to treat, inhibit, delay progression of, prevent/delay recurrence of, ameliorate, or prevent diseases, disorders or conditions associated with abnormal expression and/or activity of one or more antigen molecules, including but not limited to malignant and benign tumors; non-leukemias and lymphoid malignancies; neuronal, glial, astrocytal, hypothalamic and other glandular, macrophagal, epithelial, stromal and blastocoelic disorders; and inflammatory, angiogenic and immunologic disorders.

In one aspect, a blocking antibody of the invention is specific to a ligand antigen, and inhibits the antigen activity by blocking or interfering with the ligand-receptor interaction involving the ligand antigen, thereby inhibiting the corresponding signal pathway and other molecular or cellular events. The invention also features receptor-specific antibodies which do not necessarily prevent ligand binding but interfere with receptor activation, thereby inhibiting any responses that would normally be initiated by the ligand binding. The invention also encompasses antibodies that either preferably or exclusively bind to ligand-receptor complexes. An antibody of the invention can also act as an agonist of a particular antigen receptor, thereby potentiating, enhancing or activating either all or partial activities of the ligand-mediated receptor activation.

In certain embodiments, an immunoconjugate comprising an antibody conjugated with a cytotoxic agent is administered to the patient. In some embodiments, the immunoconjugate and/or antigen to which it is bound is/are internalized by the cell, resulting in increased therapeutic efficacy of the immunoconjugate in killing the target cell to which it binds. In one embodiment, the cytotoxic agent targets or interferes with nucleic acid in the target cell. Examples of such cytotoxic agents include any of the chemotherapeutic agents noted herein (such as a maytansinoid or a calicheamicin), a radioactive isotope, or a ribonuclease or a DNA endonuclease.

Antibodies of the invention can be used either alone or in combination with other compositions in a therapy. For instance, an antibody of the invention may be co-administered with another antibody, chemotherapeutic agent(s) (including cocktails of chemotherapeutic agents), other cytotoxic agent(s), anti-angiogenic agent(s), cytokines, and/or growth inhibitory agent(s). Where an antibody of the invention inhibits tumor growth, it may be particularly desirable to combine it with one or more other therapeutic agent(s) which also inhibits tumor growth. For instance, an antibody of the invention may be combined with an anti-VEGF antibody (e.g., AVASTIN) and/or anti-ErbB antibodies (e.g. HERCEPTIN® anti-HER2 antibody) in a treatment scheme, e.g. in treating any of the diseases described herein, including colorectal cancer, metastatic breast cancer and kidney cancer. Alternatively, or additionally, the patient may receive combined radiation therapy (e.g. external beam irradiation or therapy with a radioactive labeled agent, such as an antibody). Such combined therapies noted above include combined administration (where the two or more agents are included in the same or separate formulations), and separate administration, in which case, administration of the antibody of the invention can occur prior to, and/or following, administration of the adjunct therapy or therapies.

The antibody of the invention (and adjunct therapeutic agent) is/are administered by any suitable means, including parenteral, subcutaneous, intraperitoneal, intrapulmonary, and intranasal, and, if desired for local treatment, intralesional administration. Parenteral infusions include intramuscular, intravenous, intraarterial, intraperitoneal, or subcutaneous administration. In addition, the antibody is suitably administered by pulse infusion, particularly with declining doses of the antibody. Dosing can be by any suitable route, e.g. by injections, such as intravenous or subcutaneous injections, depending in part on whether the administration is brief or chronic.

The antibody composition of the invention will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibodies of the invention present in the formulation, the type of disorder or treatment, and other factors discussed above. These are generally used in the same dosages and with administration routes as used hereinbefore or about from 1 to 99% of the heretofore employed dosages.

For the prevention or treatment of disease, the appropriate dosage of an antibody of the invention (when used alone or in combination with other agents such as chemotherapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g. 0.1 mg/kg-10 mg/kg) of antibody is an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment is sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, e.g. about six doses of the antibody). An initial higher loading dose, followed by one or more lower doses may be administered. An exemplary dosing regimen comprises administering an initial loading dose of about 4 mg/kg, followed by a weekly maintenance dose of about 2 mg/kg of the antibody. However, other dosage regimens may be useful. The progress of this therapy is easily monitored by conventional techniques and assays.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, etc. The containers may be formed from a variety of materials such as glass or plastic. The container holds a composition which is by itself or when combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice, such as cancer. Moreover, the article of manufacture may comprise (a) a first container with a composition contained therein, wherein the composition comprises an antibody of the invention; and (b) a second container with a composition contained therein, wherein the composition comprises a further cytotoxic agent. The article of manufacture in this embodiment of the invention may further comprise a package insert indicating that the first and second antibody compositions can be used to treat a particular condition, e.g. cancer. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The following are examples of the methods and compositions of the invention. It is understood that various other embodiments may be practiced, given the general description provided above.

EXAMPLES

Materials and Methods

Residue numbers are according to Kabat (Kabat et al., *Sequences of proteins of immunological interest*, 5th Ed., Public Health Service, National Institutes of Health, Bethesda, Md. (1991)). Single letter amino acid abbreviations are used. DNA degeneracies are represented using the IUB code (N=A/C/G/T, D=A/G/T, V=A/C/G, B=C/G/T, H=A/C/T, K=G/T, M=A/C, R=A/G, S=G/C, W=A/T, Y=C/T).

Direct hypervariable region grafts onto the acceptor human consensus framework—The phagemid used for this work is a monovalent Fab-g3 display vector (pV0350-2B) having 2 open reading frames under control of the phoA promoter, essentially as described in Lee et al., *J. Mol. Biol.* (2004), 340(5):1073-93. The first open reading frame consists of the stII signal sequence fused to the VL and CL domains of the acceptor light chain and the second consists of the stII signal sequence fused to the VH and CH1 domains of the acceptor heavy chain followed by a truncated minor phage coat protein P3. See Lee et al., supra.

Figure 1A:
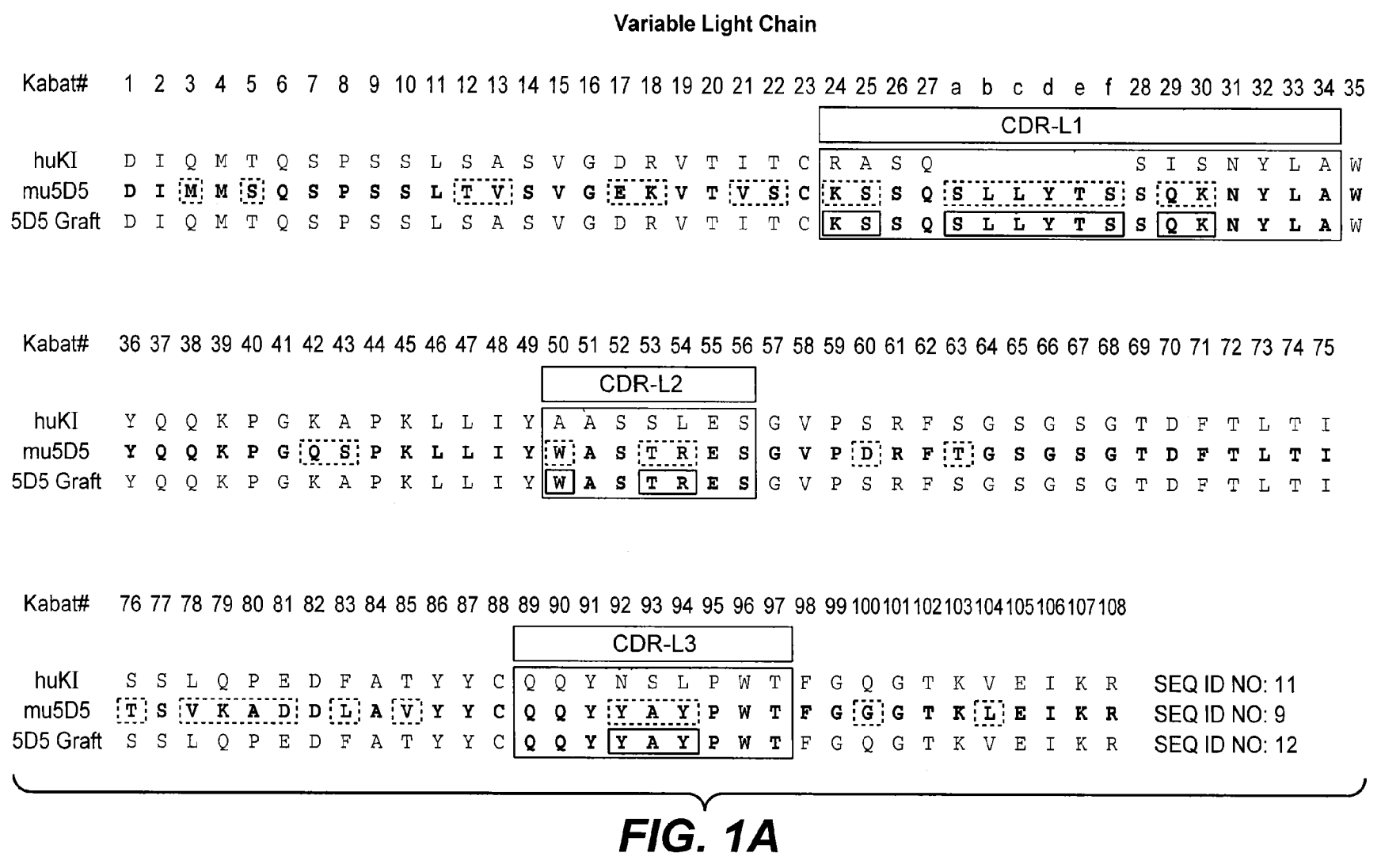

The VL and VH domains from murine 5D5 (see hybridoma 5D5.11.6, ATCC Deposit No. HB-11895, deposit date May 23, 1995) were aligned with the human consensus kappa I (huKI) and human subgroup III consensus VH domains. To make the HVR graft, the acceptor VH framework, which differs from the human subgroup III consensus VH domain at 3 positions: R71A, N73T, and L78A (Carter et al., *Proc. Natl. Acad. Sci. USA* 89:4285 (1992)) was used. Hypervariable regions from the murine 5D5 (mu5D5) antibody were engineered into the acceptor human consensus framework to generate a direct HVR-graft of 5D5 (5D5 graft). In the VL domain the following regions were grafted to the human consensus acceptor: positions 24-34 (L1), 50-56 (L2) and 89-97 (L3). In the VH domain, positions 26-35 (H1), 49-65 (H2) and 95-102 (H3) were grafted (FIG. 1).

The direct-graft variants were generated by Kunkel mutagenesis using a separate oligonucleotide for each hypervariable region. Correct clones were assessed by DNA sequencing.

Soft randomization of the hypervariable regions—Sequence diversity was introduced into each hypervariable region using a soft randomization strategy that maintains a bias towards the murine hypervariable region sequence. This was accomplished using a poisoned oligonucleotide synthesis strategy as described by Gallop et al., *J. Med. Chem.* 37:1233-1251 (1994). For a given position within a hypervariable region to be mutated, the codon encoding the wild-type amino acid is poisoned with a 70-10-10-10 mixture of nucleotides resulting in an average 50 percent mutation rate at each position.

Soft randomized oligonucleotides were patterned after the murine hypervariable region sequences and encompassed the same regions defined by the direct hypervariable region grafts. The amino acid position at the beginning of H2 (position 49) in the VH domain, was limited in sequence diversity to A, G, S or T by using the codon RGC.

Generation of phage libraries—Randomized oligonucleotide pools designed for each hypervariable region were phosphorylated separately in six 20 µl reactions containing 660 ng of oligonucleotide, 50 mM Tris pH 7.5, 10 mM $MgCl_2$, 1 mM ATP, 20 mM DTT, and 5 U polynucleotide kinase for 1 h at 37° C. The six phosphorylated oligonucleotide pools were then combined with 20 µg of Kunkel template in 50 mM Tris pH 7.5, 10 mM $MgCl_2$ in a final volume of 500 µl resulting in a oligonucleotide to template ratio of 3. The mixture was annealed at 90° C. for 4 min, 50° C. for 5 min and then cooled on ice. Excess, unannealed oligonucleotide was removed with a QIAQUICK PCR purification kit (Qiagen kit 28106) using a modified protocol to prevent excessive denaturation of the annealed DNA. To the 500 µl of annealed mixture, 150 µl of PB was added, and the mixture was split between 2 silica columns. Following a wash of each column with 750 µl of PE and an extra spin to dry the columns, each column was eluted with 110 µl of 10 mM Tris, 1 mM EDTA, pH 8. The annealed and cleaned-up template (220 µl) was then filled in by adding 1 µl 100 mM ATP, 10 µl 25 mM dNTPs (25 mM each of dATP, dCTP, dGTP and dTTP), 15 µl 100 mM DTT, 25 µl 10×TM buffer (0.5 M Tris pH 7.5, 0.1 M $MgCl_2$), 2400 U T4 ligase, and 30 U T7 polymerase for 3 h at room temperature.

The filled in product was analyzed on Tris-Acetate-EDTA/agarose gels (Sidhu et al., *Methods in Enzymology* 328:333-363 (2000)). Three bands were usually visible: the bottom band is a correctly filled and ligated product, the middle band is a filled but unligated product, and the top band is a strand displaced product. The top band is produced by an intrinsic side activity of T7 polymerase and is difficult to avoid (Lechner et al., *J. Biol. Chem.* 258:11174-11184 (1983)); however, this band transforms 30-fold less efficiently than the bottom band and usually contributes little to the library. The middle band is due to the absence of a 5' phosphate for the final ligation reaction; this band transforms efficiently and gives mainly wild type sequence.

The filled in product was then cleaned-up and electroporated into SS320 cells and propagated in the presence of M13/KO7 helper phage as described by Sidhu et al., *Methods in Enzymology* 328:333-363 (2000). Library sizes ranged from $1-2\times10^9$ independent clones. Random clones from the initial libraries were sequenced to assess library quality.

Phage Selection—The human HGF receptor was generated and used as an Fc fusion (HGFR-Fc) (Mark et al., *J. Biol. Chem.* (1992), 267:26166-26171). HGFR-Fc was coated on MaxiSorp microtiter plates (Nunc) at 5 µg/ml in PBS. For the first round of selection 8 wells of target were used; a single well of target was used for successive rounds of selection. Wells were blocked for 1 h using Casein Blocker (Pierce). Phage were harvested from the culture supernatant and suspended in PBS containing 1% BSA and 0.05% TWEEN 20 (PBSBT). After binding to the wells for 2 h, unbound phage were removed by extensive washing with PBS containing 0.05% TWEEN 20 (PBST). Bound phage were eluted by incubating the wells with 50 mM HCl, 0.5 M KCl for 30 min. Phage were amplified using Top10 cells and M13/KO7 helper phage and grown overnight at 37° C. in 2YT, 50 µg/ml carbenecillin. The titers of phage eluted from a target coated well were compared to titers of phage recovered from a non-target coated well to assess enrichment.

For affinity maturation, phage libraries were sorted using a solution sorting method. HFGR-Fc was biotinylated by mixing 500 µl of 3.6 mg/ml HGFR-Fc in PBS, and 10 µl of 1 M Potassium phosphate, pH 8 with 20 µl 4 mM Sulfo-NHS-LC-biotin (Pierce). Biotinylated HGFR-Fc (b-HGFR-Fc) was purified using a NAPS column (Amersham Biosciences) in PBS. Microtiter wells were coated with 10 µg/ml neutravidin in PBS overnight at 4° C. and then blocked for 1 h using Casein Blocker (Pierce). In the first round of panning, 200 µl phage suspended in PBS containing 0.05% Tween 20 (PBST) and 1% BSA were mixed with 10 nM b-HGFR-Fc for 1 hr. Phage bound to b-HGFR-Fc were captured on neutravidin coated wells for 10 min and unbound phage were washed away with PBST. Phage were eluted using 20 mM HCl, 500 mM KCl for 45 m, neutralized, and propagated in XL1 blue cells (Stratagene) in the presence of KO7 helper phage (New England Biolabs). Subsequent rounds of sorting were performed similarly with the following exceptions: in round 2 the final b-HGFR-Fc concentration was 5.6 nM, in round 3 the final b-HGFR-Fc concentration was 0.1 nM, in round 4 the final b-HGFR-Fc concentration was 0.5 nM and 780 nM unbiotinylated HGFR-Fc was added to the mixture for 1 h prior to capture on neutravidin.

Phage ELISA—MaxiSorp microtiter plates were coated with human HGFR-Fc at 5 µg/ml in PBS over night and then blocked with Casein Blocker. Phage from culture supernatants were incubated with serially diluted HGFR-Fc in PBST containing 1% BSA in a tissue culture microtiter plate for 1 h after which 80 µl of the mixture was transferred to the target coated wells for 15 min to capture unbound phage. The plate was washed with PBST and HRP conjugated anti-M13 (Amersham Pharmacia Biotech) was added (1:5000 in PBST containing 1% BSA) for 40 min. The plate was washed with PBST and developed by adding Tetramethylbenzidine substrate (Kirkegaard and Perry Laboratories, Gaithersburg, Md.). The absorbance at 405 nm was plotted as a function of target concentration in solution to determine an $IC_{50}$. This was used as an affinity estimate for the Fab clone displayed on the surface of the phage.

Fab Production and Affinity Determination—To express Fab protein for affinity measurements, a stop codon was introduced between the heavy chain and g3 in the phage display vector. Clones were transformed into E. coli 34B8 cells and grown in AP5 media at 30 C (Presta et al. Cancer Res. 57: 4593-4599 (1997)). Cells were harvested by centrifugation, suspended in 10 mM Tris, 1 mM EDTA pH 8 and broken open using a microfluidizer. Fab was purified with Protein G affinity chromatography.

Affinity determinations were performed by surface plasmon resonance using a BIAcore™-2000. HGFR-Fc was immobilized (~1000 response units (RU)) on a CM5 chip and varied concentrations of Fab (4 to 500 nM) in PBST were injected. After each injection the chip was regenerated using 100 mM HCl. Binding response was corrected by subtracting the RU from a blank flow cell. A 1:1 Languir model of simultaneous fitting of $k_{on}$ and $k_{off}$ was used for kinetics analysis.

Electro-Chemiluminescent Assay for OA5D5 Blocking of HGF/cMet Binding

Purified cMet-Ig protein produced at Genentech (South San Francisco, Calif.) was biotinylated by incubating with 20-fold molar excess NHS-X-Biotin in 0.1 M NaHCO3, pH 8.5 using biotin-X-NHS (Research Organics, Cleveland, Ohio). Purified human 2-chain HGF produced at Genentech was labeled with BV-TAG (cat #110034) via NHS-ester chemistry according to manufacturer's directions (BioVeris International, Gaithersburg, Md.). cMet-Ig-biotin (500 ng/mL), HGF-Ruthenium Tag (250 ng/mL), and titrations of OA5D5 antibody ranging from 3333-0.21 nM of antibody were incubated together in a volume of 100 ul of assay diluent: PBS+0.5% BSA/0.5% Tween 20/0.033% Proclin (Supelco Inc. Bellefonte Pa.). The mixtures were incubated in sealed polypropylene round bottom 96 well plates (Corning) for 2-4 hours at room temperature with shaking. Streptavidin magnetic beads (Dynabeads, BioVeris) were added. Following a final 45 min incubation with vigorous shaking, the plates were read using a BioVeris M-Series instrument (BioVeris International, Gaithersburg, Md.).

KIRA (HGF-Dependent-Met Phosphorylation)

A549 cells (ATCC, Manassas, Va.) were maintained in growth medium (Ham's F12/DMEM 50:50 [Gibco, Grand Island, N.Y.] containing 10% fetal bovine serum (FBS, Sigma, St. Louis, Mo.). To prepare cells for the assay, cells from confluent cultures were detached using Accutase (ICN, Aurora, Ohio) and seeded into 96 well plates at a density of 50,000 cells per well. After an overnight incubation at 37° C., growth media was removed and cells were serum starved for 30-60 min in medium containing 0.1% FBS. To determine the ability of OA-5D5 to inhibit cMet phosphorylation, the molecule was serially diluted from 200 to 0.19 nM in medium+ 0.1% FBS and added to the assay plates. After a 15 min incubation at 37° C., HGF (50 ng/ml) was added. The plates were then incubated for an additional 10 minutes at 37° C., the media was removed and a cell lysis buffer was added (Cell Signaling Technologies, Cat #9803, Beverly, Mass.; supplemented with a protease inhibitor cocktail purchased from Calbiochem, Cat #539131, San Diego, Calif.). The lysates were analyzed for phosphorylated c-Met via an electrochemiluminescence assay using an BioVeris M-Series instrument (BioVeris International, Gaithersburg, Md.). An anti-phosphotyrosine mAb (clone 4G10, Upstate, Lake Placid, MY) was labeled with BV-TAG via NHS-ester chemistry according to manufacturer's directions (BioVeris). Antibodies against the c-Met extracellular domain were biotinylated using biotin-X-NHS (Research Organics, Cleveland, Ohio). The BV-TAG-labeled 4G10 and biotinylated anti-c-Met mAb were diluted in assay buffer (PBS/0.5% Tween-20/0.5% BSA) and added as a cocktail to the cell lysates. After a 1.5-2 hr incubation at room temperature with vigorous shaking, streptavidin magnetic beads (Dynabeads, BioVeris) were added. Following a final 45 min incubation, the plates were read on the BioVeris instrument.

Cell Culture and Proliferation Assay

BaF3 is a murine IL-3 dependent lymphoid cell that normally does not express cMet and does not respond to HGF. However, in BaF3-hMet derived by transfection with a normal, full-length cDNA for human c-Met (Schwall et al., J. Cell Biol. (1996), 133:709-718), HGF stimulates proliferation and survival in the absence of IL-3. BaF3-hMet and BaF3-neo cells were routinely passaged in RPMI 1640, 5% fetal bovine serum, 4 μl/L β-mercapthoethanol, 100 U/ml penicillin, 100 μg/ml streptomycin sulfate, 2 mM L-glutamine, and 5% WEHI-conditioned medium as a source of IL-3. To measure HGF-dependent proliferation the number of cells after 3 days of treatment was quantitated by adding 25 μl Alarma Blue (Trek Diagnostic Systems; Cleveland, Ohio) and measuring fluorescence intensity 6 hours later. Control experiments were proliferation of these cells in the absence of HGF. H358-PSF2 and HGF-PSF8 cells were passaged in RPMI 1640, 10% fetal bovine serum, 100 U/ml penicillin, 100 μg/ml streptomycin sulfate, 2 mM L-glutamine. The assay medium was RPMI 1640 plus 0.1%, 0.5% BSA, or 10% FBS respectively. The assay was performed as described above.

Immunoprecipitation and Western Blot

H358 cells are a cell line derived from human non-small cell lung carcinoma (NSCLC). H358-PSF2, H358-PSF8 cells are human HGF stable transfected H358 cells (Tsao et al., Neoplasia, Vol. 2, No. 3, 2000), and were cultured in RPMI 1640, 10% fetal bovine serum, 100 U/ml penicillin, 100 μg/ml streptomycin sulfate, 2 mM L-glutamine. cMet tyrosine phosphorylation detection was performed essentially as described previously (Zioncheck, J Bio Chem, 270 (28):16871-8, 1995). In brief, cells were plated in 60-mm plates overnight, and medium was changed to RPMI 1640 containing 0.5% BSA, before adding the combinations of with or without 1 nM HGF or competitor OA5D5.v2 antibody. After 10 min at 37° C., medium was removed and cells were lysed using lysis buffer (150 mM NaCl, 1.5 mM MgCl2, 1% Triton X-100, 1× protease inhibitor cocktail, 1× phosphatase inhibitor cocktail (Sigma, St. Louis, Mo.)). After spinning, the supernatant of the lysate was incubated with anti-cMet IgG polyclonal antibody (c-28; Santa Cruz Biotechnology, Santa Cruz, Calif.) bound to protein G-Sepharose for 1 hour at 4° C. The immune complexes were washed and boiled in 1× sample buffer, before separation by SDS-PAGE and electroblotting to nitrocellulose. Phosphotyrosine-containing proteins were visualized using an anti-phosphotyrosine antibody (4G10; Upstate Biotechnology, Waltham, Mass.) followed by HRP-conjugated goat anti-mouse Fab (1:10,000; Jackson Labs, West Grove, Pa.), and in the case of total cMet using c-28 antibody (1:400; Santa Cruz Biotechnology, Santa Cruz, Calif.) followed by goat anti-rabbit Fc-HRP (1:10,000; Jackson Labs, West Grove, Pa.) with chemiluminescence detection.

Tumor Xenograft Study

Athymic female mice were inoculated subcutaneously with 5 million KP4 pancreatic carcinoma cells. When tumors reached 150-200 mm³, mice were assigned to 2 groups of 10. Group 1 was injected IP with vehicle twice per week. Group 2 was injected IP with OA5D5.v2, 30 mg/kg, twice per week. Tumor size was measured twice per week. Mice were sacrificed when tumor volume exceeded two-times the starting tumor volume, or if the tumor ulcerated.

Results and Discussion

Humanization of 5D5—The human acceptor framework used for the humanization of 5D5 comprises the consensus human kappa I VL domain and a variant of the human subgroup III consensus VH domain. The variant VH domain has 3 changes from the human consensus: R71A, N73T and L78A. The VL and VH domains of murine 5D5 were aligned with the human kappa I and subgroup III domains; each HVR was identified and then grafted into the human acceptor framework to generate a 5D5 graft that could be displayed as an Fab on phage. When phage displaying the 5D5 graft were tested for binding to immobilized HGFR-Fc, no binding was observed.

A library was generated in which each of the HVR regions of the 5D5 graft was soft randomized. This library was panned against immobilized HGFR-Fc for 4 rounds of selection. Clones were picked for DNA sequence analysis and revealed a single clone had been selected. This clone had a single change in the VH domain at position 94 (R94S) just outside the intended region of HVR-H3 targeted for mutagenesis. Analysis of this clone by phage ELISA indicated it had similar affinity to that of the monovalent affinity of murine 5D5. When expressed as an Fab and tested by Biacore, the Kd was determined to be 9.8 nM compared to 8.3 nM for the monovalent affinity of murine 5D5. Thus this unexpected substitution restores full binding affinity to the 5D5 graft, and the 5D5 graft plus R94S (hu5D5.v1) represents a fully humanized antibody. Interestingly, a homologous amino acid, threonine, is found at this position in the murine antibody. MacCallum et al. (MacCallum et al. *J. Mol. Biol.* 262: 732-745 (1996)) have analyzed antibody and antigen complex crystal structures and found positions 93 and 94 of the heavy chain are part of the contact region thus it seems reasonable to include these positions in the definition of hypervariable region of H3 (HVR-H3) when humanizing antibodies.

Affinity maturation of hu5D5.v1—To improve the affinity of hu5D5.v1, six phage display libraries were generated in the background of hu5D5.v1, each targeting a single HVR for soft randomization. To avoid re-selecting hu5D5.v1 from a potential high background of wild-type template, stop codons were introduced into the HVR to be mutated prior to generating each library. A solution sorting method was used to enhance the efficiency of the affinity-based phage selection process. By manipulating the biotinylated target concentration, reducing the phage capture time to lower backgrounds and the addition of unbiotinylated target to eliminate clones with faster off rates, high affinity clones can be proficiently selected. Lee et al., supra. From the first round of selection, enrichment (target dependent phage capture) was observed suggesting a large number of clones were present in each library with reasonably high affinity for HGFR-Fc. Selection stringency (see Methods above) was increased in subsequent rounds and at round 3 all 6 libraries were combined to generate a seventh library pool. After 4 rounds of selection, clones from each of the 7 library pools were analyzed. All clones in the libraries targeting HVR-L1 and HVR-L3 were identical to hu5D5.v1; however, new sequences were observed in libraries targeting HVR-L2, HVR-H1, HVR-H2 and HVR-H3 (FIG. 2). The library pool consisting of the combination of all 6 libraries was dominated by sequences from the HVR-H3 library suggesting that these sequences provided the largest improvement in affinity for HGFR-Fc (FIG. 3). Selected clones were screened by phage ELISA and then expressed as Fab protein and their affinity determined using Biacore. Several clones from the combined library with changes in HVR-H3 had improved affinities compared to hu5D5.v1 or the murine 5D5 monovalent affinity (FIG. 4). These clones had either S/T at position 94, R/S at position 96 and T/S at position 100 and P/S/A at position 100a. The best clone, clone 78 (hu5D5.v2) had 3 changes from hu5D5.v1 (94T, 96R and 100T) and a 13-fold affinity improvement.

Thus starting from the graft of the 6 murine 5D5 HVRs into the human acceptor scaffold, the expansion of HVR-H3 to include position 94 (Threonine) and the addition of 2 changes in HVR-H3 leads to a fully human 5D5 antibody with 13-fold improved binding affinity for HGFR. Furthermore, selected humanized antibodies described herein have been determined to have at least comparable biological activity as the parent 5D5 antibody, for example in receptor phosphorylation assays, etc. (data not shown).

Characterization of an antibody of the invention—"One-armed" (also referred to as "one-arm" and "OA") anti-Met antibodies were characterized. Two antibodies of the invention were tested. Specifically, the "OA-5D5.v2" antibody comprised a single Fab arm comprising variable domain sequences as depicted in FIG. 13, wherein the Fab arm was fused to an Fc region, and wherein the Fc region was a complex between one Fc polypeptide comprising the Fc sequence depicted in FIG. 13 and one Fc polypeptide comprising the Fc sequence depicted in FIG. 14. The antibodies were characterized as follows:

(1) In an assay to test ability of OA-5D5.v2 to block binding of HGF to its receptor, OA-5D5.v2 was able to block HGF binding to its receptor at least as well as two comparator antibodies—namely a chimeric one-armed antibody (which comprised a Fab arm from the murine parent 5D5 antibody (variable domains depicted in to FIG. 7) fused to a human Fc region), and another antibody of the invention (OA-5D5.v1). When tested across an antibody concentration range of about 3333 to 0.21 nM, under conditions as described in the Materials and Methods section above, OA-5D5.v2 was found to have an IC50 value that was less than about half that of a comparator antibody such as the chimeric one-armed antibody and OA-5D5.v1. Notably, OA-5D5.v1 also blocked with better IC50 than the reference chimeric antibody. See FIG. 8.

(2) In an assay to test ability of OA-5D5.v2 to inhibit HGF receptor activation, OA-5D5.v2 was able to inhibit kinase receptor activation at least as well as the two comparator antibodies as described in (1) above. When tested across an antibody concentration range of about 200 to 0.19 nM, under conditions as described in the Materials and Methods section above, OA-5D5.v2 was found to have an IC50 with a value that was less than about half that of a comparator antibody such as the chimeric one-armed antibody and OA-5D5.v1. See FIG. 9.

(3) OA-5D5.v2 was also tested for cross-species binding among human, primate (cynomolgus monkey), canine and murine (mouse). OA-5D5.v2 was found to bind specifically to human and primate (cynomolgus monkey) HGF receptor, but not canine or murine (mouse). (data not shown.)

(4) OA-5D5.v2 was tested for its ability to inhibit cell proliferation in the presence of HGF. As shown in FIG. 10, OA-5D5.v2 inhibited cell proliferation at least as well as its chimeric antibody counterpart and OA-5D5.v1 (as described in (1) above). When tested across an antibody concentration range of about 0.01 to 100 nM, under conditions as described in the Materials and Methods section above, OA-5D5.v2 was found to have an IC50 value that was less than about half that of a comparator antibody such as the chimeric one-armed antibody and OA-5D5.v1. See FIG. 10. Specific binding of OA-5D5.v2 to the Met-transfected cells was confirmed by FACs analysis. (data not shown)

(5) OA-5D5.v2 was tested for its ability to inhibit receptor tyrosine phosphorylation in the presence of HGF. As shown in FIGS. 11A and B, OA-5D5.v2 inhibited receptor tyrosine phosphorylation when tested at antibody concentrations from about 10 to 1000 nM. See FIGS. 11A and B.

(6) OA-5D5.v2 was tested for in vivo efficacy using a tumor xenograft model based on a pancreatic tumor cell line (KP4). Results from this efficacy study showed that the OA-5D5.v2 antibody was capable of inhibiting and causing regression of tumors in vivo. As shown in FIG. 12, there was complete loss of tumor in most of the animals treated with the antibody.

PARTIAL REFERENCE LIST

Angeloni, D., Danilkovitch-Miagkova, A., Miagkov, A., Leonard, E. J., and Lerman, M. I. (2003). The soluble sema domain of the Ron receptor inhibits MSP-induced receptor activation. J Biol Chem.

Antipenko, A., Himanen, J. P., van Leyen, K., Nardi-Dei, V., Lesniak, J., Barton, W. A., Rajashankar, K. R., Lu, M., Hoemme, C., Puschel, A. W., and Nikolov, D. B. (2003). Structure of the semaphorin-3A receptor binding module. Neuron 39, 589-598.

Bardelli, A., Longati, P., Gramaglia, D., Stella, M. C., and Comoglio, P. M. (1997). Gab1 coupling to the HGF/Met receptor multifunctional docking site requires binding of Grb2 and correlates with the transforming potential. Oncogene 15, 3103-3111.

Bertotti, A., and Comoglio, P. M. (2003). Tyrosine kinase signal specificity: lessons from the HGF receptor. Trends Biochem Sci 28, 527-533.

Bladt, F., Riethmacher, D., Isenmann, S., Aguzzi, A., and Birchmeier, C. (1995). Essential role for the c-met receptor in the migration of myogenic precursor cells into the limb bud. Nature 376, 768-771.

Blechman, J. M., Lev, S., Barg, J., Eisenstein, M., Vaks, B., Vogel, Z., Givol, D., and Yarden, Y. (1995). The fourth immunoglobulin domain of the stem cell factor receptor couples ligand binding to signal transduction. Cell 80, 103-113.

Boix, L., Rosa, J. L., Ventura, F., Castells, A., Bruix, J., Rodes, J., and Bartrons, R. (1994). c-met mRNA overexpression in human hepatocellular carcinoma. Hepatology 19, 88-91.

Bottaro, D. P., Rubin, J. S., Faletto, D. L., Chan, A. M., Kmiecik, T. E., Vande Woude, G. F., and Aaronson, S. A. (1991). Identification of the hepatocyte growth factor receptor as the c-met proto-oncogene product. Science 251, 802-804.

Bussolino, F., Di Renzo, M. F., Ziche, M., Bocchietto, E., Olivero, M., Naldini, L., Gaudino, G., Tamagnone, L., Coffer, A., and Comoglio, P. M. (1992). Hepatocyte growth factor is a potent angiogenic factor which stimulates endothelial cell motility and growth. J Cell Biol 119, 629-641.

Coltella, N., Manara, M. C., Cerisano, V., Trusolino, L., Di Renzo, M. F., Scotlandi, K., and Ferracini, R. (2003). Role of the MET/HGF receptor in proliferation and invasive behavior of osteosarcoma. Faseb J 17, 1162-1164.

Cooper, C. S., Park, M., Blair, D. G., Tainsky, M. A., Huebner, K., Croce, C. M., and Vande Woude, G. F. (1984). Molecular cloning of a new transforming gene from a chemically transformed human cell line. Nature 311, 29-33.

Di Renzo, M. F., Olivero, M., Giacomini, A., Porte, H., Chastre, E., Mirossay, L., Nordlinger, B., Bretti, S., Bottardi, S., Giordano, S., and et al. (1995). Overexpression and amplification of the met/HGF receptor gene during the progression of colorectal cancer. Clin Cancer Res 1, 147-154.

Ferguson, K. M., Berger, M. B., Mendrola, J. M., Cho, H. S., Leahy, D. J., and Lemmon, M. A. (2003). EGF activates its receptor by removing interactions that autoinhibit ectodomain dimerization. Mol Cell 11, 507-517.

Furge, K. A., Zhang, Y. W., and Vande Woude, G. F. (2000). Met receptor tyrosine kinase: enhanced signaling through adapter proteins. Oncogene 19, 5582-5589.

Garrett, T. P., McKern, N. M., Lou, M., Elleman, T. C., Adams, T. E., Lovrecz, G. O., Zhu, H. J., Walker, F., Frenkel, M. J., Hoyne, P. A., et al. (2002). Crystal structure of a truncated epidermal growth factor receptor extracellular domain bound to transforming growth factor alpha. Cell 110, 763-773.

Gherardi, E., Youles, M. E., Miguel, R. N., Blundell, T. L., Iamele, L., Gough, J., Bandyopadhyay, A., Hartmann, G., and Butler, P. J. (2003). Functional map and domain structure of MET, the product of the c-met protooncogene and receptor for hepatocyte growth factor/scatter factor. Proc Natl Acad Sci USA.

Giancotti, F. G., and Ruoslahti, E. (1999). Integrin signaling. Science 285, 1028-1032.

Giordano, S., Corso, S., Conrotto, P., Artigiani, S., Gilestro, G., Barberis, D., Tamagnone, L., and Comoglio, P. M. (2002). The semaphorin 4D receptor controls invasive growth by coupling with Met. Nat Cell Biol 4, 720-724.

Giordano, S., Di Renzo, M. F., Narsimhan, R. P., Cooper, C. S., Rosa, C., and Comoglio, P. M. (1989). Biosynthesis of the protein encoded by the c-met proto-oncogene. Oncogene 4, 1383-1388.

Giordano, S., Maffe, A., Williams, T. A., Artigiani, S., Gual, P., Bardelli, A., Basilico, C., Michieli, P., and Comoglio, P. M. (2000). Different point mutations in the met oncogene elicit distinct biological properties. Faseb J 14, 399-406.

Hamanoue, M., Takemoto, N., Matsumoto, K., Nakamura, T., Nakajima, K., and Kohsaka, S. (1996). Neurotrophic effect of hepatocyte growth factor on central nervous system neurons in vitro. J Neurosci Res 43, 554-564.

Hartmann, G., Weidner, K. M., Schwarz, H., and Birchmeier, W. (1994). The motility signal of scatter factor/hepatocyte growth factor mediated through the receptor tyrosine kinase met requires intracellular action of Ras. J Biol Chem 269, 21936-21939.

Jeffers, M., Rong, S., and Vande Woude, G. F. (1996). Enhanced tumorigenicity and invasion-metastasis by hepatocyte growth factor/scatter factor-met signalling in human cells concomitant with induction of the urokinase proteolysis network. Mol Cell Biol 16, 1115-1125.

Jeffers, M., Schmidt, L., Nakaigawa, N., Webb, C. P., Weirich, G., Kishida, T., Zbar, B., and Vande Woude, G. F. (1997). Activating mutations for the met tyrosine kinase receptor in human cancer. Proc Natl Acad Sci USA 94, 11445-11450.

Jin, L., Fuchs, A., Schnitt, S. J., Yao, Y., Joseph, A., Lamszus, K., Park, M., Goldberg, I. D., and Rosen, E. M. (1997). Expression of scatter factor and c-met receptor in benign and malignant breast tissue. Cancer 79, 749-760.

Kuniyasu, H., Yasui, W., Yokozaki, H., Kitadai, Y., and Tahara, E. (1993). Aberrant expression of c-met mRNA in human gastric carcinomas. Int J Cancer 55, 72-75.

Lev, S., Yarden, Y., and Givol, D. (1992). A recombinant ectodomain of the receptor for the stem cell factor (SCF) retains ligand-induced receptor dimerization and antagonizes SCF-stimulated cellular responses. J Biol Chem 267, 10866-10873.

Liu, C., Park, M., and Tsao, M. S. (1992). Overexpression of c-met proto-oncogene but not epidermal growth factor receptor or c-erbB-2 in primary human colorectal carcinomas. Oncogene 7, 181-185.

Lokker, N. A., Mark, M. R., Luis, E. A., Bennett, G. L., Robbins, K. A., Baker, J. B., and Godowski, P. J. (1992). Structure-function analysis of hepatocyte growth factor: identification of variants that lack mitogenic activity yet retain high affinity receptor binding. Embo J 11, 2503-2510.

Lorenzato, A., Olivero, M., Patane, S., Rosso, E., Oliaro, A., Comoglio, P. M., and Di Renzo, M. F. (2002). Novel somatic mutations of the MET oncogene in human carcinoma metastases activating cell motility and invasion. Cancer Res 62, 7025-7030.

Love, C. A., Harlos, K., Mavaddat, N., Davis, S. J., Stuart, D. I., Jones, E. Y., and Esnouf, R. M. (2003). The ligand-binding face of the semaphorins revealed by the high-resolution crystal structure of SEMA4D. Nat Struct Biol 10, 843-848.

Maina, F., Casagranda, F., Audero, E., Simeone, A., Comoglio, P. M., Klein, R., and Ponzetto, C. (1996). Uncoupling of Grb2 from the Met receptor in vivo reveals complex roles in muscle development. Cell 87, 531-542.

Matsumoto, K., and Nakamura, T. (1993). Roles of HGF as a pleiotropic factor in organ regeneration. Exs 65, 225-249.

Maulik, G., Shrikhande, A., Kijima, T., Ma, P. C., Morrison, P. T., and Salgia, R. (2002). Role of the hepatocyte growth factor receptor, c-Met, in oncogenesis and potential for therapeutic inhibition. Cytokine Growth Factor Rev 13, 41-59.

Meiners, S., Brinkmann, V., Naundorf, H., and Birchmeier, W. (1998). Role of morphogenetic factors in metastasis of mammary carcinoma cells. Oncogene 16, 9-20.

Morello, S., Olivero, M., Aimetti, M., Bernardi, M., Berrone, S., Di Renzo, M. F., and Giordano, S. (2001). MET receptor is overexpressed but not mutated in oral squamous cell carcinomas. J Cell Physiol 189, 285-290.

Naka, D., Ishii, T., Yoshiyama, Y., Miyazawa, K., Hara, H., Hishida, T., and Kidamura, N. (1992). Activation of hepatocyte growth factor by proteolytic conversion of a single chain form to a heterodimer. J Biol Chem 267, 20114-20119.

Naldini, L., Weidner, K. M., Vigna, E., Gaudino, G., Bardelli, A., Ponzetto, C., Narsimhan, R. P., Hartmann, G., Zarnegar, R., Michalopoulos, G. K., and et al. (1991). Scatter factor and hepatocyte growth factor are indistinguishable ligands for the MET receptor. Embo J 10, 2867-2878.

Natali, P. G., Prat, M., Nicotra, M. R., Bigotti, A., Olivero, M., Comoglio, P. M., and Di Renzo, M. F. (1996). Overexpression of the met/HGF receptor in renal cell carcinomas. Int J Cancer 69, 212-217.

Nguyen, L., Holgado-Madruga, M., Maroun, C., Fixman, E. D., Kamikura, D., Fournier, T., Charest, A., Tremblay, M. L., Wong, A. J., and Park, M. (1997). Association of the multisubstrate docking protein Gab1 with the hepatocyte growth factor receptor requires a functional Grb2 binding site involving tyrosine 1356. J Biol Chem 272, 20811-20819.

Nusrat, A., Parkos, C. A., Bacarra, A. E., Godowski, P. J., Delp-Archer, C., Rosen, E. M., and Madara, J. L. (1994). Hepatocyte growth factor/scatter factor effects on epithelia. Regulation of intercellular junctions in transformed and nontransformed cell lines, basolateral polarization of c-met receptor in transformed and natural intestinal epithelia, and induction of rapid wound repair in a transformed model epithelium. J Clin Invest 93, 2056-2065.

Ogiso, H., Ishitani, R., Nureki, O., Fukai, S., Yamanaka, M., Kim, J. H., Saito, K., Sakamoto, A., Inoue, M., Shirouzu, M., and Yokoyama, S. (2002). Crystal structure of the complex of human epidermal growth factor and receptor extracellular domains. Cell 110, 775-787.

Olivero, M., Rizzo, M., Madeddu, R., Casadio, C., Pennacchietti, S., Nicotra, M. R., Prat, M., Maggi, G., Arena, N., Natali, P. G., et al. (1996). Overexpression and activation of hepatocyte growth factor/scatter factor in human non-small-cell lung carcinomas. Br J Cancer 74, 1862-1868.

Olivero, M., Valente, G., Bardelli, A., Longati, P., Ferrero, N., Cracco, C., Terrone, C., Rocca-Rossetti, S., Comoglio, P. M., and Di Renzo, M. F. (1999). Novel mutation in the ATP-binding site of the MET oncogene tyrosine kinase in a HPRCC family. Int J Cancer 82, 640-643.

Orian-Rousseau, V., Chen, L., Sleeman, J. P., Herrlich, P., and Ponta, H. (2002). CD44 is required for two consecutive steps in HGF/c-Met signaling. Genes Dev 16, 3074-3086.

Park, M., Dean, M., Cooper, C. S., Schmidt, M., O'Brien, S. J., Blair, D. G., and Vande Woude, G. F. (1986). Mechanism of met oncogene activation. Cell 45, 895-904.

Peek, M., Moran, P., Mendoza, N., Wickramasinghe, D., and Kirchhofer, D. (2002). Unusual proteolytic activation of pro-hepatocyte growth factor by plasma kallikrein and coagulation factor XIa. J Biol Chem 277, 47804-47809.

Pelicci, G., Giordano, S., Zhen, Z., Salcini, A. E., Lanfrancone, L., Bardelli, A., Panayotou, G., Waterfield, M. D., Ponzetto, C., Pelicci, P. G., and et al. (1995). The motogenic and mitogenic responses to HGF are amplified by the Shc adaptor protein. Oncogene 10, 1631-1638.

Plotnikov, A. N., Schlessinger, J., Hubbard, S. R., and Mohammadi, M. (1999). Structural basis for FGF receptor dimerization and activation. Cell 98, 641-650.

Ponzetto, C., Bardelli, A., Zhen, Z., Maina, F., dalla Zonca, P., Giordano, S., Graziani, A., Panayotou, G., and Comoglio, P. M. (1994). A multifunctional docking site mediates signaling and transformation by the hepatocyte growth factor/scatter factor receptor family. Cell 77, 261-271.

Ponzetto, C., Zhen, Z., Audero, E., Maina, F., Bardelli, A., Basile, M. L., Giordano, S., Narsimhan, R., and Comoglio, P. (1996). Specific uncoupling of GRB2 from the Met receptor. Differential effects on transformation and motility. J Biol Chem 271, 14119-14123.

Robertson, S. C., Tynan, J. A., and Donoghue, D. J. (2000). RTK mutations and human syndromes when good receptors turn bad. Trends Genet 16, 265-271.

Royal, I., and Park, M. (1995). Hepatocyte growth factor-induced scatter of Madin-Darby canine kidney cells requires phosphatidylinositol 3-kinase. J Biol Chem 270, 27780-27787.

Schmidt, C., Bladt, F., Goedecke, S., Brinkmann, V., Zschiesche, W., Sharpe, M., Gherardi, E., and Birchmeier, C. (1995). Scatter factor/hepatocyte growth factor is essential for liver development. Nature 373, 699-702.

Schmidt, L., Duh, F. M., Chen, F., Kishida, T., Glenn, G., Choyke, P., Scherer, S. W., Zhuang, Z., Lubensky, I., Dean, M., et al. (1997). Germline and somatic mutations in the tyrosine kinase domain of the MET proto-oncogene in papillary renal carcinomas. Nat Genet 16, 68-73.

Schmidt, L., Junker, K., Nakaigawa, N., Kinjerski, T., Weirich, G., Miller, M., Lubensky, I., Neumann, H. P., Brauch, H., Decker, J., et al. (1999). Novel mutations of the MET proto-oncogene in papillary renal carcinomas. Oncogene 18, 2343-2350.

Suzuki, K., Hayashi, N., Yamada, Y., Yoshihara, H., Miyamoto, Y., Ito, Y., Ito, T., Katayama, K., Sasaki, Y., Ito, A., and et al. (1994). Expression of the c-met protooncogene in human hepatocellular carcinoma. Hepatology 20, 1231-1236.

Tamagnone, L., Artigiani, S., Chen, H., He, Z., Ming, G. I., Song, H., Chedotal, A., Winberg, M. L., Goodman, C. S., Poo, M., et al. (1999). Plexins are a large family of receptors for transmembrane, secreted, and GPI-anchored semaphorins in vertebrates. Cell 99, 71-80.

Tempest, P. R., Stratton, M. R., and Cooper, C. S. (1988). Structure of the met protein and variation of met protein kinase activity among human tumour cell lines. Br J Cancer 58, 3-7.

Trusolino, L., Bertotti, A., and Comoglio, P. M. (2001). A signaling adapter function for alpha6beta4 integrin in the control of HGF-dependent invasive growth. Cell 107, 643-654.

Uehara, Y., Minowa, O., Mori, C., Shiota, K., Kuno, J., Noda, T., and Kitamura, N. (1995). Placental defect and embryonic lethality in mice lacking hepatocyte growth factor/scatter factor. Nature 373, 702-705.

Van Vactor, D. V., and Lorenz, L. J. (1999). Neural development: The semantics of axon guidance. Curr Biol 9, R201-204.

Weidner, K. M., Di Cesare, S., Sachs, M., Brinkmann, V., Behrens, J., and Birchmeier, W. (1996). Interaction between Gab1 and the c-Met receptor tyrosine kinase is responsible for epithelial morphogenesis. Nature 384, 173-176.

Wiesmann, C., Fuh, G., Christinger, H. W., Eigenbrot, C., Wells, J. A., and de Vos, A. M. (1997). Crystal structure at 1.7 A resolution of VEGF in complex with domain 2 of the Flt-1 receptor. Cell 91, 695-704.

Wiesmann, C., Ultsch, M. H., Bass, S. H., and de Vos, A. M. (1999). Crystal structure of nerve growth factor in complex with the ligand-binding domain of the TrkA receptor. Nature 401, 184-188.

The invention claimed is:

1. An isolated anti-c-met antibody comprising a light chain variable region comprising three light chain hypervariable region (HVR) sequences and a heavy chain comprising three heavy chain HVR sequences, wherein at least one HVR is a variant of SEQ ID NO: 2, 4, 5, or 143, wherein:
   (a) HVR-L1 comprises sequence A1-A17, wherein A1-A17 is KSSQSLLYTSSQKNYLA (SEQ ID NO:1);
   (b) HVR-L2 comprises sequence B1-B7, wherein B1-B7 is WASTRES (SEQ ID NO:2), or a variant thereof, wherein said variant comprises 1-7 (1, 2, 3, 4, 5, 6, or 7) substitutions in any combination of the following positions: B1 (M or L), B2 (P, T, G or S), B3 (N, G, R or T), B4 (I, N or F), B5 (P, I, L or G), B6 (A, D, T or V) and B7 (R, I, M or G);
   (c) HVR-L3 comprises sequence C1-C9, wherein C1-C9 is QQYYAYPWT (SEQ ID NO:3);
   (d) HVR-H1 comprises sequence D1-D10, wherein D1-D10 is GYTFTSYWLH (SEQ ID NO:4), or a variant thereof, wherein said variant comprises 1-5 (1, 2, 3, 4 or 5) substitutions in any combination of the following positions: D3 (N, P, L, S, A, I), D5 (I, S or Y), D6 (G, D, T, K, R), D7 (F, H, R, S, T or V) and D9 (M or V);
   (e) HVR-H2 comprises sequence E1-E18, wherein E1-E18 is GMIDPSNSDTRFNPNFKD (SEQ ID NO:5), or a variant thereof, wherein said variant comprises 1-8 (1, 2, 3, 4, 5, 6, 7 or 8) substitutions in any combination of the following positions: E7 (Y), E9 (I), E10 (I), E14 (T or Q), E15 (D, K, S, T or V), E16 (L), E17 (E, H, N, Q or D) and E18 (Y, E or H); and
   (f) HVR-H3 comprises sequence F1-F11, wherein F1-F11 is SYGSYVSPLDY (SEQ ID NO:143), or a variant thereof, wherein said variant comprises 1-8 (1, 2, 3, 4, 5, 6, 7, or 8) substitutions in any combination of the following positions: F1 (T), F3 (R, S), F4 (G), F6 (R, F, M, T, E, K, A, L, W), F7 (L, I, T, R, K, V), F8 (S, A), F10 (Y, N) and F11 (Q, S, H, F).

2. The antibody of claim 1, wherein HVR-L2 comprises any one of SEQ ID NOs: 56-75; HVR-H1 comprises any one of SEQ ID NOs: 76-96; and HVR-H2 comprises any one of SEQ ID NOs: 97-112.

3. The antibody of claim 2, wherein the HVR-H3 variant comprises the following substitutions: F1 is T or S, F3 is R or S, F7 is T or S, and F8 is P, S or A.

4. The antibody of claim 1, wherein HVR-L1 comprises sequence A1-A17, wherein A1-A17 is KSSQSLLYTSSQKNYLA (SEQ ID NO:1); HVR-L2 comprises any one of SEQ ID NOs: 56-75; HVR-L3 comprises sequence C1-C9, wherein C1-C9 is QQYYAYPWT (SEQ ID NO:3); HVR-H1 comprises sequence D1-D10, wherein D1-D10 is GYTFTSYWLH (SEQ ID NO:4); HVR-H2 comprises sequence E1-E18, wherein E1-E18 is GMIDPSNSDTRFNPNFKD (SEQ ID NO:5); and HVR-H3 is a variant of SEQ ID NO:143 and comprises the following substitutions: F1 is T or S, F3 is R or S, F7 is T or S, and F8 is P, S or A.

5. The antibody of claim 1, wherein HVR-L1 comprises sequence A1-A17, wherein A1-A17 is KSSQSLLYTSSQKNYLA (SEQ ID NO:1); HVR-L2 comprises sequence B1-B7, wherein B1-B7 is WASTRES (SEQ ID NO:2); HVR-L3 comprises sequence C1-C9, wherein C1-C9 is QQYYAYPWT (SEQ ID NO:3); HVR-H1 comprises any one of SEQ ID NOs: 76-96; HVR-H2 comprises sequence E1-E18, wherein E1-E18 is GMIDPSNSDTRFNPNFKD (SEQ ID NO:5); and HVR-H3 is a variant of SEQ ID NO:143 and comprises the following substitutions: F1 is T or S, F3 is R or S, F7 is T or S, and F8 is P, S or A.

6. The antibody of claim 1, wherein HVR-L1 comprises sequence A1-A17, wherein A1-A17 is KSSQSLLYTSSQKNYLA (SEQ ID NO:1); HVR-L2 comprises sequence B1-B7, wherein B1-B7 is WASTRES (SEQ ID NO:2); (iii) HVR-L3 comprises sequence C1-C9, wherein C1-C9 is QQYYAYPWT (SEQ ID NO:3); HVR-H1 comprises sequence D1-D10, wherein D1-D10 is GYTFTSYWLH (SEQ ID NO:4); HVR-H2 comprises any one of SEQ ID NOs:97-112; and HVR-H3 is a variant of SEQ ID NO:143 and comprises the following substitutions: F1 is T or S, F3 is R or S, F7 is T or S, and F8 is P, S or A.

7. The antibody of claim 1, wherein HVR-L1 comprises sequence A1-A17, wherein A1-A17 is KSSQSLLYTSSQKNYLA (SEQ ID NO:1); HVR-L2 comprises sequence B1-B7, wherein B1-B7 is WASTRES (SEQ ID NO:2); (iii) HVR-L3 comprises sequence C1-C9, wherein C1-C9 is QQYYAYPWT (SEQ ID NO:3); HVR-H1 comprises sequence D1-D10, wherein D1-D10 is GYTFTSYWLH (SEQ ID NO:4); HVR-H2 comprises sequence E1-E18, wherein E1-E18 is GMIDPSNSDTRFNPNFKD (SEQ ID NO:5); and HVR-H3 is a variant of SEQ ID NO:143 and comprises the following substitutions: F1 is T or S, F3 is R or S, F7 is T or S, and F8 is P, S or A.

8. The antibody of claim 7, wherein HVR-H3 comprises sequence F1-F11, wherein F1-F11 is TYRSYVTPLDY (SEQ ID NO:159).

9. The antibody of claim 1 or 8, which is a monoclonal antibody.

10. The antibody of claim 1 or 8, which is a humanized antibody.

11. The antibody of claim 1 or 8, which is an antibody fragment that binds c-met.

12. The antibody of claim 1 or 8, further comprising human κ subgroup 1 consensus framework sequence.

13. The antibody of claim 1 or 8, further comprising heavy chain human subgroup III consensus framework sequence.

14. The antibody of claim 12, wherein the framework sequence comprises a substitution at position 71 and/or 73, amino acid position numbering as in Kabat.

15. The nucleic acid of claim 13, wherein said substitution is R71A and/or N73T.

16. The antibody of claim 1 or 8, wherein the antibody is monovalent and comprises an Fc region, wherein the Fc region comprises a first and a second polypeptide, wherein the first and second polypeptide each comprises one or more mutations with respect to wild type human Fc.

17. The antibody of claim 16, wherein the first polypeptide comprises the Fc sequence depicted in FIG. 13 (SEQ ID NO: 195) and the second polypeptide comprises the sequence depicted in FIG. 14 (SEQ ID NO: 196).

18. An isolated anti-c-met antibody comprising a light chain variable region comprising three light chain hypervariable region (HVR) sequences and a heavy chain comprising three heavy chain HVR sequences, wherein at least one HVR is a variant of SEQ ID NO: 2, 4, 5, or 143, wherein:
    (a) HVR-L1 comprises sequence A1-A17, wherein A1-A17 is KSSQSLLYTSSQKNYLA (SEQ ID NO:1);
    (b) HVR-L2 comprises any one of SEQ ID NOs: 56-75;
    (c) HVR-L3 comprises sequence C1-C9, wherein C1-C9 is QQYYAYPWT (SEQ ID NO:3);
    (d) HVR-H1 comprises any one of SEQ ID NOs: 76-96;
    (e) HVR-H2 comprises any one of SEQ ID NOs: 97-112; and
    (f) HVR-H3 comprises sequence F1-F11, wherein F1-F11 is SYGSYVSPLDY (SEQ ID NO:143), or a variant thereof, wherein said variant comprises 1-8 (1, 2, 3, 4, 5, 6, 7, or 8) substitutions in any combination of the following positions: F1 (T), F3 (R, S, H, T, A, K), F4 (G), F6 (R, F, M, T, E, K, A, L, W), F7 (L, I, T, R, K, V), F8 (S, A), F10 (Y, N) and F11 (Q, S, H, F).

19. The antibody of claim 18, wherein HVR-H3 comprises any one of SEQ ID NOs: 113-138 and 144-163.

20. The antibody of claim 18, which is a monoclonal antibody.

21. The antibody of claim 18, which is a humanized antibody.

22. The antibody of claim 18, which is an antibody fragment that binds c-met.

23. The antibody of claim 18, further comprising human κ subgroup 1 consensus framework sequence.

24. The antibody of claim 18, further comprising heavy chain human subgroup III consensus framework sequence.

25. The antibody of claim 24, wherein the framework sequence comprises a substitution at position 71 and/or 73, amino acid position numbering as in Kabat.

26. The antibody of claim 25, wherein said substitution is R71A and/or N73T.

27. The antibody of claim 18, wherein the antibody is an IgG1 antibody.

28. The antibody of claim 18, wherein the antibody is monovalent and comprises an Fc region, wherein the Fc region comprises a first and a second polypeptide, wherein the first and second polypeptide each comprises one or more mutations with respect to wild type human Fc.

29. The antibody of claim 28, wherein the first polypeptide comprises the Fc sequence depicted in FIG. 13 (SEQ ID NO: 195) and the second polypeptide comprises the sequence depicted in FIG. 14 (SEQ ID NO: 196).

30. An isolated anti-c-met antibody comprising a heavy chain variable domain comprising sequence depicted in SEQ ID NO:197.

31. The antibody of claim 30, wherein the antibody comprises HVR1-HC, HVR2-HC and/or HVR3-HC sequence depicted in FIG. 13 (SEQ ID NO: 191-193), and further comprises FR1-HC, FR2-HC, FR3-HC and/or FR4-HC sequence depicted in FIG. 13 (SEQ ID NO: 187-190).

32. The antibody of claim 30, wherein the antibody is monovalent and comprises an Fc region, wherein the Fc region comprises a first and a second polypeptide, wherein the first and second polypeptide each comprises one or more mutations with respect to wild type human Fc.

33. The antibody of claim 32, wherein the first polypeptide comprises the Fc sequence depicted in FIG. 13 (SEQ ID NO: 195) and the second polypeptide comprises the sequence depicted in FIG. 14 (SEQ ID NO: 196).

34. The antibody of claim 30 or 31, wherein the antibody further comprises a light chain variable domain.

35. The antibody of claim 30, wherein the antibody further comprises HVR1-LC, HVR2-LC and/or HVR3-LC sequence depicted in FIG. 13 (SEQ ID NO:183-185), and further comprises FR1-LC, FR2-LC, FR3-LC and/or FR4-LC sequence depicted in FIG. 13 (SEQ ID NO: 179-182).

36. An isolated nucleic acid encoding the antibody of claim 1.

37. An isolated nucleic acid encoding the antibody of claim 8.

38. An isolated nucleic acid encoding the antibody of claim 18.

39. An isolated nucleic acid encoding the antibody of claim 30.

40. An isolated nucleic acid encoding the antibody of claim 35.

41. An isolated nucleic acid encoding an anti-c-met antibody comprising (a) a heavy chain variable domain comprising HVR1-HC, HVR2-HC and HVR3-HC sequence depicted in FIG. 13 (SEQ ID NO: 191-193); and (b) a light chain variable domain comprising HVR1-LC, HVR2-LC and HVR3-LC sequence depicted in FIG. 13 (SEQ ID NO: 183-185).

42. The nucleic acid of claim 41, wherein the heavy chain variable domain comprises FR1-HC, FR3-HC and FR4-HC sequence depicted in FIG. 13 (SEQ ID NO: 187-90).

43. The nucleic acid of claim 41, wherein the light chain variable domain comprises FR1-LC, FR2-LC, FR3-LC and FR4-LC sequence depicted in FIG. 13 (SEQ ID NO: 179-182).

44. The nucleic acid of claim 41, wherein the heavy chain variable domain comprises FR1-HC, FR2-HC, FR3-HC and FR4-HC sequence depicted in FIG. 13 (SEQ ID NO: 187-90) and the light chain variable domain comprises FR1-LC, FR2-LC, FR3-LC and FR4-LC sequence depicted in FIG. 13 (SEQ ID NO: 179-182).

45. The nucleic acid of claim 44, wherein the antibody comprises CH1 sequence depicted in FIG. 13 (SEQ ID NO: 194).

46. The nucleic acid of claim 44, wherein the antibody comprises CL1 sequence depicted in FIG. 13 (SEQ ID NO: 186).

47. The nucleic acid of claim 44, wherein the antibody comprises Fc sequence depicted in FIG. 13 (SEQ ID NO: 195).

48. The nucleic acid of claim 44, wherein the antibody is monovalent and comprises a Fc region, wherein the Fc region comprises a first and a second polypeptide, wherein the first polypeptide comprises the Fc sequence depicted in FIG. 13 (SEQ ID NO: 195) and the second polypeptide comprises the sequence depicted in FIG. 14 (SEQ ID NO: 196).

49. The nucleic acid of claim 41, wherein the antibody is monovalent and comprises an Fc region.

50. An isolated host cell comprising the nucleic acid of claim 36.

51. An isolated host cell comprising the nucleic acid of claim 37.

52. An isolated host cell comprising the nucleic acid of claim 38.

53. An isolated host cell comprising the nucleic acid of claim 39.

54. An isolated host cell comprising the nucleic acid of claim 40.

55. An isolated host cell comprising the nucleic acid of claim 41.

56. An isolated host cell comprising the nucleic acid of claim 48.

57. A pharmaceutical formulation comprising the antibody of any one of claims 1, 8, 18, 30 or 35, and a pharmaceutically acceptable carrier.

58. A method of making an antibody, said method comprising culturing the host cell of any one of claims 50, 51, 52, 53, 54, 55, or 56 so that the antibody is produced.

59. The method of claim 58, further comprising recovering the antibody from the host cell.

60. The method of claim 59, further comprising combining the recovered antibody with a pharmaceutically acceptable carrier, excipient, or carrier to prepare a pharmaceutical formulation comprising the antibody.

61. The method of claim 58, comprising culturing the host cell of claim 50.

62. The method of claim 58, comprising culturing the host cell of claim 51.

63. The method of claim 58, comprising culturing the host cell of claim 52.

64. The method of claim 58, comprising culturing the host cell of claim 53.

65. The method of claim 58, comprising culturing the host cell of claim 54.

66. The method of claim 58, comprising culturing the host cell of claim 55.

67. The method of claim 58, comprising culturing the host cell of claim 56.

* * * * *